(12) United States Patent
Lu et al.

(10) Patent No.: US 9,315,806 B2
(45) Date of Patent: Apr. 19, 2016

(54) MASSIVELY PARALLEL COMBINATORIAL GENETICS

(71) Applicant: Massachusetts Institute of Technology, Cambridge, MA (US)

(72) Inventors: Timothy Kuan-Ta Lu, Charlestown, MA (US); Allen Cheng, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/411,628

(22) PCT Filed: Jun. 28, 2013

(86) PCT No.: PCT/US2013/048619
§ 371 (c)(1),
(2) Date: Dec. 29, 2014

(87) PCT Pub. No.: WO2014/005042
PCT Pub. Date: Jan. 3, 2014

(65) Prior Publication Data
US 2015/0141263 A1    May 21, 2015

Related U.S. Application Data

(60) Provisional application No. 61/666,081, filed on Jun. 29, 2012.

(51) Int. Cl.
| | | |
|---|---|---|
| *C12N 15/70* | (2006.01) | |
| *C12N 15/10* | (2006.01) | |
| *C12Q 1/68* | (2006.01) | |
| *G01N 35/00* | (2006.01) | |

(52) U.S. Cl.
CPC ........ *C12N 15/1065* (2013.01); *C12N 15/1027* (2013.01); *C12N 15/1079* (2013.01); *C12Q 1/6869* (2013.01); *G01N 2035/00752* (2013.01)

(58) Field of Classification Search
None
See application file for complete search history.

(56) References Cited

U.S. PATENT DOCUMENTS

| 2005/0170373 A1 | 8/2005 | Monforte |
| 2008/0269068 A1 | 10/2008 | Church et al. |
| 2009/0098555 A1 | 4/2009 | Roth et al. |
| 2011/0092387 A1 | 4/2011 | Monforte |
| 2012/0028814 A1 | 2/2012 | Toloue et al. |

FOREIGN PATENT DOCUMENTS

WO    WO 2012/019765 A1    2/2012

OTHER PUBLICATIONS

Anderson et al., A flexible standard for biological part assembly. J Biol Eng. Jan. 20, 2010;4(1):1. doi: 10.1186/1754-1611-4-1.
Chang et al., Lessons from Nature: microRNA-based shRNA libraries. Nat Methods. Sep. 2006;3(9):707-14.
Cheng et al., Enhanced killing of antibiotic-resistant bacteria enabled by massively parallel combinatorial genetics. Proc Natl Acad Sci U S A. Aug. 26, 2014;111(34):12462-7. doi: 10.1073/pnas.1400093111. Epub Aug. 11, 2014.
Cheng et al., Synthetic biology: an emerging engineering discipline. Annu Rev Biomed Eng. 2012;14:155-78. doi: 10.1146/annurev-bioeng-071811-150118. Epub May 7, 2012.
Dymond et al., Synthetic chromosome arms function in yeast and generate phenotypic diversity by design. Nature. Sep. 14, 2011;477(7365):471-6. doi: 10.1038/nature10403. Supplementary Information.
Merryman et al., Methods and applications for assembling large DNA constructs. Metab Eng. May 2012;14(3):196-204.
Sarrion-Perdigones et al., GoldenBraid: an iterative cloning system for standardized assembly of reusable genetic modules. PLoS One. p2011;6(7):e21622. doi: 10.1371/journal.pone.0021622. Epub Jul. 7, 2011.
Wingler et al., Reiterative Recombination for the in vivo assembly of libraries of multigene pathways. Proc Natl Acad Sci U S A. Sep. 13, 2011;108(37):15135-40. doi: 10.1073/pnas.1100507108. Epub Aug. 26, 2011.
Antoine et al., Isolation and molecular characterization of a novel broad-host-range plasmid from Bordetella bronchiseptica with sequence similarities to plasmids from gram-positive organisms. Molec Microbiol. 1992;6:1785-99.
Barnhart et al., Curli biogenesis and function. Annu Rev Microbiol. 2006;60:131-47.
Beaumont et al., Expression of nitrite reductase in Nitrosomonas europaea involves NsrR, a novel nitrite-sensitive transcription repressor. Mol Microbiol. 2004;54:148-58.
Beggah et al., Mutant HbpR transcription activator isolation for 2-chlorobiphenyl via green fluorescent protein-based flow cytometry and cell sorting. Microbiol Biotechnol. 2008;1:68-78.
Brinkhoff et al., Diversity, ecology, and genomics of the Roseobacter Glade: a short overview. Arch Microbiol. 2008;189:531-9.
Burgstaller et al., Structural probing and damage selection of citrulline- and arginine-specific RNA aptamers identify base positions required for binding. Nucl Acids Res. 1995;23:4769-76.
Butland et al., eSGA: *E. coli* synthetic genetic array analysis. Nat Methods. Sep. 2008;5(9):789-95. doi: 10.1038/nmeth.1239.
Changela et al., Molecular basis of metal-ion selectivity and zeptomolar sensitivity by CueR. Science. 2003;301:1383-7.
Chapman et al., Role of *Escherichia coli* curli operons in directing amyloid fiber formation. Science. 2002;295:851-5.

(Continued)

*Primary Examiner* — Jim Ketter
(74) *Attorney, Agent, or Firm* — Wolf, Greenfield & Sacks, P.C.

(57) ABSTRACT

The invention relates to methods and compositions that enable the rapid generation of high-order combinations of genetic elements, and that provide a barcoded basis for rapid characterization of the specific combination of genetic elements encoded within a single cell or in a pooled population.

16 Claims, 35 Drawing Sheets

(56) References Cited

OTHER PUBLICATIONS

Chasteen et al., Eliminating helper phage from phage display. Nucl Acids Res. 2006;34:e145.
Choi et al., A portable toxicity biosensor using freeze-dried recombinant bioluminescent bacteria. Biosensors Bioelectron. 2002;17:433-40.
Costantino et al., Enhanced levels of lambda Red-mediated recombinants in mismatch repair mutants. Proc Natl Acad Sci U S A. 2003;100:15748-53.
Delany et al., Fur functions as an activator and as a repressor of putative virulence genes in Neisseria meningitidis. Mol Microbiol. 2004;52:1081-90.
Du et al., Customized optimization of metabolic pathways by combinatorial transcriptional engineering. Nucl Acids Res. 2012;40:e142.
Dueholm et al., Functional amyloid in Pseudomonas. Mol Microbiol. Aug. 2010;77(4):1009-20.
Eacker et al., Understanding microRNAs in neurodegeneration. Nat Rev Neurosci. Dec. 2009;10(12):837-41. doi: 10.1038/nrn2726. Review. Epub Aug. 4, 2014. 12 pages.
Ellis et al., High efficiency mutagenesis, repair, and engineering of chromosomal DNA using single-stranded oligonucleotides. Proc Natl Acad Sci U S A. 2001;98:6742-6.
Fang et al., Stable antibody expression at therapeutic levels using the 2A peptide. Nat Biotechnol. May 2005;23(5):584-90. Epub Apr. 17, 2005.
Ferré-D'Amaré et al, Small self-cleaving ribozymes. Cold Spring Harb Perspect Biol. 2010;2:a003574.
Friedland et al., Synthetic gene networks that count. Science. 2009;324:1199-202.
Galvao et al., Emergence of novel functions in transcriptional regulators by regression to stem protein types. Mol Microbiol. 2007;65:907-19.
Gangaraju et al., MicroRNAs: key regulators of stem cells. Nat Rev Mol Cell Biol. Feb. 2009;10(2):116-25. doi: 10.1038/nrm2621. Review. Epub Aug. 1, 2014. 21 pages.
Geiger et al., RNA aptamers that bind L-arginine with sub-micromolar dissociation constants and high enantioselectivity. Nucl Acids Res. 1996;24:1029-36.
Georgellis et al., Quinones as the redox signal for the arc two-component system of bacteria. Science. 2001;292:2314-6.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gilles-Gonzalez et al., Heme-based sensors: defining characteristics, recent developments, and regulatory hypotheses. J Inorganic Biochem. 2005;99:1-22.
Guzzo et al., Characterization of the effects of aluminum on luciferase biosensors for the detection of ecotoxicity. Toxicol Lett. 1992;64-65:687-93.
Hakkila et al., Reporter genes lucFF, luxCDABE, gfp, and dsred have different characteristics in whole-cell bacterial sensors. Anal Biochem. 2002;301:235-242.
Ivask et al., A suite of recombinant luminescent bacterial strains for the quantification of bioavailable heavy metals and toxicity testing. BMC Biotechnol. 2009;9:41.
Jenison et al., High-resolution molecular discrimination by RNA. Science. 1994;263:1425-9.
Jensen et al., Engineering of a synthetic electron conduit in living cells. Proc Natl Acad Sci U S A. 2010;107:19213-8.
Joung et al., A bacterial two-hybrid selection system for studying protein-DNA and protein-protein interactions. Proc Nat Acad Sci U S A. 2000;97:7382-7.
Kaseniit et al., Designing Extensible Protein-DNA Interactions for Synthetic Biology. IEEE Biomedical Circuits and Systems Conference. San Diego, CA. Nov. 10-12, 2011;349-52.
Khalil et al., A Synthetic Biology Framework for Programming Eukaryotic Transcription Functions. Cell. 2012;150:647-58.
Kitagawa et al., Complete set of ORF clones of *Escherichia coli* ASKA library (a complete set of *E. coli* K-12 ORF archive): unique resources for biological research. DNA Res. 2005;12(5):291-9. Epub Jan. 9, 2006.
Kong et al., microRNAs in cancer management. Lancet Oncol. Jun. 2012;13(6):e249-58. doi: 10.1016/S1470-2045(12)70073-6. Review.
Kues et al., Replication of plasmids in gram-negative bacteria. Microbiol Rev. 1989;53:491-516.
Lampson et al., Retrons, msDNA, and the bacterial genome. Cytogenet Genome Res. 2005;110:491-9.
Levskaya et al., Synthetic biology: engineering *Escherichia coli* to see light. Nature. 2005;438:441-2.
Lim et al., Reverse transcriptase-dependent synthesis of a covalently linked, branched DNA-RNA compound in *E. coli* B. Cell. 1989;56:891-904.
Looger et al., Computational design of receptor and sensor proteins with novel functions. Nature. 2003;423:185-90.
Lorsch et al., In vitro selection of RNA aptamers specific for cyanocobalamin. Biochem. 1994;33:973-82.
Lu et al., Dispersing biofilms with engineered enzymatic bacteriophage. Proc Nat Acad Sci U S A. 2007;104:11197-202.
Lu et al., Engineered bacteriophage targeting gene networks as adjuvants for antibiotic therapy. Proc Natl Acad Sci U S A. 2009;106:4629-34.
Lu et al., The next generation of bacteriophage therapy. Curr Opin Microbiol. 2011;14:524-31.
Maas et al., Multicopy single-stranded DNA of *Escherichia coli* enhances mutation and recombination frequencies by titrating MutS protein. Mol Microbiol. 1996;19:505-9.
Maas et al., Multicopy single-stranded DNAs with mismatched base pairs are mutagenic in *Escherichia coli*. Mol Microbiol. 1994;14:437-41.
Maeder et al., Rapid "Open-Source" Engineering of Customized Zinc-Finger Nucleases for Highly Efficient Gene Modification. Mol Cell. 2008;31:294-301.
Mao et al., Gene regulation by antisense DNA produced in vivo. J Biol Chem. 1995;270:19684-7.
Mitra et al., WebGeSTer DB—a transcription terminator database. Nucl Acids Res. 2010;1-7. doi:10.1093/nar/gkq971.
Mochon et al., New Delhi metallo-β-lactamase (NDM-1)-producing Klebsiella pneumoniae: case report and laboratory detection strategies. J Clin Microbiol. Apr. 2011;49(4):1667-70. doi: 10.1128/JCM.00183-11. Epub Feb. 16, 2011. Erratum in: J Clin Microbiol. Jun. 2011;49(6):2386.
Moglich et al., Structural basis for light-dependent signaling in the dimeric LOV domain of the photosensor YtvA. J Molec Biol. 2007;373:112-26.
Mosberg et al., Improving lambda red genome engineering in *Escherichia coli* via rational removal of endogenous nucleases. PLoS One. 2012;7:e44638.
Mutalik et al., Quantitative Estimation of Activity and Quality for Collections of Functional Genetic Elements. Nature Meth. Apr. 2013;10(4):347-53. doi:10.1038/nmeth.2403.
Nakamura et al., SOS-inducing activity of chemical carcinogens and mutagens in *Salmonella typhimurium* TA1535/pSK1002: examination with 151 chemicals. Mut Res. 1987;192:239-46.
Nishigaki et al., Type II restriction endonucleases cleave single-stranded DNAs in general. Nucl Acids Res. 1985;13:5747-60.
O'Toole et al., Biofilm formation as microbial development. Annu Rev Microbiol. 2000;54:49-79.
Pan et al., A robust toolkit for functional profiling of the yeast genome. Mol Cell. Nov. 5, 2004;16(3):487-96.
Peitzsch et al., Alcaligenes eutrophus as a bacterial chromate sensor. Appl Environ Microbiol. 1998;64:453-8.
Piekarski et al., Genetic tools for the investigation of Roseobacter Glade bacteria. BMC Microbiol. 2009;9:265. doi:10.1186/1471-2180-9-265.
Purnick et al., The second wave of synthetic biology: from modules to systems. Nat Rev Mol Cell Biol. 2009;10:410-22.
Quan et al., Circular polymerase extension cloning for high-throughput cloning of complex and combinatorial DNA libraries. Nature Prot. 2011;6:242-51.

(56) References Cited

OTHER PUBLICATIONS

Rayssiguier et al., The barrier to recombination between *Escherichia coli* and *Salmonella typhimurium* is disrupted in mismatch-repair mutants. Nature. 1989;342:396-401.
Reyon et al., FLASH assembly of TALENs for high-throughput genome editing. Nat Biotech. 2012;30:460-5.
Sander et al., Selection-free zinc-finger-nuclease engineering by context-dependent assembly (CoDA). Nat Methods. 2011;8:67-9.
Sassanfar et al., An RNA motif that binds ATP. Nature. 1993;364:550-3.
Sawitzke et al., Probing cellular processes with oligo-mediated recombination and using the knowledge gained to optimize recombineering. J Mol Biol. 2011;407:45-59.
Sharon et al., Inferring gene regulatory logic from high-throughput measurements of thousands of systematically designed promoters. Nat Biotechnol. May 20, 2012;30(6):521-30. doi: 10.1038/nbt.2205. Epub May 20, 2012. 13 pages.
Shingler et al., Sensing of aromatic compounds by the DmpR transcriptional activator of phenol-catabolizing *Pseudomonas* sp. strain CF600. J Bacteriol. 1994;176:1555-60.
Son et al., Conversion of mouse and human fibroblasts into functional spinal motor neurons. Cell Stem Cell. Sep. 2, 2011;9(3):205-18. doi: 10.1016/j.stem.2011.07.014.
Soo et al., Artificial gene amplification reveals an abundance of promiscuous resistance determinants in *Escherichia coli*. Proc Natl Acad Sci U S A. Jan. 25, 2011;108(4):1484-9. doi: 10.1073/pnas.1012108108. Epub Dec. 20, 2010.
Stoyanov et al., CueR (YbbI) of *Escherichia coli* is a MerR family regulator controlling expression of the copper exporter CopA. Mol Microbiol. 2001;39:502-11.
Swingle et al., Oligonucleotide recombination in Gram-negative bacteria. Mol Microbiol. 2010;75:138-48.
Swingley et al., The Complete Genome Sequence of Roseobacter denitrificans Reveals a Mixotrophic Rather than Photosynthetic Metabolism. J Bacteriol. 2007;189:683-90.
Tauriainen et al., Luminescent bacterial sensor for cadmium and lead. Biosensors Bioelectron. 1998;13:931-8.
Tecon et al., Development of a multistrain bacterial bioreporter platform for the monitoring of hydrocarbon contaminants in marine environments. Environ Sci Technol. 2010;44:1049-55.
Tibazarwa et al., A microbial biosensor to predict bioavailable nickel in soil and its transfer to plants. Environ Pollut. 2001;113:19-26.
Timmis, Pseudomonas putida: a cosmopolitan opportunist par excellence. Environ Microbiol. 2002;4:779-81.
Tokishita et al., Transmembrane signal transduction and osmoregulation in *Escherichia coli*. Functional importance of the periplasmic domain of the membrane-located protein kinase, EnvZ. J Biol Chem. 1991;266:6780-5.
Tong et al., Global mapping of the yeast genetic interaction network. Science. Feb. 6, 2004;303(5659):808-13.
Wagner-Döbler et al., Environmental Biology of the Marine Roseobacter Lineage. Annu Rev Microbiol. 2006;60:255-80.
Wang et al., Programming cells by multiplex genome engineering and accelerated evolution. Nature. Aug. 13, 2009;460(7257):894-8. doi: 10.1038/nature08187. Epub Jul. 26, 2009.
Wang et al., Specific binding of aminoglycoside antibiotics to RNA. Chem Biol. 1995;2:281-90.
Westwater et al., Development of a P1 phagemid system for the delivery of DNA into Gram-negative bacteria. Microbiol. 2002;148:943-50.
Willardson et al., Development and testing of a bacterial biosensor for toluene-based environmental contaminants. Appl Environ Microbiol. 1998;64:1006-12.
Wilson et al., In vitro selection of functional nucleic acids. Annu Rev Biochem. 1999;68:611-47.
Wise et al., Generation of novel bacterial regulatory proteins that detect priority pollutant phenols. Appl Envir Microbiol. 2000;66:163-9.
Wright et al., Standardized reagents and protocols for engineering zinc finger nucleases by modular assembly. Nat Protocols. 2006;1:1637-52.
Yee et al., Multicopy single-stranded DNA isolated from a gram-negative bacterium, Myxococcus xanthus. Cell. 1984;38:203-9.
Yu et al., Next-generation sequencing to generate interactome datasets. Nat Methods. Jun. 2011;8(6):478-80. doi: 10.1038/nmeth.1597. Epub Dec. 1, 2011. 12 pages.
Zhang et al., High frequency targeted mutagenesis in Arabidopsis thaliana using zinc finger nucleases. Proc Nat Acad Sci U S A. 2010;107:12028-33.

Key:

B1 __*__ B2 + P1 _____ P2

L1 __*__ L2 + R1 _____ R2 http://wolfson.huji.ac.il/expression/gatewayman.pdf

Iterate

Intended Product

Vector-vector recombination

MASSIVELY PARALLEL COMBINATORIAL GENETICS

RELATED APPLICATIONS

This application is a national stage filing under 35 U.S.C. §371 of international application number PCT/US2013/048619, filed Jun. 28, 2013, which was published under PCT Article 21(2) in English and claims the benefit under 35 U.S.C. §119(e) of U.S. provisional application Ser. No. 61/666,081, filed Jun. 29, 2012, each of which is herein incorporated by reference in its entirety.

GOVERNMENT INTEREST

This invention was made with government support under Grant No. DP2 OD008435 awarded by the National Institutes of Health. The government has certain rights in this invention.

FIELD OF THE INVENTION

The invention relates to methods and compositions for the rapid generation of high-order combinations of genetic elements and the facile identification of genetic elements.

BACKGROUND OF INVENTION

Biology has perennially been limited by the inability to generate complex cellular perturbations. Previous studies have screened for desired phenotypes using only single gene overexpression studies (Kitagawa et al. (2005) *DNA Research* 12:291-9; Soo et al. (2011) *Proc Natl Acad Sci USA* 108:1484-9) and single gene knockout studies, as well as a limited set of double-knockout studies (Butland et al. (2008) *Nature Methods* 5:789-95; Pan et al. (2004) *Molecular Cell* 16:487-96; Tong et al. (2004) *Science* 303:808-13). These methods, however, are not scalable to generating higher-order combinations of perturbations, preventing a more powerful and complex interrogation of networks. Furthermore, these methods are not easily scalable to generating more than a few thousand combinations. This prevents the screening and study of millions of combinations in a high-throughput pooled fashion, instead relying on well- or colony-based screening. Finally, these methods are not designed to enable rapid characterization of specific combinations.

SUMMARY OF INVENTION

Described herein are methods and compositions that enable the rapid generation of high-order combinations of genetic elements and that provide a barcoded basis for rapid characterization of the specific combination of genetic elements encoded within a single cell or in a pooled population. These novel approaches carry broad implications for multiple fields, enabling a vast set of investigations where generating combinations of genetic elements is informative and productive. This technology can yield new insights into complex phenotypes and emergent network properties which have previously been inaccessible to study.

Aspects of the invention relate to a genetic construct comprising: a DNA element; a first compatible end element and a second compatible end element flanking the DNA element, wherein the first and second compatible end elements are capable of annealing to each other; a barcode element; a third compatible end element and a fourth compatible end element flanking the barcode element, wherein the third and fourth compatible end elements are capable of annealing to each other but are not capable of annealing to the first or second compatible end elements; and a separation site located between the fourth compatible end element and the first compatible end element, wherein the DNA element, first compatible end element and second compatible end element are on one side of the separation site, and the barcode element, third compatible end element and fourth compatible end element are on the other side of the separation site.

Further aspects of the invention relate to a genetic construct comprising: a plurality of DNA elements; a first compatible end element and a second compatible end element flanking the plurality of DNA elements, wherein the first and second compatible end elements are capable of annealing to each other; a plurality of barcode elements; a third compatible end element and a fourth compatible end element flanking the plurality of barcode elements, wherein the third and fourth compatible end elements are capable of annealing to each other but are not capable of annealing to the first or second compatible end elements; and a separation site located between the plurality of DNA elements and the plurality of barcode elements.

Further aspects of the invention relate to a method for generating a combinatorial genetic construct, comprising: providing a vector containing a first genetic construct associated with the invention; cleaving the vector at the separation site within the first genetic construct, resulting in the first genetic construct being separated into first and second segments; providing a second genetic construct associated with the invention; and annealing the second genetic construct to the cleaved vector, wherein the annealing occurs at compatible end elements within the first and second genetic constructs that are capable of annealing to each other, and wherein after annealing, the second genetic construct is integrated between the first and second segments of the first genetic construct, creating a combinatorial genetic construct. In some embodiments, the method is iterative.

Further aspects of the invention relate to methods for identification of a DNA element or a plurality of DNA elements, comprising: providing a genetic construct associated with the invention; conducting an assay to determine the DNA sequence of the barcode or plurality of barcodes within the genetic construct and/or the DNA sequence of the DNA element or plurality of DNA elements within the genetic construct; and identifying the DNA element or plurality of DNA elements.

Further aspects of the invention relate to a library comprising: two or more genetic constructs associated with the invention.

Further aspects of the invention relate to methods for generating a combinatorial genetic construct, comprising: providing a vector comprising: a first DNA element, a first barcode element, and two site-specific recombination elements located between the first DNA element and the first barcode element; providing a first insert comprising: a second DNA element, a second barcode element, and site-specific recombination elements flanking each of the second DNA element and the second barcode element, such that two site-specific recombination elements are located between the second DNA element and the second barcode element that are not compatible with the site-specific recombination elements within the vector, and two site-specific recombination elements are located outside of the second DNA element and the second barcode element that are compatible with the site-specific recombination elements within the vector; conducting site specific recombination between the vector and the first insert, wherein the site specific recombination occurs between the site-specific recombination elements within the vector located between the first DNA element and the first barcode element and the compatible site-specific recombination elements within the first insert located outside of the second DNA element and the second barcode element, and wherein following site-specific recombination, the first insert is located within the vector, and the vector contains multiple DNA elements and multiple barcode elements, with two site-specific recombination elements located between the multiple DNA elements and the multiple barcode elements; providing a second insert comprising: a third DNA element, a third barcode element, and site-specific recombination elements flanking each of the third DNA element and the third barcode element, such that two site-specific recombination elements are located between the third DNA element and the third barcode element that are not compatible with the two site-specific recombination elements located between the multiple DNA elements and the multiple barcode elements of the vector, and two site-specific recombination elements are located outside of the third DNA element and the third barcode element that are compatible with the two site-specific recombination elements located between the multiple DNA elements and the multiple barcode elements of the vector; conducting site specific recombination between the vector and the second insert, wherein the site specific recombination occurs between the site-specific recombination elements within the vector located between the multiple DNA elements and the multiple barcode elements and the compatible site-specific recombination elements within the second insert located outside of the third DNA element and the third barcode element, and wherein following site-specific recombination, the second insert is located within the vector, and the vector contains multiple DNA elements and multiple barcode elements, with two site-specific recombination elements located between the multiple DNA elements and the multiple barcode elements; and repeating the site-specific recombination an $n^{th}$ number of times, alternating between site-specific recombination between the vector and the first insert and site-specific recombination between the vector and the second insert, thereby creating a combinatorial genetic construct.

Further aspects of the invention relate to a combinatorial genetic construct produced by such methods. Further aspects of the invention relate to a method for identification of a DNA element or a plurality of DNA elements within such a combinatorial genetic construct, comprising: providing a combinatorial genetic construct; conducting an assay to determine the DNA sequence of one or more barcode elements within the combinatorial genetic construct and/or the DNA sequence of one or more DNA elements within the combinatorial genetic construct; and identifying the DNA element or plurality of DNA elements.

Further aspects of the invention relate to methods for generating a combinatorial genetic construct, comprising: providing a vector comprising: a first DNA element, a first barcode element, and a recognition site for a first restriction enzyme located between the first DNA element and the first barcode element; providing an insert comprising: a second DNA element, a second barcode element, a recognition site for the first restriction enzyme located between the second DNA element and the second barcode element, and two recognition sites for one or more restriction enzymes that are distinct from the first restriction enzyme located outside of the second DNA element and second barcode element, such that restriction digestion at the recognition site within the vector and at the two recognition sites located outside of the second DNA element and second barcode element within the insert generates compatible ends; digesting the vector and insert with restriction enzymes; annealing the insert to the vector, thereby producing a combinatorial genetic construct containing multiple DNA elements and multiple barcode elements; and optionally repeating the method an $n^{th}$ number of times.

Further aspects of the invention relate to a combinatorial genetic construct produced by such methods. Further aspects of the invention relate to methods for identification of a DNA element or a plurality of DNA elements within such a combinatorial genetic construct, comprising: providing a combinatorial genetic construct; conducting an assay to determine the DNA sequence of one or more barcode elements within the combinatorial genetic construct and/or the DNA sequence of one or more DNA elements within the combinatorial genetic construct; and identifying the DNA element or plurality of DNA elements.

These and other aspects of the invention, as well as various embodiments thereof, will become more apparent in reference to the drawings and detailed description of the invention.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows the creation of a unique barcoded construct for each unique DNA element. FIG. 1B shows that genetic constructs associated with aspects of the invention can give rise to a vector (e.g., via restriction enzyme cleavage) and to a homologous insert (e.g., via PCR). Compatible ends can anneal and become ligated. FIG. 1C shows that combinatorial constructs associated with aspects of the invention allow rapid identification of DNA elements via sequencing of the unique barcodes (arrow), and retention of separation sites to allow for further insertions.

FIG. 2A depicts gel electrophoresis of an uncut plasmid showing an increase of approximately ~1 kb with each addition, corresponding to the length of the insertion. FIG. 2B depicts a restriction digest at two sites flanking the construct region, showing increasing lengths.

FIG. 6A shows verified sequences for pairwise, 3×, and 4× combinations from individual colonies. SpeI and AvrII restriction sites flank the barcode region. The sequences, from left to right and top to bottom, correspond to SEQ ID NOs: 19-24. FIG. 6B shows restriction digestion of plasmid isolates for a barcoded gene alone (1×), and 2×-4× combinations. Each plasmid was digested to separate the variable combinatorial region (indicated by dots) from the constant remainder of the vector.

DETAILED DESCRIPTION

Figure 1:
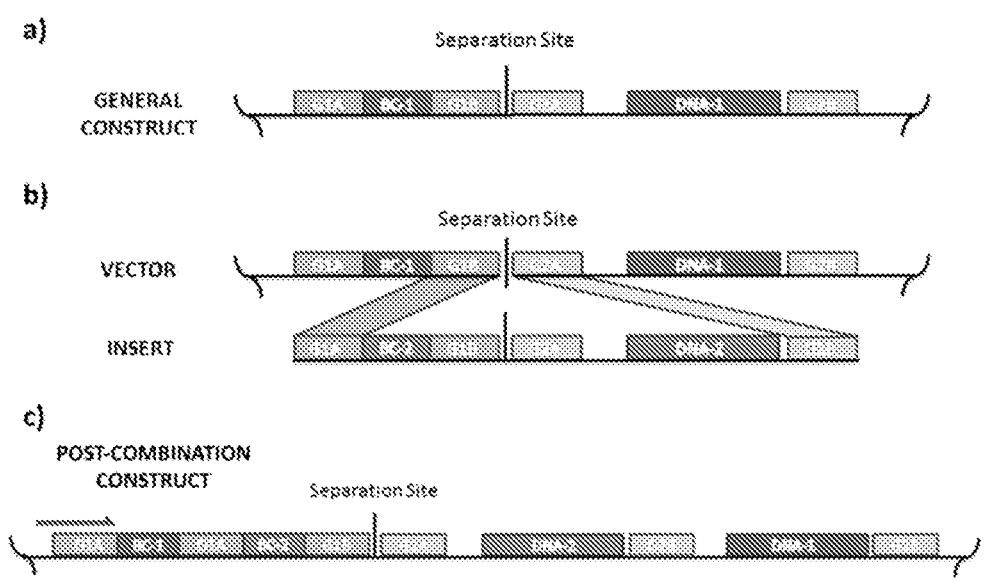
FIG. 1 presents a schematic depicting non-limiting embodiments of the invention.

Described herein is a novel technology, termed Massively Parallel Combinatorial Genetics, which overcomes obstacles that have limited fields such as genetics and systems biology. The invention is based, at least in part, on the surprising discovery of methods and compositions that enable the rapid generation of high-order combinations of genetic elements and the rapid identification of combinations leading to a desired phenotype. This technology enables new research methods and is broadly applicable. The approach described herein presents significant advantages over previous methods, including flexibility of genetic perturbation allowed, ease of use, and rapid scalability to high order combinations.

In the past, large-scale systematic perturbation studies have been limited to low-complexity perturbations. For example, the ASKA library is a library of single-gene overexpression models for all ~4000 open reading frames ("ORFs") in the *E. coli* genome. The ORFs are plasmid-based and arrayed on a large number of plates. Studies have screened this single overexpression library for desired phenotypes, such as antibiotic resistance, and identified clones through individual sequencing (Soo et al. (2011) *Proc Natl Acad Sci USA* 108:1484-9). A pairwise combinatorial strategy could theoretically be derived from this approach by generating another ORF library on a plasmid with a different selection marker, and co-transforming a strain with one member of the ASKA library and one member of the new library. However, an attempt to generate all ~16 million pairwise ORF combinations would immediately be impeded by scale limitations. This is even more apparent when generating higher-order combinations; for example, the low efficiency of simultaneous transformation of multiple vectors and the low number of unique selection markers prevent high-order combinations.

Similar impediments affect previous approaches to combinatorial knockouts. Single-gene knockout libraries have been generated for *E. coli* (e.g., KEIO library) and for *S.*

*cerevisiae*. Barcoded libraries allow pooled screening when paired with high-throughput sequencing. However, there has been no efficient method of generating double-gene knockout libraries. The Synthetic Genetic Array (Tong et al. (2004) *Science* 303:808-13) employs yeast mating to generate double knockouts in a plate-based format; a similar method has been reported in *E. coli* (Butland et al. (2008) *Nature Methods* 5:789-95). However, because mating occurs where two unique strains are co-spotted on a plate, scaling beyond thousands of combinations is impractical. Furthermore, each subsequent experiment requires a laborious process of re-plating the cells.

Combinations of genetic elements have been useful in several specific applications, such as transcription factors in stem cell differentiation. In the past, the typical method has been to co-transfect a cell type with many individual transcription factors and observe differentiation; each member of this pool is then removed one by one until the minimal set to induce differentiation is identified (Son et al. (2011) *Cell Stem Cell* 9:205-18). This method is laborious, as each unique combination requires a separate experiment, and has low efficiency, as it requires co-transfection with many individual elements. These problems are compounded by the fact that differentiation phenotypes are often observed weeks after transfection.

Figure 8:
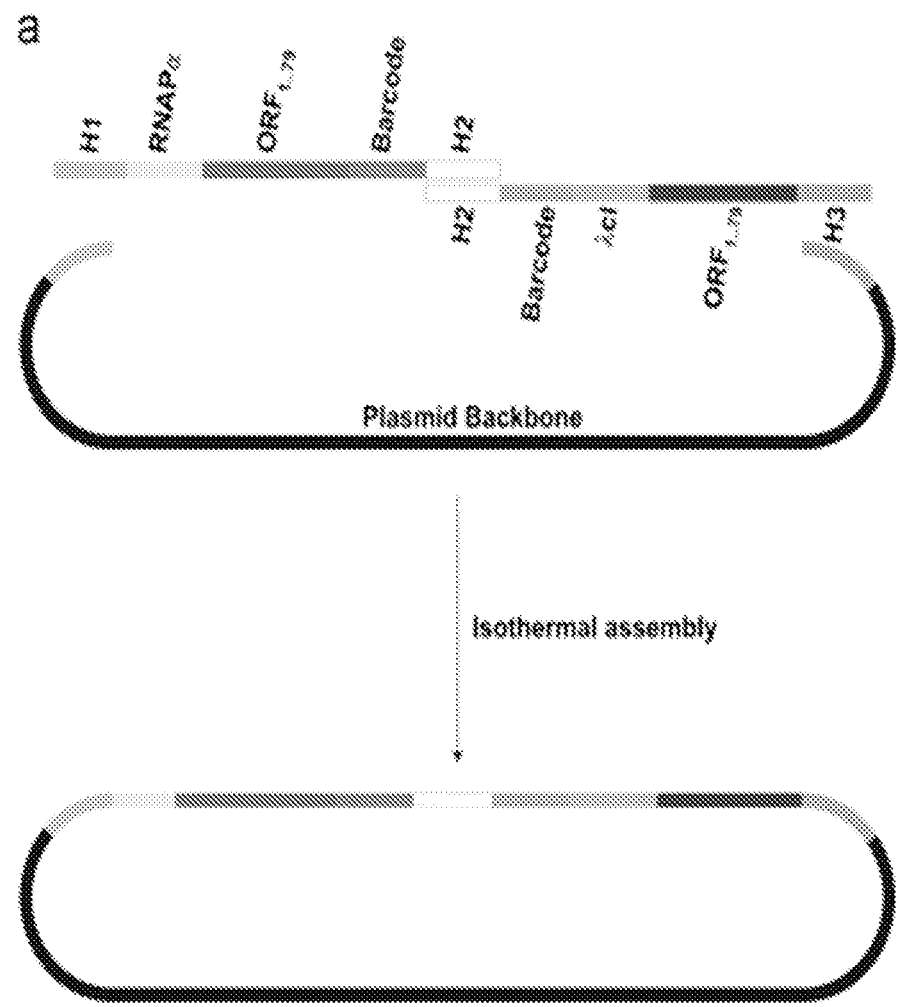
FIG. 8 depicts barcode stitching. Barcodes are placed on either end of DNA elements and fused together. This strategy is limited to pairwise combinations and requires separate libraries for each piece. This Figure is adapted from Merryman (2012) *Metabolic Engineering* 14:196-204.

Recent work has illustrated the concept of back-to-back barcode "stitching" (Merryman (2012) *Metabolic Engineering* 14:196-204; Roth et al. (US Patent Publication No. US 2009/0098555)) wherein two DNA elements with barcodes at the 3' end and 5' end respectively are fused together, placing two barcodes in proximity (FIG. 8). Methods used to accomplish this include PCR overlap and Gibson assembly. The proximity allows combinations to be tracked via sequencing. However, the strategy of that approach is not scalable beyond pairwise combinations. Furthermore, each barcoded piece requires construction of a separate library instead of utilizing the same insert library iteratively.

The Massively Parallel Combinatorial Genetics approach described herein offers multiple advantages relative to previous methods. It enables the rapid generation of combinatorial sets of a variety of genetic elements, such as transcription factors. Furthermore, this technology enables the pooled screening of multiple combination orders (e.g., pairwise, triwise, and n-wise combinations can be pooled and screened together simultaneously), identifying minimal combinations needed for a given application.

A further advantage of technology described herein over past methods is its flexibility in the type of DNA perturbation. Past methods, such as the Synthetic Genetic Array method, for example, are suitable for one technique, such as for generating knockouts, but are not suitable for other types of perturbation. By contrast, technology described herein enables unprecedented combinations of gene overexpression and knockdowns. A further advantage over past methods is that the approach described herein is scalable beyond pairwise combinations.

Aspects of the Massively Parallel Combinatorial Genetics approach relate to genetic constructs that include one or more DNA element(s) and one or more barcode element(s), wherein each specific DNA element is associated with a unique barcode element. As used herein, association between a specific DNA element and a unique barcode element means that a specific DNA element and a unique barcode element are always contained within the same genetic construct. Accordingly, the presence of a unique barcode element within a genetic construct indicates that the associated specific DNA element is also present within the same genetic construct.

It should be appreciated that a DNA element can include any piece of DNA and can have any function or sequence. In some embodiments, the DNA element comprises a gene or gene fragment that may or may not encode a protein. A DNA element can include both coding and non-coding regions. For example, in some embodiments a DNA element can include an open reading frame or fragment thereof, a ribosome binding site, a promoter and/or a terminator. In some embodiments, the DNA element comprises a non-coding DNA, single-stranded DNA or a precursor to RNA such long non-coding RNAs (lncRNA), microRNAs (miRNA)/small interfering RNAs (siRNA) or short hairpin RNA. In some embodiments, the DNA element is a Genome-Wide Association Study (GWAS) implicated gene or a DNA element from genome-wide ORF collections. The DNA element can also include a metagenomic sample or one or more components of a synthetic biology circuit.

In some embodiments, the DNA element(s) encodes for a transcription factor (including endogenous and artificial transcription factors), histone modification enzymes, a microRNA (miR), a kinase or phosphatase, a metabolic enzyme, an epigenetic enzyme, a target of an FDA-approved drug, an oncogene, a monoclonal antibody, and/or a mutant protein.

FIG. 1 presents several schematics of non-limiting examples of genetic constructs associated with the invention. In FIG. 1A, a DNA element, designated DNA-1, is flanked by a first compatible end element, G2A and a second compatible end element, G2B, which are capable of annealing to each other. The genetic construct also contains a barcode element, designated as BC-1, which is flanked by a third compatible end element, G1A and a fourth compatible end element, G1B, which are capable of annealing to each other but are not capable of annealing to G2A or G2B. The genetic construct also contains a separation site, such that the barcode element is on one side of the separation site, while the DNA element is on the other side of the separation site. While FIG. 1 depicts the barcode element as being upstream or 5' relative to the DNA element, this arrangement can also be reversed.

Compatible end elements can be created in a variety of ways familiar to one of ordinary skill in the art and can consist of a variety of different sequences. As used herein, compatible end elements refer to regions of DNA that are capable of ligating or annealing to each other. In several non-limiting embodiments, compatible end elements can be composed of restriction sites with compatible overhangs, Gibson assembly sequences, or functional elements of any other DNA assembly method, including recombinases, meganucleases, TAL Effector/Zinc-finger nucleases, trans-cleaving ribozymes/DNAzymes or integrases.

In some embodiments, Gibson assembly is used to generate compatible overhangs. Gibson assembly refers to an isothermal DNA end-linking technique whereby multiple DNA fragments can be joined in a single reaction. This method is described further in, and incorporated by reference from, Gibson et al. (2009) *Nature Methods* 6:343-5.

Figure 5:
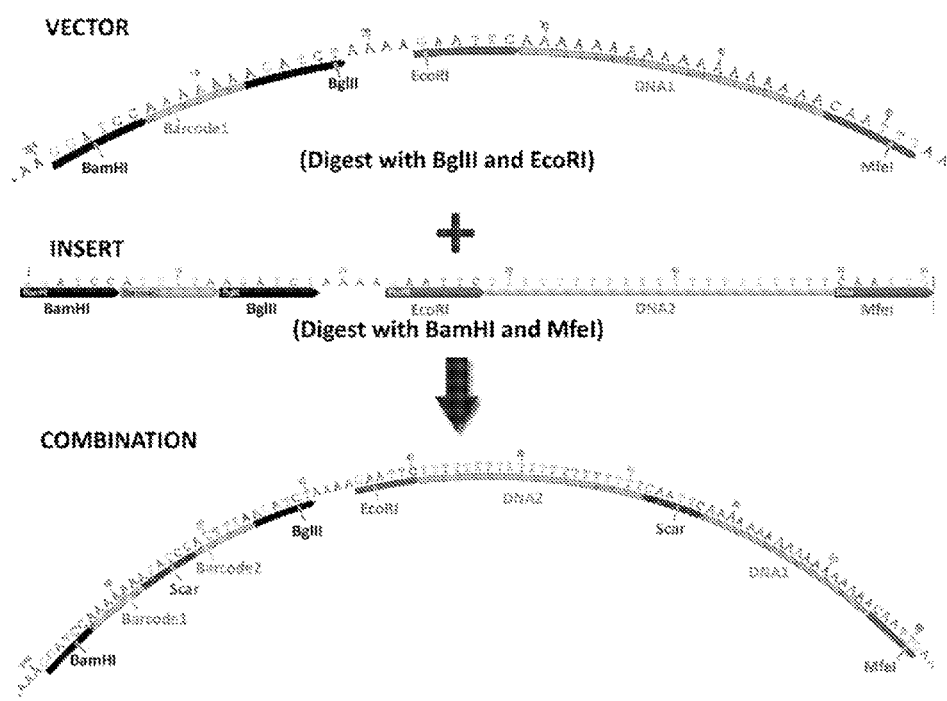
FIG. 5 depicts restriction site conception technology associated with aspects of the invention. Restriction enzymes BamHI and BglII generate compatible overhangs that, when ligated, form a scar not recognized by either enzyme. The separation site consists of BglII and EcoRI restriction sites. Digesting the vector and insert with different restriction enzymes allows insertion of the insert with retention of the Separation Site for further combinations. The sequences, from top to bottom, correspond to SEQ ID NOs: 16-18.

In other embodiments, restriction site digestion is used to generate compatible ends, as depicted in FIG. 5. Using this method, two unique restriction enzymes generate compatible overhangs. When these overhangs are ligated, a scar is created that is no longer recognized by either enzyme. It should be appreciated that any restriction enzymes that generate compatible overhangs can be used. In some non-limiting embodiments, standard biological parts such as BioBricks® (The BioBricks Foundation) or BglBricks (Anderson et al. (2010) *Journal of Biological Engineering* 4:1), and enzymes associated with such standard biological parts, are used. The use of standard biological parts such as BioBricks® or BglBricks would be considered routine to one of ordinary skill in the art. It should be appreciated that while classical restriction enzymes can be used (such as Type I, II or III restriction enzymes), other DNA-cleaving molecules can also be used. For example, targeted ribozymes can be used for cleavage of specific target sites. Meganucleases can also be utilized to minimize the possibility of interference with the inserted DNA elements. TALE or ZF nucleases can also be used to target long DNA sites to minimize the probability of internal cleavage within inserted DNA elements. Furthermore, TOPO® cloning can be used to accomplish restriction digestions and ligations.

The separation site within the genetic construct represents the region that allows linearization of the construct. It should be appreciated that the separation site can correspond to any means of cleaving DNA. In some embodiments, the separation site is a restriction enzyme recognition site.

Further aspects of the invention relate to combinatorial constructs, and methods for producing combinatorial constructs. As used herein, a "combinatorial construct" refers to a genetic construct that contains a plurality of DNA elements. As used herein, a plurality of DNA elements refers to more than one DNA element. As shown in FIG. 1B, the generation of a combinatorial construct can involve the linearization of a vector that contains a first genetic construct associated with the invention, by cleaving the vector at the separation site within the genetic construct. A second genetic construct associated with the invention is depicted in FIG. 1B as an insert. As used herein, an "insert" refers to a genetic construct that is intended to be inserted into a cleaved vector. In some embodiments, the insert is purified from a vector, such as by PCR or restriction digestion. The insert can be ligated to the cleaved vector through the annealing of terminal compatible end elements within the insert and their compatible components within the linearized vector.

FIG. 1C depicts a post-combination combinatorial construct that contains a plurality of DNA elements and a plurality of corresponding barcode elements. In the non-limiting example depicted in FIG. 1C, the genetic construct contains two different DNA elements, termed DNA-1 and DNA-2 and two corresponding barcode elements, termed BC-1 and BC-2. The combinatorial construct further contains a separation site, located between the plurality of barcode elements and the plurality of DNA elements.

Figure 15:
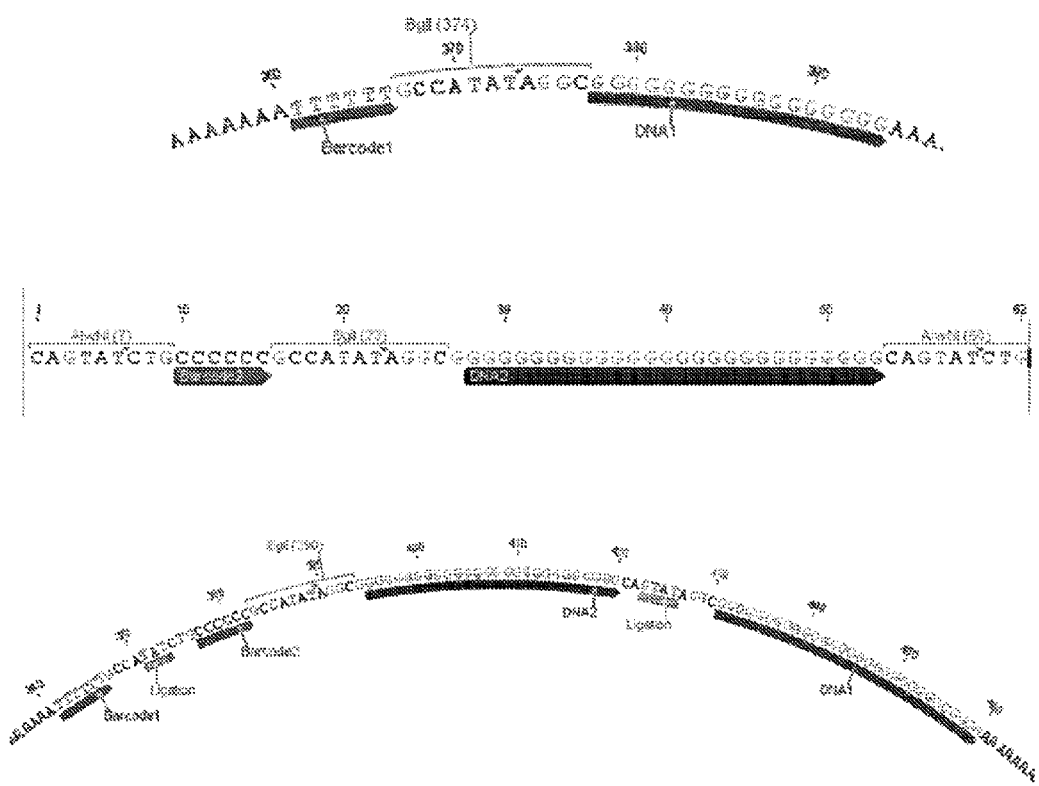
FIG. 15 depicts a non-limiting embodiment of Massively Parallel Combinatorial Genetics using a single enzyme separation site. In this embodiment, a single enzyme, Enzyme 1, cleaves at the separation site of the vector, generating a 3-base 3' overhang. The barcode element and DNA element within the insert are flanked by restriction sites for a different enzyme, Enzyme 2, which generates a compatible overhang with Enzyme 1. Digestion and ligation of the vector and insert produces a vector containing the insert, with a restriction site for Enzyme 1 maintained in the vector. The sequences, from top to bottom, correspond to SEQ ID NOs: 25-27.

The separation site can be a single restriction enzyme recognition site. FIG. 15 shows a non-limiting embodiment of a vector comprising a DNA element and a barcode element separated by a single restriction enzyme site, such as a BglII site. A non-limiting example of a corresponding insert, shown in FIG. 15, contains a DNA element and a barcode element. In some embodiments, a restriction site, such as a BglII site is located between the DNA element and the barcode element of the insert, while two restriction sites, such as AlwNI sites, are located outside of the DNA element and barcode element. BglII and AlwNI generate compatible ends when they cleave DNA. Accordingly, digestion of the vector with BglII and the insert with AlwNI, allows for ligation of the insert into the vector, producing a vector that contains two DNA elements and two barcode elements separated by a restriction site, such as a BglII site.

It should be appreciated that a variety of different enzyme combinations that produce compatible ends when they cleave DNA can be used in conjunction with this aspect of the invention. In some embodiments, within the insert, the two restriction sites located outside of the DNA element and the barcode element are recognized by the same restriction enzyme, which produces compatible ends with the restriction enzyme that digests the vector. In other embodiments, within the insert, the two restriction sites located outside of the DNA element and the barcode element are recognized by two different restriction enzymes, each of which produces compatible ends with the restriction enzyme that digests the vector.

Further aspects of the invention relate to the use of site-specific recombination to generate combinatorial genetic constructs. In such embodiments, genetic constructs associated with the invention do not require a separation site and do not require cleavage by restriction enzymes. A non-limiting example of a recombination-based cloning method is Gateway® cloning technology (Life Technologies, Carlsbad, Calif.), which would be familiar to one of ordinary skill in the art.

Figure 9:
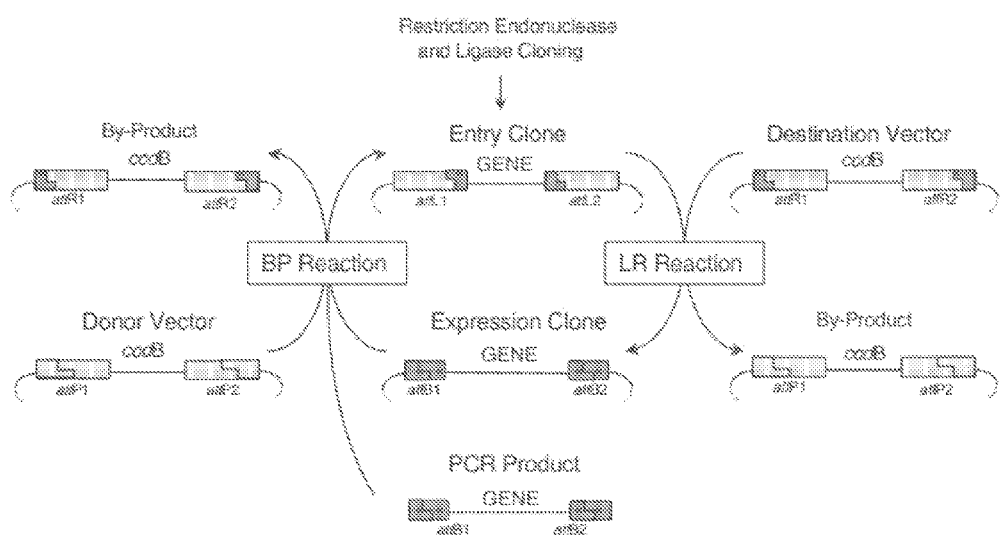
FIG. 9 depicts Gateway® cloning technology that allows for the transfer of DNA without cleavage of DNA (from http://wolfson.huji.ac.il/expression/gatewayman.pdf).

FIG. 9 provides an example of Gateway® cloning methodology. DNA elements are flanked by site-specific recombination elements, which allow for recombination in the presence of Clonase™ enzyme reaction mixtures. Within the Gateway system, site-specific recombination elements are referred to as attachment sites or "att sites," and include attB1, attB2, attP1, attP2, attL1, attL2, attR1 and attR2. attB1 reacts with attP1, attB2 reacts with attP2, attL1 reacts with attR1 and attL2 reacts with attR2. It should be appreciated that any recombination-based cloning method can be compatible with aspects of the invention.

Figure 10:
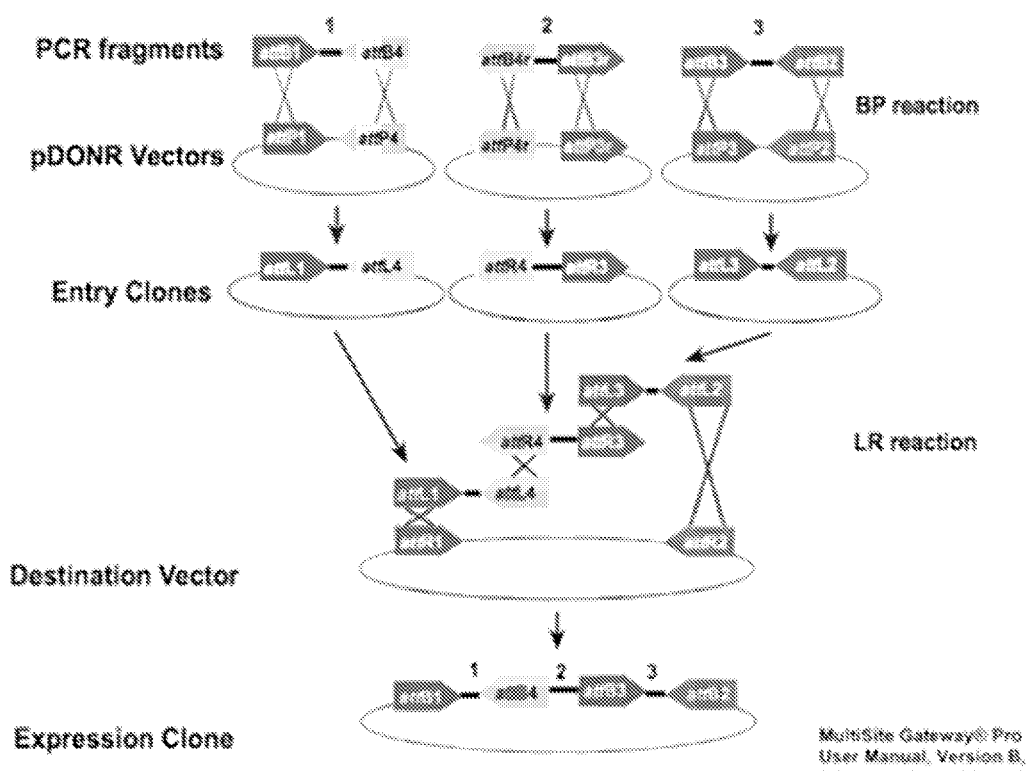
FIG. 10 depicts a non-limiting example of Multisite Gateway® Pro cloning technology for assembling multiple inserts within one genetic construct (from website:pfgrc.jcvi.org/index.php/gateway_clones/about_knockoutclones.html).

FIG. 10 depicts a non-limiting example of Multisite Gateway® Pro cloning technology for assembling multiple inserts within one genetic construct (from http://pfgrc.jcvi.org/index.php/gateway_clones/about_knockoutclones.html).

Figure 11:
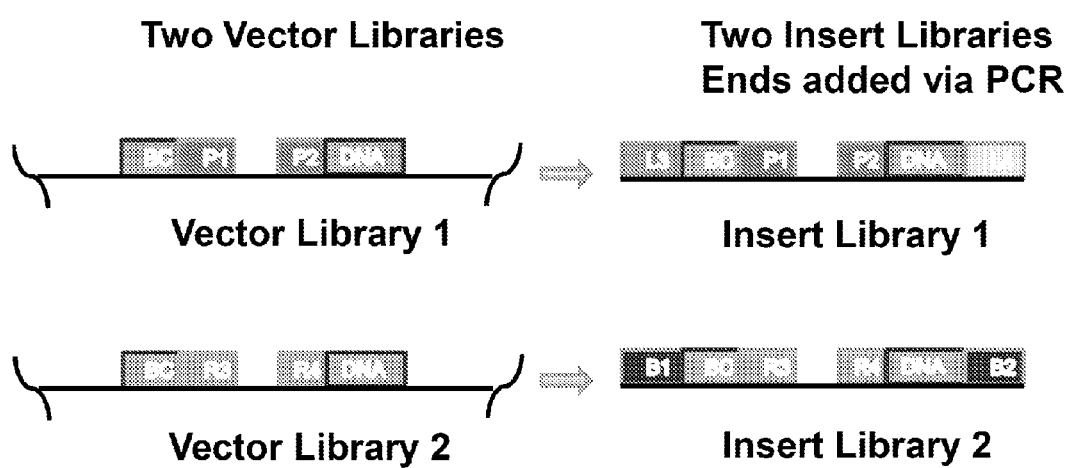
FIG. 11 depicts a non-limiting embodiment whereby two vector libraries with unique recombination sequences can generate, via PCR, two insert libraries with recombination sequences flanking the DNA element and the barcode element within each insert. att recombination sequences are represented by B, P, L or R. BC=Barcode, DNA=DNA element.

FIG. 11 depicts a non-limiting embodiment of a recombination-based combinatorial genetics approach. In this example, two vector libraries are used to generate two insert libraries. Each vector contains a DNA element, a barcode element and two site-specific recombination elements. It should be appreciated that various methods can be used to generate insert libraries. In some embodiments, an insert library, such as insert library 1 or insert library 2 depicted in FIG. 11 is generated from vector libraries such as vector library 1 and vector library 2 depicted in FIG. 11, such as by PCR. In some embodiments, PCR is used to add a flanking pair of orthogonal recombination sequences to the insert libraries.

Figure 12:
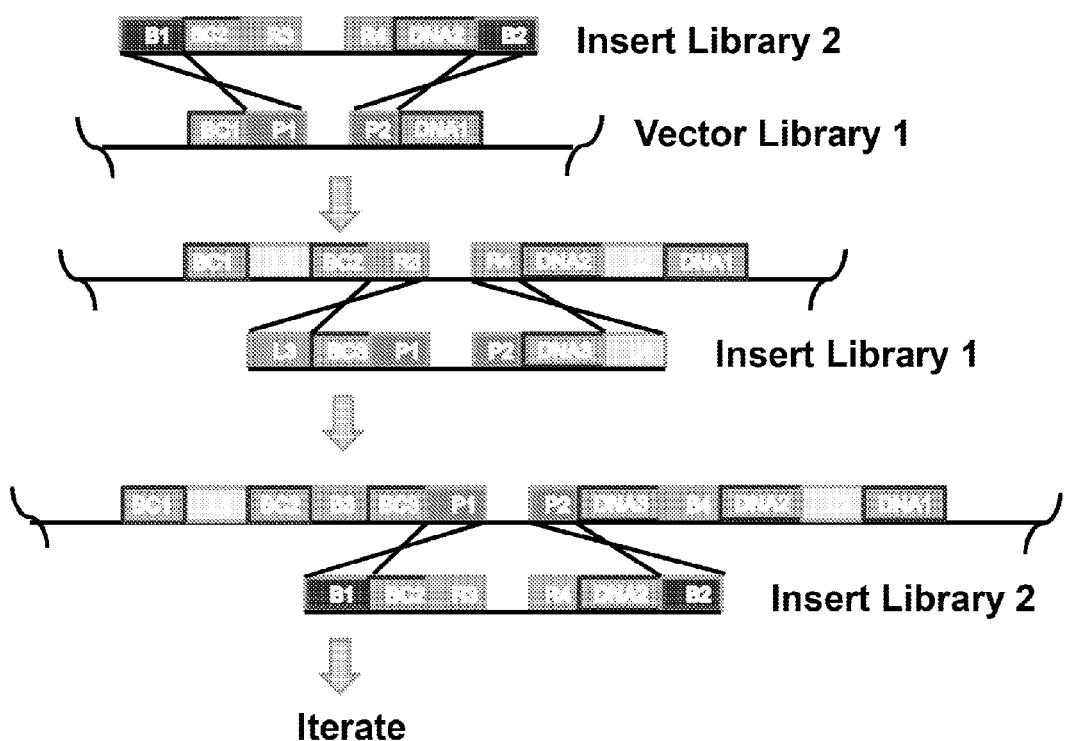
FIG. 12 depicts iterative generation of higher order combinations via recombination-mediated combinatorial genetics using one vector library and two insert libraries. The iterative process alternates between the two insert libraries. Barcodes are in immediate proximity to one another, allowing determination of the barcodes and therefore the identity of downstream DNA elements.

FIG. 12 depicts a non-limiting embodiment whereby recombination-based combinatorial genetics is used to generate a combinatorial genetic construct. In this example, a vector from vector library 1 is shown containing a DNA element, a barcode element, and two site-specific recombination elements located between the DNA element and the barcode element. The vector is recombined with an insert from library 2 which contains a DNA element and a barcode element, each of which is flanked by site-specific recombination elements. Within the insert from library 2, two site-specific recombination elements are located between the DNA element and the barcode element, and two site-specific recombination sequences are located outside of the DNA element and barcode element. The site-specific recombination elements that are located outside of the DNA element and barcode element are compatible with the two site-specific recombination elements in the vector located between the DNA element and barcode element within the vector.

Following recombination at compatible sites, the insert from insert library 2 is contained within the vector, thereby producing a vector that contains two DNA elements and two barcode elements, with two site-specific recombination sites located between the DNA elements and the barcode elements.

As depicted in FIG. 12, the vector can then be recombined with an insert from insert library 1, which contains a DNA element and a barcode element, each of which is flanked by site-specific recombination elements. Within the insert from library 1, two site-specific recombination elements are located between the DNA element and the barcode element, and two site-specific recombination sequences are located outside of the DNA element and barcode element. The site-specific recombination elements that are located outside of the DNA element and barcode element are compatible with the two site-specific recombination elements in the vector located between the DNA element and barcode element within the vector.

Following recombination, the insert from insert library 1 is contained within the vector, thereby producing a vector that contains three DNA elements and three barcode elements, with two site-specific recombination sites located between the DNA elements and the barcode elements.

Figure 13:
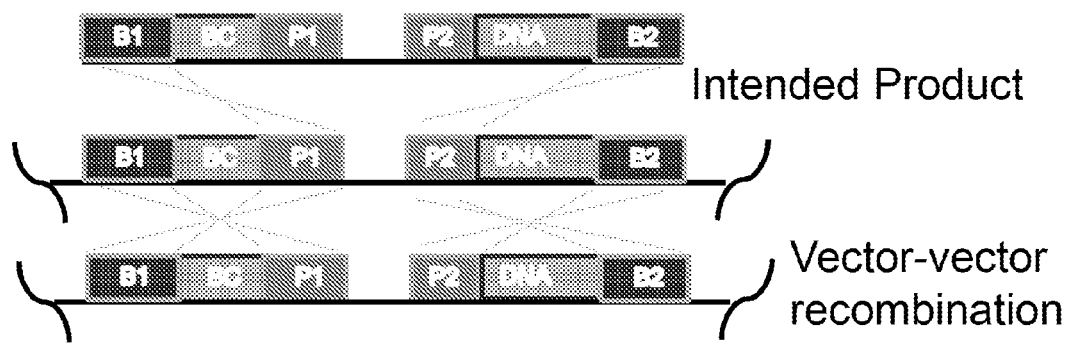
FIG. 13 depicts a non-limiting embodiment whereby the two recombination sequences in the middle of a genetic construct are orthogonal to the ends at all times to avoid self-recombination.
Figure 14:
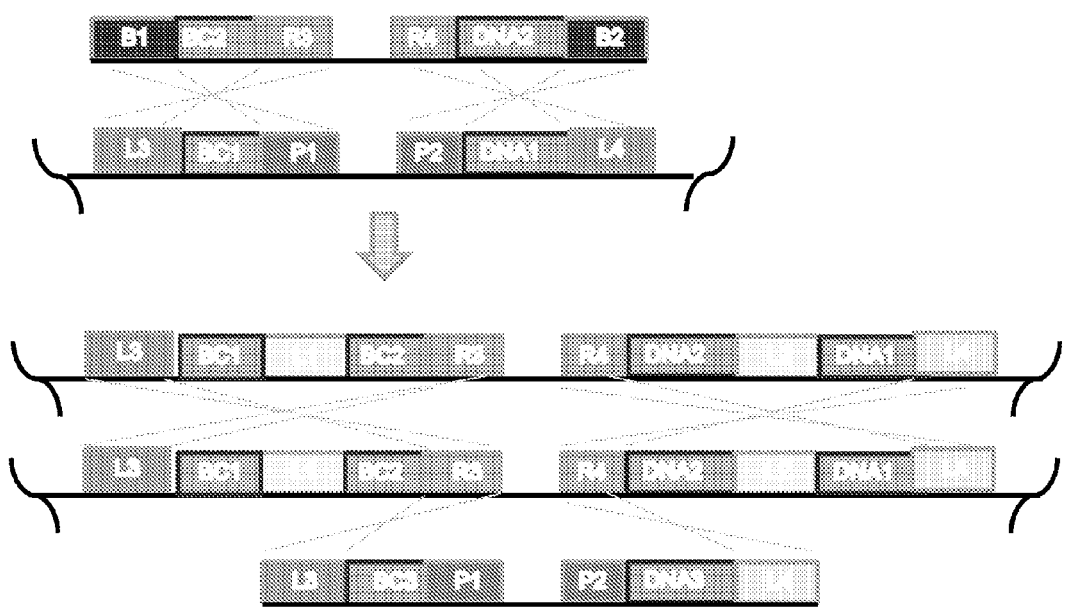
FIG. 14 depicts a non-limiting embodiment of the invention whereby the reactive ends (B1+B2, L3+L4) are added by PCR. This embodiment avoids the vector eventually reacting with itself.

FIGS. 13 and 14 depict how a vector and insert can be designed to recombine with each other while avoiding vector-vector recombination. In some embodiments, site-specific recombination elements are added to the genetic constructs by PCR.

Methods described herein for generating combinatorial constructs can be iterative. For example, the combinatorial construct depicted in FIG. 1C generated through a combination event, can be cleaved again at the separation site, and one or more further inserts can be ligated into the combinatorial construct, while maintaining a separation site for further insertions. Similarly, the vector in FIG. 12 can be alternately recombined with library 1 inserts and with library 2 inserts, generating a combinatorial genetic construct. Significantly, throughout the iterative process, as the number of DNA elements within the genetic construct continues to increase, the unique barcodes associated with each DNA element are maintained within the same genetic construct as their associated DNA elements. In some embodiments, the combination process is repeated at least 2, 3, 4, 5, 6, 7, 8, 9, 10, 11, 12, 13, 14, 15, 16, 17, 18, 19, 20, times or more than 20 times. In some embodiments, the process is repeated an $n^{th}$ number of times, where n can be 1, 2, 3, 4, 5, 6, 7, 8, 9, 10, 11, 12, 13, 14, 15, 16, 17, 18, 19, 20, or a number greater than 20.

It should be appreciated that combinatorial constructs can contain any number of DNA elements and associated barcode elements. In some embodiments a combinatorial construct contains 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 DNA elements and associated barcode elements.

Further aspects of the invention relate to methods for identifying one or more DNA elements within a genetic construct. After a combination event, a unique barcode that is associated with a specific DNA element remains within the same genetic construct as the specific DNA element. Accordingly, identification of a barcode element or plurality of barcode elements allows for the identification of the associated DNA element or plurality of DNA elements within the same genetic construct. In some embodiments, the sequence of a barcode element and/or a DNA element is determined by sequencing or by microarray analysis. It should be appreciated that any means of determining DNA sequence is compatible with identifying one or more barcode elements and corresponding DNA elements. Significantly, in a combinatorial construct, such as is depicted in FIG. 1C, the plurality of barcode elements are within close proximity to each other allowing for the rapid identification of multiple barcode elements, and accordingly multiple DNA elements, simultaneously through methods such as DNA sequencing.

Figure 6:
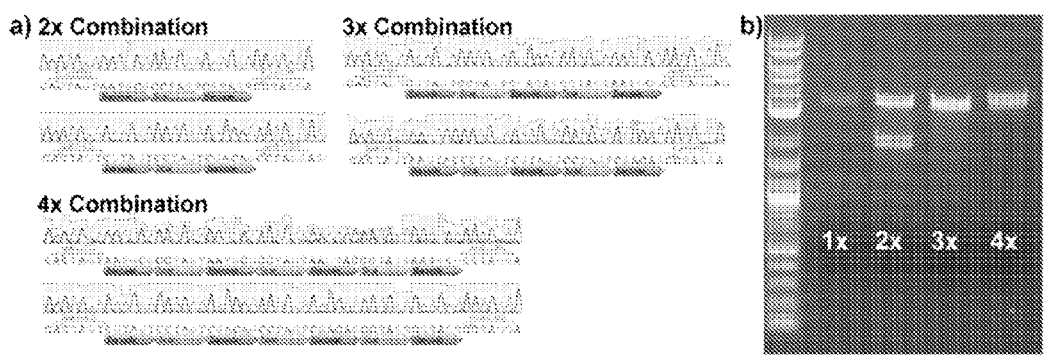
FIG. 6 depicts facile generation of higher-order combinations.

Further aspects of the invention relate to libraries comprising two or more genetic constructs as described herein that are compatible with methods for Massively Parallel Combinatorial Genetics. As used herein, a library of genetic constructs refers to a collection of two or more genetic constructs. In some embodiments, a library of genetic constructs is generated in which each unique DNA element is on a plasmid. This plasmid library can be pooled to form a vector library. An insert library can be generated, for example, by conducting PCR on the vector library. In a first combination event, all of the vectors can be paired with all of the inserts, generating a full combinatorial set of pairwise combinations. Further reactions between this pairwise library and an insert library can lead to a tri-wise, quad-wise or more than quad-wise library arising from a single vector library. FIG. 6 demonstrates effective integration of pairwise, tri-wise and quad-wise combinations of a barcode element.

Some aspects of the invention relate to conducting screens using a library of combinatorial constructs. For example, a pool of cells containing the combinatorial library can be tested for resistance to a stressor such as chemotherapy. To determine which combination of DNA elements is most effective in conferring a particular phenotype, such as resistance to chemotherapy, cells that survive chemotherapy can be isolated and the sequence of the barcode or plurality of barcodes can be determined, allowing for the rapid identification of a DNA element or plurality of DNA elements that is effective in conferring a desired phenotype.

It should be appreciated that since the combinatorial step is conducted in vitro, this technology can be scaled to any organism that can receive DNA. In some embodiments, the organism is bacteria and the constructs are carried on plasmids or phages. In other embodiments, the organism is yeast and the constructs are carried on plasmids or shuttle vectors. In other embodiments, such as in rodent or mammalian cells, genetic constructs described herein can be carried on plasmids or delivered by viruses such as lentiviruses or adenoviruses.

Methods and compositions described herein are broadly applicable to any study that could benefit from the generation of combinatorial sets of genetic elements. For example, this approach could lead to identification of novel drug targets elucidated by network perturbation, which could define more subtle enzymatic pathways leading to disease, or enable drug discovery of novel chemical or biological mediators (including combinations of chemical and/or biological mediators) for treating disease. Additionally, technologies described herein could be applied to the discovery of combinations of existing drug targets for disease treatment and/or prevention, and could lead to novel combination treatments using FDA-approved therapeutics.

Several non-limiting examples of ways in which gene expression can be perturbed according to aspects of the invention include: strong overexpression, tunable overexpression (via tunable inducible promoters), strong knockdown (via short hairpin RNA (shRNA)) or other antisense RNA constructs), and tunable knockdown (via shRNA or other antisense RNA constructs and tunable inducible promoters).

Several non-limiting examples of phenotypes of interest that may be screened or selected for according to aspects of the invention include, in bacteria and fungus (such as yeast): antibiotic resistance or susceptibility, persistence, virulence and metabolic engineering; and in mammalian cells: reduction of disease state, production of disease state, complex multifactorial diseases, aging and age-related diseases, neurodegeneration, chemotherapy resistance, pathway modulation (e.g., stress response), resistance to infection, stem cell differentiation, cell type transdifferentiation and potentiation of FDA-approved drugs.

The ability to tune overexpression or knockdown via tunable inducible promoters enables a set of perturbations far more nuanced than previously possible. One can, for instance, combine multiple levels of overexpression for many proteins and screen for an optimal phenotype, given that network dynamics may best be perturbed through optimization of expression levels. Furthermore, by employing independently inducible promoters for different DNA elements, multiple simultaneous experiments can be run to probe expression space or temporal space.

This technology enables a host of direct biomedical applications. Leveraging gene therapy vectors could result in delivering combinatorial sets of knockdown and overexpression constructs in vitro and in vivo. Non-limiting biomedical applications of this technology include treating multifactorial diseases with complex phenotypes and tissue engineering applications whereby cells are modified and then implanted into humans. Approaches described herein could be applied to combinatorial antibody therapeutics involving combinations of polyclonal and/or monoclonal antibodies. Similarly, combinatorial vaccines could be optimized through combinatorial selection of multiple epitopes.

Moreover, the technology enables fundamental discoveries with broad potential. One example is the global mapping of in vivo protein interactions. By gauging the effects of pairwise or higher order combinations of gene overexpression and knockdown on growth rates and other phenotypes, a comprehensive mapping of protein interactions can be obtained. From this data, interacting pathways and network hubs can be elucidated, leading to a much more nuanced conception of the intracellular protein network and discovery of novel network perturbations for desired phenotypes.

Another fundamental application of the methods, constructs and libraries described herein is to the discovery of determinants of multifactorial diseases. Although gene expression profiles for cells in disease states and genes associated in diseases have been reported, the specific genetic determinants of complex conditions such as diabetes, obesity, and aging are still unknown. Massively parallel combinatorial genetics can produce cells with disease states, yielding new disease models and identifying novel therapeutic targets.

A considerable advantage of this technology to previous approaches is the ability to repurpose a constructed library for investigation of virtually any phenotype. For instance, a pooled combinatorial lentiviral library of all known open reading frames (ORFs) in the human genome can be used to screen for phenotypes ranging from stem cell differentiation to inhibition of cancer metastasis. This dramatically reduces the marginal effort needed to investigate further questions.

The invention encompasses any cell type in which DNA can be introduced, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*.

In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp.

In other embodiments, the cell is an algal cell, a plant cell, an insect cell, a rodent cell or a mammalian cell, including a human cell (e.g., a human embryonic kidney cell (e.g., HEK293T cell), a human dermal fibroblast).

In some embodiments, one or more of the genes associated with the invention is expressed in a recombinant expression vector. As used herein, a "vector" may be any of a number of nucleic acids into which a desired sequence or sequences may be inserted by restriction and ligation or by recombination for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated or recombination sites at which an insert with compatible ends can be integrated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation or recombination such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule. In some embodiments, the promoter is a human ubiquitin C promoter (Ubcp). In some embodiments, the promoter is a human cytomegalovirus promoter (CMVp).

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Fourth Edition, Cold Spring Harbor Laboratory Press, 2012. Cells are genetically engineered by the introduction into the cells of heterologous DNA (RNA). That heterologous DNA (RNA) is placed under operable control of transcriptional elements to permit the expression of the heterologous DNA in the host cell.

A nucleic acid molecule associated with the invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule may also be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, a variety of types of media can be compatible with aspects of the invention. The selected medium can be supplemented with various additional components. Some non-limiting examples of supplemental components include glucose, antibiotics, isopropyl β-D-1-thiogalactopyranoside (IPTG) for gene induction, ATCC Trace Mineral Supplement and glycolate. Similarly, other aspects of the medium and growth conditions of the cells of the invention may be optimized through routine experimentation. For example, pH and temperature are non-limiting examples of factors which can be optimized. In some embodiments the concentration and amount of a supplemental component may be optimized.

Several aspects of the invention relate to the use of Massively Parallel Combinatorial Genetics to identify diverse perturbations in antibiotic-resistance phenotypes using drug resistant (e.g., multi-drug resistant) bacterial or viral strains such as, for example, New Delhi metallo-betalactamase 1 (NDM-1) E. coli strains. In particular, the methods and constructs herein may be used to identify, for example, transcription factor combinations that could potentiate existing antibiotics for treatment. Thus, in some embodiments, provided herein are libraries of pairwise, tri-wise and n-wise (e.g., 4, 5, 6, 7, 8, 9 or 10-wise) combinations of transcription factors (TFs), which can be analyzed through, for example, next-generation sequencing.

In some embodiments, the combinatorial transcription factor libraries may be used to identify combinations (e.g., two or more, such as 2, 3, 4, 5, 6, 7, 8, 9 or 10) of TFs that exhibit synergistic effects with respect to antibiotic resistance phenotypes for a single antibiotic or across a range of antibiotics (e.g., more than one antibiotic, or two, three, four or more antibiotics). In some embodiments, provided herein are constructs that express mtlR and uidR, or qseB and bolA. In some embodiments, provided herein are cells (e.g., bacterial cells) containing constructs that express mtlR and uidR, or qseB and bolA.

In some embodiments, provided herein are constructs that express rstA and rob, rstA and mirA, rcsB and mirA, or feaR and hcaR. In some embodiments, provided herein are cells (e.g., bacterial cells) containing constructs that express rstA and rob, rstA and mirA, rcsB and mirA, or feaR and hcaR.

In some embodiments, the combinatorial transcription factor libraries may be used to identify combinations of TFs that exhibit lethal effects that amplify bactericidal activity of antibiotics. In some embodiments, provided herein are constructs that express torR and metR, nhaR and melR, allR and metJ, malL and yfeT, cadC and allR, torR, metR, or torR. In some embodiments, provided herein are cells (e.g., bacterial cells) containing constructs that express torR and metR, nhaR and melR, allR and metJ, malL and yfeT, cadC and allR, torR or metR.

Antibiotics for use in accordance with the invention include, without limitation, Aminoglycosides, Amikacin, Gentamicin, Kanamycin, Neomycin, Netilmicin, Tobramycin, Paromomycin, Spectinomycin, Ansamycins, Geldanamycin, Herbimycin, Rifaximin, streptomycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftaroline fosamil, Ceftobiprole, Glycopeptides, Teicoplanin, Vancomycin, Telavancin, Lincosamides, Clindamycin, Lincomycin, Lipopeptide, Daptomycin, Macrolides, Azithromycin, Clarithromycin, Dirithromycin, Erythromycin, Roxithromycin, Troleandomycin, Telithromycin, Spiramycin, Monobactams, Aztreonam, Nitrofurans, Furazolidone, Nitrofurantoin, Oxazolidonones, Linezolid, Posizolid, Radezolid, Torezolid, Penicillins, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Penicillin combinations, Amoxicillin/clavulanate, Ampicillin/sulbactam, Piperacillin/tazobactam, Ticarcillin/clavulanate, Polypeptides, Bacitracin, Colistin, Polymyxin B, Quinolones, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Sulfonamides, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Tetracyclines, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin (Rifampin in US), Rifabutin, Rifapentine, Streptomycin, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole and Trimethoprim.

Other antibiotic resistant pathogens contemplated herein include, without limitation, *Staphylococcus aureus, Streptococcus* and *Enterococcus, Pseudomonas aeruginosa, Clostridium difficile, Salmonella, Escherichia coli, Acinetobacter baumannii* and *Mycobacterium tuberculosis*.

Various aspects of the invention relate to the use of Massively Parallel Combinatorial Genetics for elucidating the pathological mechanisms underlying complex human diseases. For example, the methods of the invention may be used to investigate the regulation of lifespan and neurodegenerative disorders in yeast models. Through the exploration of high-order genetic interactions, Massively Parallel Combinatorial Genetics can provide insights into novel therapeutic strategies and drug discovery in age-related diseases. Yeast models have been extensively used to study several human neurodegenerative disorders characterized by protein misfolding and aggregation (summarized in Table 1).

TABLE 1

| Human Neurologic Disorders Modeled in Yeast | |
| --- | --- |
| Disease | Protein |
| Alzheimer's Disease (AD) | amyloid-β (Aβ), APP |
| Parkinson's Disease (PD) | alpha-synuclein (αSyn) |
| Huntington's Disease (HD) | Huntingtin |
| Prion | PrP |
| Amyotrophic lateral sclerosis (ALS) | SOD-1 |
| Friedreich's ataxia (FRDA) | Frataxin |

Among the available yeast models, increased amyloid-β (Aβ) and alpha-synuclein (αSyn), which are widely believed to drive the manifestation of Alzheimer's Disease (AD) and Parkinson's Disease (PD), respectively, profoundly induce cell death in a concentration dependent manner. Most importantly, several genetic factors not only suppress the Aβ or αSyn toxicity in yeast but also rescue key pathological hallmarks in higher model organism of AD and PD. Thus, these two models may be used to explore combinatorial genetic factors that may be beneficial to clinic therapy.

In some embodiments of the invention, yeast strains for genetic screening are generated by integrating multiple tandem copies of a gene of interest such as, for example, alpha-synuclein, or amyloid-β, with an inducible promoter (e.g., galactose (Gal)-inducible promoter). In some embodiments, the yeast strains are engineered to contain the reverse tetracycline transactivator (rtTA), which is part of the Tet-ON expression system. This feature permits expression of a combinatorial library generated using the engineered yeast strain to be controlled by a Tet-ON inducible system (e.g., transcription is reversibly turned on in the presence of the antibiotic tetracycline or one of its derivatives (e.g., doxycycline). In some embodiments, the engineered yeast strains are used in combination with Massively Parallel Combinatorial Genetics to recover genetic combinations that contribute to cell survival with Gal and doxycycline (Dox) treatment.

Aspects of the invention also provide overexpression libraries (e.g., combinatorial libraries) of transcriptional regulators such as, for example, transcriptional factors and histone modification enzymes. In some embodiments, the libraries may also contain yeast genes involved in ubiquitin/proteasome, autophage, and chaperone pathways. Each gene in a library may be flanked by universal restriction enzyme cutting sites to, for example, systematically scale up library assembly and perform high-throughput sequencing for genetic combinations using Massively Parallel Combinatorial Genetics.

Figure 29:
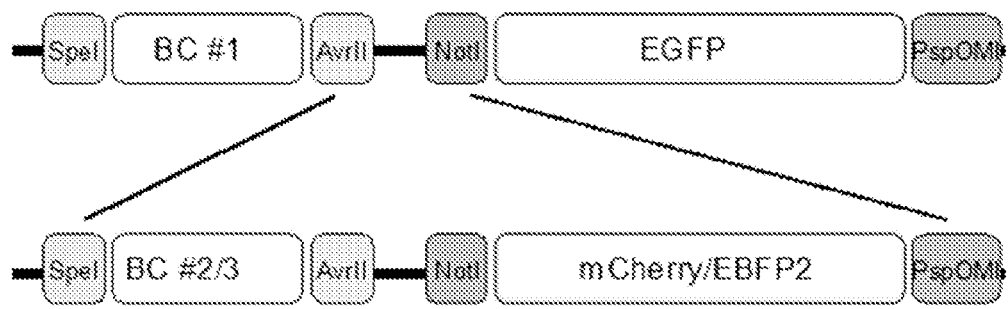
FIG. 29 depicts a single expression construct of a unique barcode (BC) and four restriction sites. The barcoded vectors are pooled and digested with enzymes AvrII+NotI. Inserts are generated by digestion with SpeI+PspOMI. A one-pot ligation reaction produces a pairwise combinatorial library.

In some embodiments, an expression construct of the invention contains a unique barcoded (BC) and four restriction sites positioned as shown in FIG. 29. The barcoded vectors are pooled and digested with enzymes (e.g., AvrII and NotI). Inserts may be generated by digestion with different enzymes (e.g., SpeI and PspOMI). In some embodiments, a "one-pot," or single, ligation reaction may be used to produce a pairwise combinatorial library.

In other aspects of the invention, Massively Parallel Combinatorial Genetics may be used to generate a combinatorial library of microRNAs. Thus, in some embodiments, a DNA element of the invention may encode a microRNA (miR). Herein, a microRNA refers to a non-coding RNA that regulates gene expression through base pairing with canonical sequences present in the 3' untranslated region (3'UTR) of target messenger RNA (mRNA) (Berezikov, E. et al. *Nat Rev Genet* 12, 846-860 (2011)). miRs are first transcribed as precursor-miRs that fold on themselves to form hairpin structures and are processed by Drosha and Dicer/RISC complexes to generate its mature form. Human mature miRs typically exhibit partial complementarity to their mRNA targets. The six to eight-nucleotide-long sequences at the 5' region of miR is believed to be an important determinant of target specificity. As such, a single miR can have multiple mRNA targets, whereas a single mRNA can be targeted by multiple miRs. The targeted mRNA will be degraded or prevented from being translated. By the above mechanisms, miRs regulate the expression of thousands of genes and are involved in most biological processes (Ambros, V. *Nature* 431:350-355 (2004); Gangarajiu, V. K. et al. *Nat Rev Mol Cell Bio* 10:116-125 (2009); Inui, M. et al. *Nat Rev Mol Cell Bio* 11:222-263 (2010)). In addition, aberrant expression of miRs has been reported in numerous disease conditions (Esteller M., et al., *Nat Rev Genet* 12:861-874 (2011); Eacker, S. M. et al. *Nat Rev Neurosci* 10:837-841 (2009); Kong, Y. W. et al. *Lancet Oncol* 13:e249-258 (2012). Restoring the expression of various miRs has beneficial effects to certain disease conditions, and may be developed as therapeutics (Esteller M., et al. (2011); Kong, Y. W. et al. (2012)).

In other aspects of the invention, Massively Parallel Combinatorial Genetics may be used to generate vectors (e.g., viral vectors such as lentiviral vectors) comprising tandem transcriptional units that express precursor-miR, optionally along with a marker/reporter gene (e.g., GFP or RFP). A transcriptional unit herein refers to a nucleotide sequence that encodes a miR. A vector may comprise two or more of the same transcriptional units (e.g., each unit encoding the same miR, e.g., miR-124), and/or a vector may comprise two or more different transcriptional units (e.g., one or more units encoding miR-124, one or more units encoding miR-128 and/or one or more units encoding miR-132). Thus, a tandem transcription unit may contain nucleotide sequence(s) encoding miR-124, miR-128, miR-132 or any combination thereof. In some embodiments, a vector may contain two, three, four, five, six, seven, eight, nine, ten, twenty, thirty, forty, fifty (and integers between these numbers) or more of the same and/or different transcriptional units.

In some embodiments, the precursor miR of the invention comprises/is the sequence set forth as SEQ ID NO:6, SEQ ID NO:7 or SEQ ID NO:8. In some embodiments, the miR sensor of the invention comprises/is the sequence set forth as SEQ ID NO:9, SEQ ID NO:10 or SEQ ID NO:11. In some embodiments, a vector comprises a tandem precursor miR that comprises/is the sequence set forth as SEQ ID NO:1.

In some embodiments, the invention provides a genetic construct comprising at least one nucleotide sequence (e.g., one nucleotide sequence or a plurality of nucleotide sequences) that encodes a microRNA; a first compatible end element and a second compatible end element flanking the DNA element, wherein the first and second compatible end elements are capable of annealing to each other; a barcode element; a third compatible end element and a fourth compatible end element flanking the barcode element, wherein the third and fourth compatible end elements are capable of annealing to each other but are not capable of annealing to the first or second compatible end elements; and a separation site located between the fourth compatible end element and the first compatible end element, wherein the DNA element, first compatible end element and second compatible end element are on one side of the separation site, and the barcode element, third compatible end element and fourth compatible end element are on the other side of the separation site.

Also provided herein are assays and constructs for testing the efficiency and/or efficacy of vectors that comprise tandem transcriptional units that express precursor-miR. For example, in some embodiments, a vector (e.g., lentiviral vector, adenoviral vector, adeno-associated viral vector, retroviral vector) may comprise tandem transcriptional units that express precursor-miR, optionally along with a first marker/reporter gene (e.g., GFP or RFP) and a miR sensor sequence at the 3' UTR of a second marker/reporter different from the first. A miR sensor sequence herein refers to a nucleotide sequence that is complementary to a miR (i.e., a miR's complementary target sequence). A miR sensor sequence contains at least one complementary target sequence, and in some instances, may contain repeats of the complementary target sequence. For example, in some embodiments, a miR sensor sequence may contain two, three, four, five, six, seven, eight, nine, ten or more repetitive sequences complementary to the nucleotide sequence of a miR.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, particularly for the teachings referenced herein.

EXAMPLES

Example 1

Development of Barcoded Genetic Constructs

Barcoded genetic constructs were developed and manipulated to generate barcoded combinations of elements. A general schematic of a non-limiting example of a genetic construct is shown in FIG. 1A. A DNA element (e.g., DNA-1) is associated with a unique Barcode (e.g., BC-1). Flanking the DNA element are compatible ends—in this case, G2A and G2B, which can anneal to each other, as can G1A and G1B, shown in FIG. 1A as flanking BC-1. However, G1A and G2B are not compatible. In between G1B and G2A is a Separation Site that allows linearization of the construct, such as a restriction enzyme site or any other method of cleaving DNA. The minor image of this arrangement is also functional, i.e. having a barcode and compatible ends 3' to the DNA element.

FIG. 1B depicts a combination event occurring between a unique Vector and a unique Insert. The Vector is cleaved at its Separation Site. The Insert can be prepared from its Vector, for example via PCR or restriction digestion. The terminal ends of the Insert anneal to their compatible partners in the linearized Vector and are ligated.

FIG. 1C depicts the post-combination construct, which can be transformed into cells via methods known to those of ordinary skill in the art. The Barcodes BC-1 and BC-2 are now in close proximity and can easily be read by sequencing, revealing the identity of the DNA elements. Furthermore, the separation site is retained, allowing facile construction of high-order combinations.

In a non-limiting embodiment of a sample generation scheme, a library of constructs as in FIG. 1A is prepared on plasmids for each unique DNA element through high-throughput robotics. This plasmid library is pooled (generating the Vector library), and PCR is performed on the pool (generating the Insert library). In a one-pot reaction, all Vectors are paired with all Inserts, generating the full combinatorial set of pairwise combinations. This Pairwise library is then further reacted with the same Insert library to generate a Tri-wise library, Quad-wise library, and so forth, arising from a single Vector library.

The proximity of the unique barcodes in the Combinatorial library allows rapid identification of the DNA elements present within a single combinatorial construct via sequencing, microarrays, or other methods of determining DNA sequence. In one example, a pool of cells containing the combinatorial library undergoes selection for a specific phenotype (such as chemotherapy resistance); subsequent isolation and sequencing of the surviving cells elucidates which combination of DNA elements yielded the desired phenotype. In another example, the pooled cells undergo high-throughput next-generation sequencing, yielding the prevalence of specific DNA combinations within the pool; this data can then be used to generate a protein interaction network.

Example 2

Gibson Assembly Conception

In some non-limiting embodiments of the invention, the Gibson assembly method is used to generate compatible end elements. The Gibson reaction employs T5 exonuclease to digest the 5' strand, allowing complementary sequences to anneal, gaps to be filled with DNA Polymerase, and the constructs ligated by Taq ligase (Gibson et al. (2009) *Nature Methods* 6:343-5). As depicted in FIG. 1, G1A and G1B are identical sequences; G2A and G2B are likewise identical. The separation site is a restriction enzyme recognition site.

In some embodiments, a single restriction site is used to generate the linearized vector for reaction, thus avoiding interference with DNA elements. As such, this methodology is especially useful for interrogating combinations of genome-wide elements such as ORFs and noncoding DNA.

Example 3

Demonstration of Massively Parallel Combinatorial Genetics in *E. coli*

Methods for Massively Parallel Combinatorial Genetics were successfully applied in *E. coli* to two fluorescent proteins—GFP and mCherry. The total DNA element for each consisted of an inducible promoter, the protein ORF, and a terminator. These elements were barcoded as BC1-GFP and BC2-mCherry, respectively.

Figure 2:
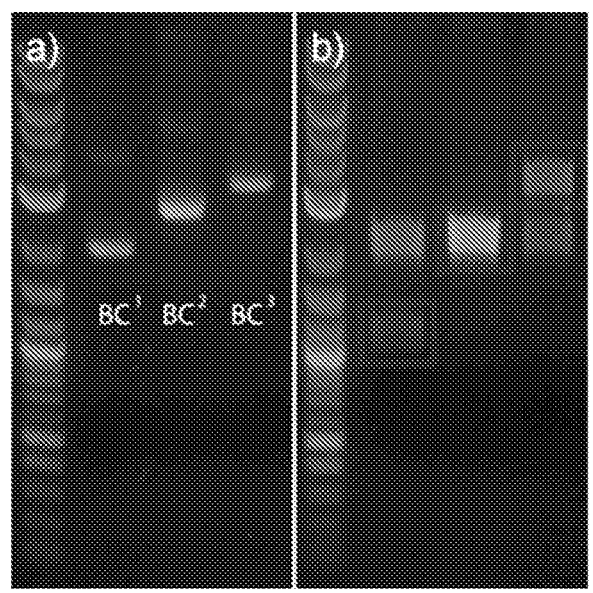
FIG. 2 demonstrates combinations of a single unique element with itself.

In the first demonstration, BC1-GFP was inserted into itself twice in succession to generate BC1-BC1-GFP-GFP and BC1-BC1-BC1-GFP-GFP-GFP. FIG. 2A shows gel electrophoresis of the uncut plasmid itself, with each successive integration of a barcoded-GFP unit adding another ~1 kb to the size of the plasmid. The plasmid was also restriction digested at points on the plasmid separating the changing combinatorial region from the static region on the plasmid. In FIG. 2B, boxes are drawn surrounding the digested insert, showing an increase in ~1 kb per successive insertion, while the unmarked static region remains the same size.

Figure 3:
FIG. 3 depicts combination and functional expression of mCherry and GFP constructs. Fluorescent images are depicted using filters for mCherry (FIG. 3A), GFP (FIG. 3B), and overlaid (FIG. 3C).

Next, a combinatorial set was created using constructs for both GFP and mCherry. Fluorescence microscopy showed the successful combination of DNA elements and functional protein expression (FIG. 3). FIG. 3 depicts combination and functional expression of mCherry and GFP constructs. Fluorescent images are depicted using filters for mCherry (FIG. 3A), GFP (FIG. 3B), and overlaid (FIG. 3C). Clones showing only GFP expression or only mCherry expression were also identified.

Figure 4:
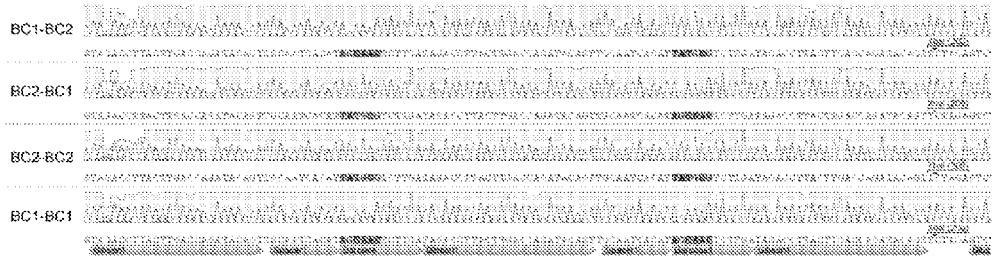
FIG. 4 depicts sequencing results and alignment of four clones from a combinatorial reaction. Sequence annotations are shown at the bottom and correspond, from top to bottom, to SEQ ID NOs: 12-15. Darkly shaded sequences represent unique portions of the barcode. All four possible permutations of two barcoded constructs were recovered, along with preservation of the XbaI Separation Site on the right.

Through sequencing, the full combinatorial spaces of four combinations with intact Barcodes and Separation Sites were also confirmed, indicating the robustness of the method (FIG. 4). Thus, this demonstrates the ability of methods developed herein to i) generate combinatorial sets of unique barcoded DNA elements, ii) enable identification of combinations via sequencing of barcoded regions, and iii) generate higher-order combinations using the same barcoded construct for each combination step.

Example 4

Restriction Site Conception

In some non-limiting embodiments of the technology, restriction site methodology can be applied to generate compatible end elements (FIG. 5). Similar to the BioBrick® standard, two unique restriction enzymes generate compatible overhangs that when ligated together form a scar that is not recognized by either restriction enzyme and cannot be further cleaved (Anderson et al. (2010) *Journal of Biological Engineering* 4:1). The shorter scar associated with this approach, relative to the Gibson assembly method, allows for a higher number of barcode elements to be read within a standard next-generation sequencing read, therefore allowing higher-order combinations. While the use of additional restriction enzymes raises the chance of interference with the inserted DNA elements, the specific restriction enzymes to be used can be modified to any set of DNA elements, such that the restriction enzymes necessary for this method interfere with the fewest number of elements. Furthermore, mutagenesis can be performed on the DNA elements to remove restriction sites from their sequences.

Using the restriction site assembly strategy, the facility of generating higher-order combinations was tested. Using a library of five barcoded DNA elements, the combination sequence was iterated three times to generate pairwise, three-wise, and four-wise combinations. Sequencing individual colonies showed the retention of barcodes and scars in an easily readable fashion (FIG. 6A). Plasmids isolated from colonies were then digested to separate the variable combinatorial region, which consists of the barcodes and their respective DNA elements, from the constant remainder of the vector (FIG. 6B).

Example 5

Library Generation

Next, to test gene expression, a barcoded vector library of GFP and mCherry was constructed under the control of aTc-inducible pLtetO promoters with a T1+T7 fusion terminator downstream of each ORF. Each vector contained the high-copy ColE1 origin, tetR under control of a constitutive promoter, and cat conferring chloramphenicol resistance.

Figure 7:
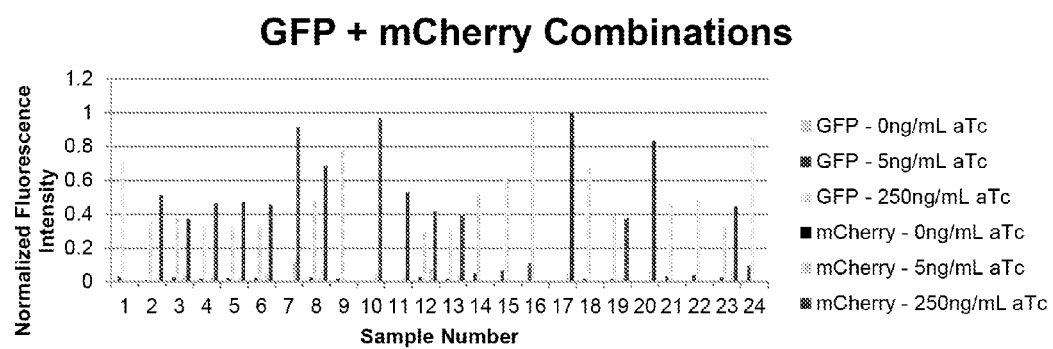
FIG. 7 depicts quantitative assessment of GFP and mCherry combinations via restriction site assembly. Samples #1-24 are colonies isolated from the transformation of the combinatorial library into E. coli DH5a cells. GFP-GFP combinations are represented by samples #1, 8, 14, 15, 16, 18, 21, 22, and 24; mCherry-mCherry combinations by #7, 10, 11, 17, 20; GFP & mCherry combinations by #2-6, 8, 12, 13, 19, 23.

An insert library was generated via PCR, creating a pair-wise combinatorial set as in FIG. 5 that was then transformed into DH5a cells. Twenty-four colonies were isolated and grown in increasing concentrations of aTc along with positive and negative controls (FIG. 7). Significantly, the data show several features: i) an even, distribution of the three possible combinations that does not achieve significance via chi-squared testing (24 total samples; 9 GFP-GFP; 5 mCherry-mCherry; 10 GFP and mCherry); ii) near-independent expression of each separate promoter-ORF combination, as determined by comparison between GFP-mCherry combinations such as N95-2 and mCherry-GFP combinations such as N95-3; and iii) a high degree of repression and induction control, yielding on/off ratios of 150-300x.

Example 6

Investigation of Antibacterial Resistance in *E. coli*

Antibacterial resistance and methods to defeat resistance were investigated in *E. coli*. By barcoding 173 documented transcription factors in *E. coli*, pairwise and tri-wise combinations were generated, and the combinations that most effectively decrease or increase antibiotic resistance were determined. Statistical analysis of the sequencing reads identified nonlinear epistatic genetic interactions, such as synergy and antagonism. These results were then validated in antibiotic susceptibility testing. To demonstrate the full power of this technology, the most successful pairwise combinations were then used to generate tri-wise combinations and susceptibility assessed again. Multiple mechanisms of resistance can be investigated using the methods provided herein, including extended-spectrum betalactamases, efflux pump mutants, and metallo-betalactamases, in response to a range of antibiotics.

Figure 16:
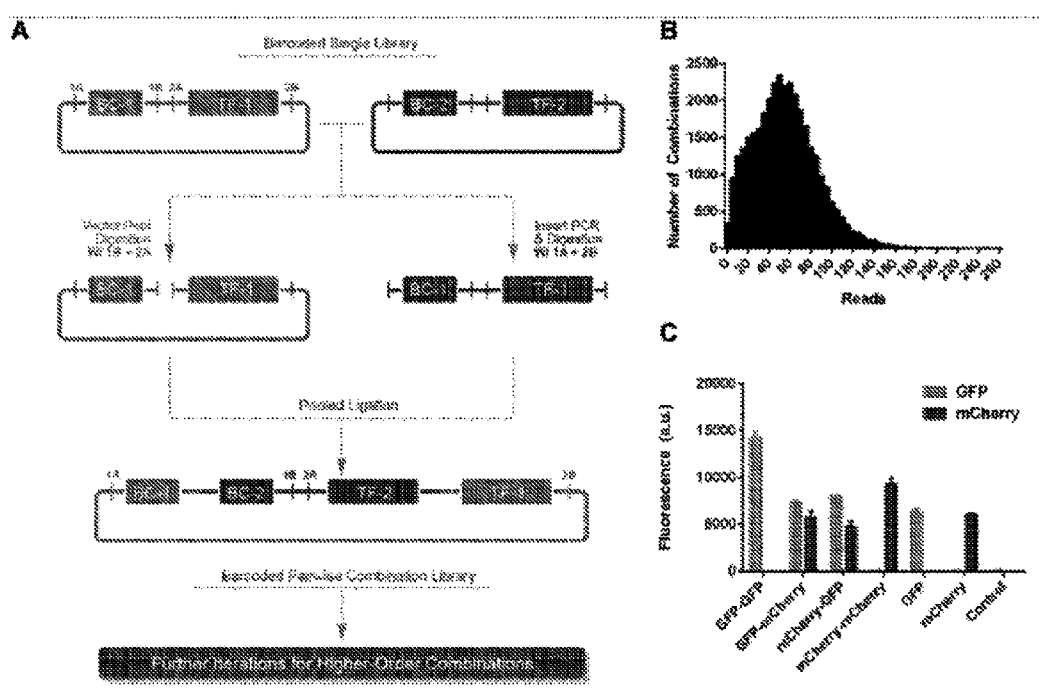
FIG. 16A depicts a non-limiting embodiment of a Massively Parallel Combinatorial Genetics assembly strategy. Transcription factor (TF) expression constructs are barcoded (BC), and four restriction sites (1A, 1B, 2A, 2B) are positioned as shown. The pairs, 1A/1B and 2A/2B, are unique restriction sites that generate compatible overhangs within one pair but are incompatible with the other pair. The barcoded vectors are pooled and digested with enzymes 1B+2A. Inserts are generated from vectors by PCR and digested with 1A+2B.
FIG. 16B depicts distribution of high-throughput sequencing reads among combinations in the pairwise library.
FIG. 16C depicts expression of a Massively Parallel Combinatorial Genetics constructs. All four pairwise combinations of GFP and mCherry constructs and single GFP and mCherry constructs were induced with aTc at 250 ng/mL and assessed by flow cytometry.

Massively Parallel Combinatorial Genetics uses an iterative cloning strategy beginning with a library of barcoded DNA elements (FIG. 16A). Restriction digests of pooled vector and insert libraries, followed by a one-pot ligation reaction, create a library of pairwise combinations with the barcodes in close proximity to one another. As a result, the identities of the components in a particular construct can be determined by a short sequence reading the barcodes in order. High-throughput sequencing can census the distribution of library members within a pooled population and identify changes in the population under different experimental conditions. Alternatively, Sanger sequencing may be performed on isolated colonies selected through plating assays or cell sorting. Notably, the methods provided herein are iterative methods that can use the newly produced combinatorial library and the same insert pool to generate higher order combinations in log-linear time.

FIG. 16A shows an outline of the assembly method. Transcription Factor (TF) expression constructs are barcoded (BC) and four restriction sites (1A, 1B, 2A, 2B) are positioned as shown. The pairs, 1A/1B and 2A/2B, are unique restriction sites that generate compatible overhangs within the pair but are incompatible with the other pair. The barcoded vectors are pooled and digested with enzymes 1B+2A. Inserts are generated from vectors by PCR and digested with 1A+2B. A one-pot ligation reaction produces a pairwise combinatorial library, which can be further digested and ligated with the same insert pool to produce higher-order combinations.

Figure 17:
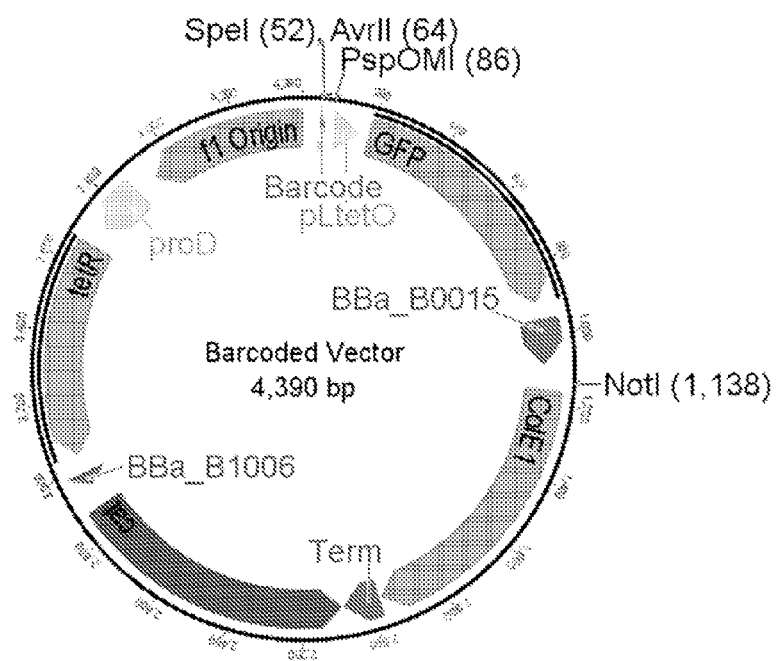
FIG. 17 depicts a plasmid map showing a single gene expression construct (GFP) barcoded and flanked by restriction sites for Massively Parallel Combinatorial Genetics library assembly.
Figure 24:
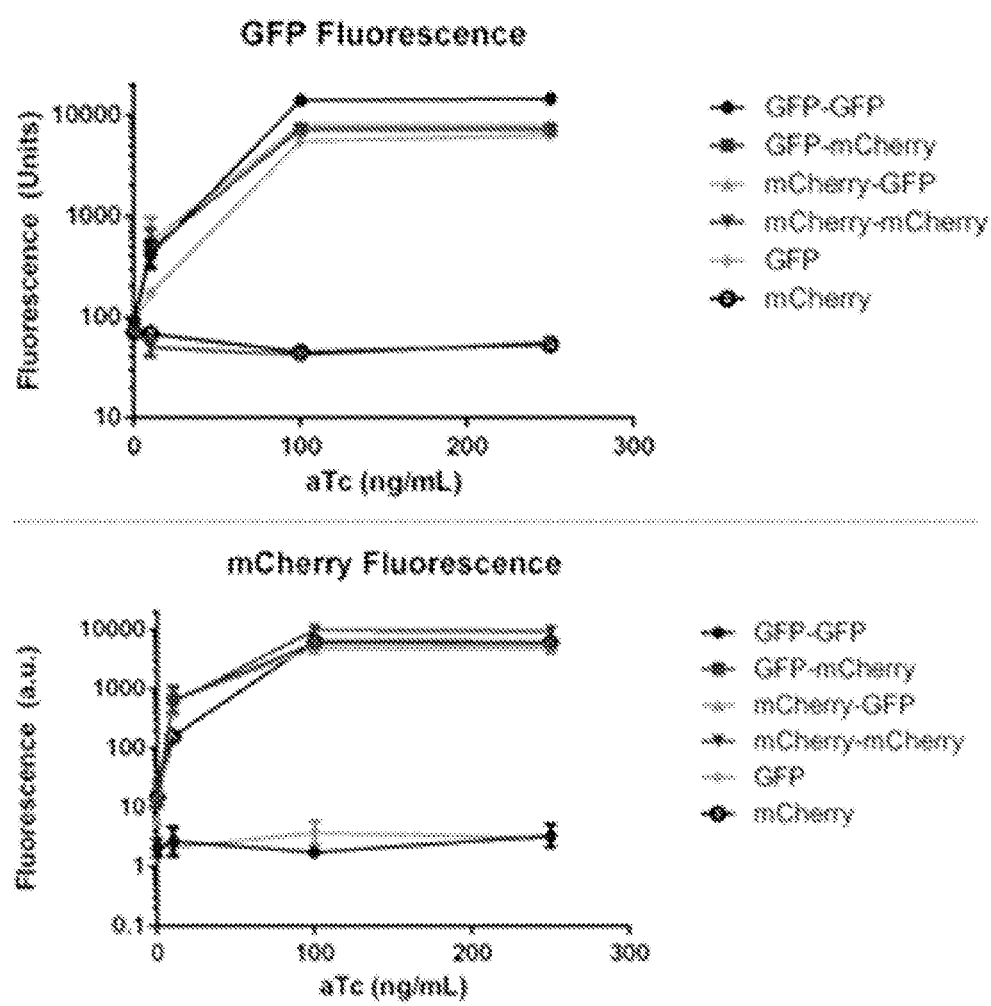
FIG. 24 depicts graphs of fluorescent induction curves.

In this study, 173 E. coli transcription factors (TFs) and 18 fluorescent proteins were placed under control of the aTc-inducible pLtetO promoter (FIG. 17). These expression constructs were uniquely barcoded and combined to yield all possible 35,343 pairwise combinations (some open reading frames (ORFs) were rejected as vectors or inserts due to cleavage by restriction enzymes). This pairwise combinatorial library was transformed into an E. coli MG1655 strain and sequenced on the Illumina HiSeq™ platform, showing an even distribution of combinations across the population and recovery of 34,554 combinations, or 98% of all possible combinations (FIG. 16B). To assess expression levels of the construct and the influence of order on expression levels, fluorescence of all four pairwise combinations of GFP and mCherry was measured as well as single GFP and mCherry (FIG. 24). All four pairwise combinations of GFP and mCherry and single GFP and mCherry were induced with aTc at 250 ng/mL and assessed by flow cytometry. GFP-mCherry and mCherry-GFP showed comparable levels of fluorescence, indicating low influence of sequence on expression level. GFP-GFP and mCherry-mCherry showed approximately double expression levels of GFP and mCherry, respectively, compared to heterogeneous combinations and single constructs (FIG. 16C).

Transcription factor (TF) combinations in the combinatorial library were discovered, leading to viability phenotypes for the New Delhi metallo-betalactamase 1 (NDM-1) E. coli strain. The recently discovered NDM-1 enzyme hydrolyzes a wide spectrum of beta-lactam antibiotics, including carbapenems (Mochon, A. B. et al. (2011) Journal of clinical microbiology 49:1667-1670). This resistance to antibiotics commonly used in treatment causes recalcitrant infections that are treatable only with a handful of drugs of last resort. This study, therefore, sought primarily to identify transcription factor combinations that could potentiate existing antibiotics for treatment.

Figure 18:
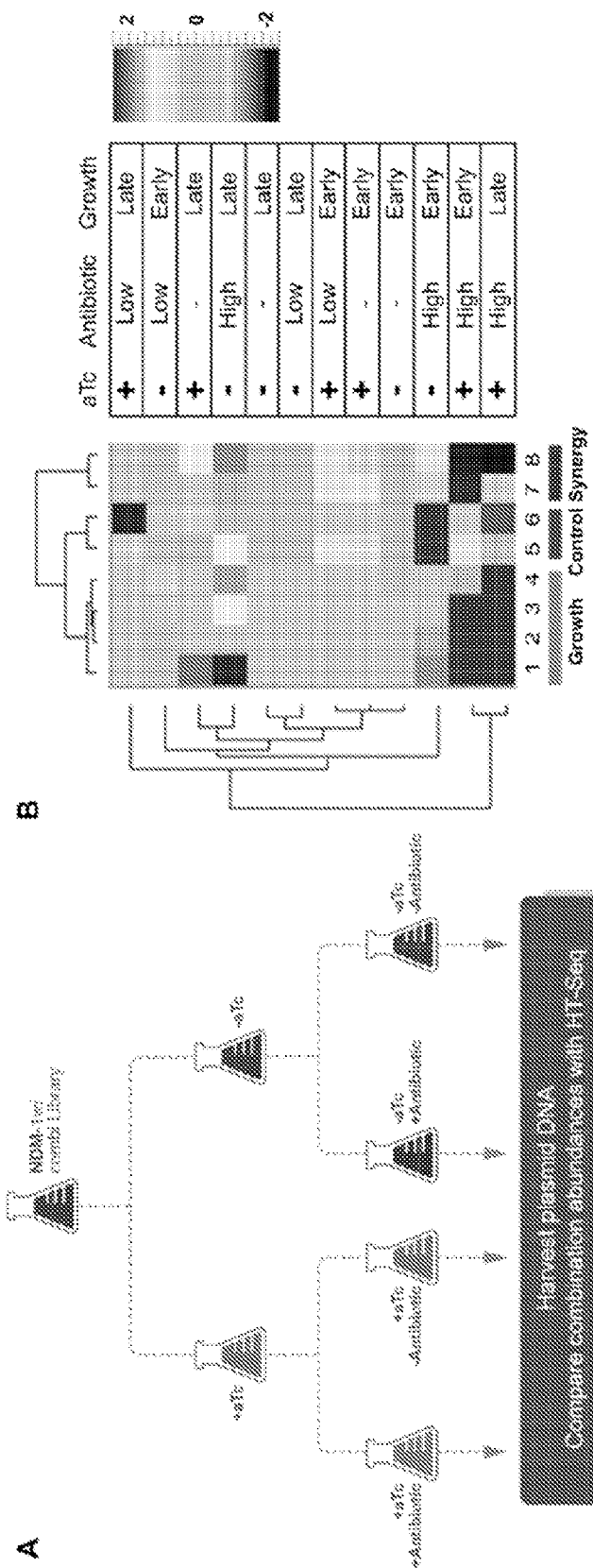
FIG. 18A depicts a non-limiting embodiment of a Massively Parallel Combinatorial Genetics method. E. coli NDM-1 cells containing a Massively Parallel Combinatorial Genetics library are diluted into cultures with and without aTc and grown to mid-log. Each culture is then further diluted into cultures with and without antibiotic and with and without aTc. DNA from each condition is harvested at early log and late log growth stages and processed for high-throughput sequencing. Comparisons of combination abundances among different conditions reveal genotypes leading to desired phenotypes.
FIG. 18B depicts a "hit" overview heat map. Hierarchical clustering of combination S-scores across experiments shows profiles of different phenotypes. Area marked synergy shows combinations that drop out upon addition of both ceftriaxone and aTc. The opposite, growth, shows combinations that are relatively overrepresented upon addition of both ceftriaxone and aTc.

The combinatorial library was transformed into an E. coli NDM-1 strain that was produced by conjugation of an E. coli MG1655 strain with a clinical isolate of Klebsiella pneumoniae NDM-1. The broad-spectrum resistance of the E. coli NDM-1 strain was verified across a range of antibiotics, and it was found that its resistance profile resembled that of the original Klebsiella pneumonia isolate (Table 2). To identify combinations that potentiated antibiotic killing, the transformed NDM-1 strain was subjected to conditions with and without aTc induction and ceftriaxone treatment (FIG. 18A). Ceftriaxone is a third-generation cephalosporin with broad spectrum activity and is used clinically to treat pneumonia, bacterial meningitis, and gonorrhea. Populations under each condition were harvested at specified growth stages to observe the shifting distributions of the population over time. These samples were multiplexed for high-throughput sequencing on the Illumina HiSeq platform.

TABLE 2

| E. coli NDM-1 Antibiotic Resistance Profile, NDM-1 MICs (µg/mL) | | |
|---|---|---|
| Antibiotic | Tested | Previously Reported[6] |
| Amoxicillin | >512 | |
| Ceftriaxone | >128 | >32 |
| Colistin | <0.125 | 0.25 |
| Gentamicin | >256 | >10 |
| Imipenem | >32 | 8 |
| Piperacillin-Tazobactam | >256 piperacillin, 32 tazobactam | >128 |

Figure 19:
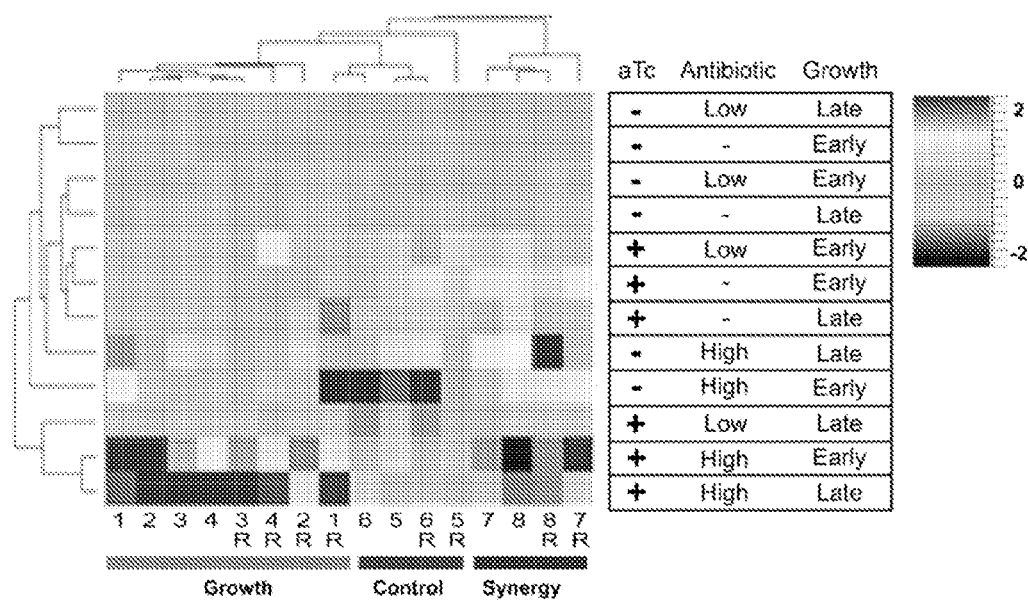
FIG. 19 depicts hierarchical clustering of gene combinations and reciprocals. Numbers 1-8 denote gene pairs corresponding to those in FIG. 18B. R denotes the reciprocal arrangement of the gene pair. Gene pairs conferring the same phenotype and their reciprocals cluster together.

To determine the influence of each combination on NDM-1 viability, the abundance of each combination in a particular experimental condition was compared against its abundance in other experiments. For example, combinations that were especially overrepresented in the presence of both aTc and ceftriaxone, compared to aTc alone and ceftriaxone alone, suggested that the combination conferred a relative growth advantage to the cell. Likewise, combinations that were under-represented in both aTc and ceftriaxone conferred bactericidal synergy with ceftriaxone. Combinations leading to phenotypes of synergistic killing, neutral growth, and advantageous growth were selected. Hierarchical clustering on the combinations and their scores in each experiment showed clustering by phenotype class (FIG. 18B). To gauge the influence of gene order in the expression construct, hierarchical clustering was also performed on these combinations and their reciprocal configurations. The combinations of the same phenotype clustered together regardless of order (FIG. 19).

Figure 20:
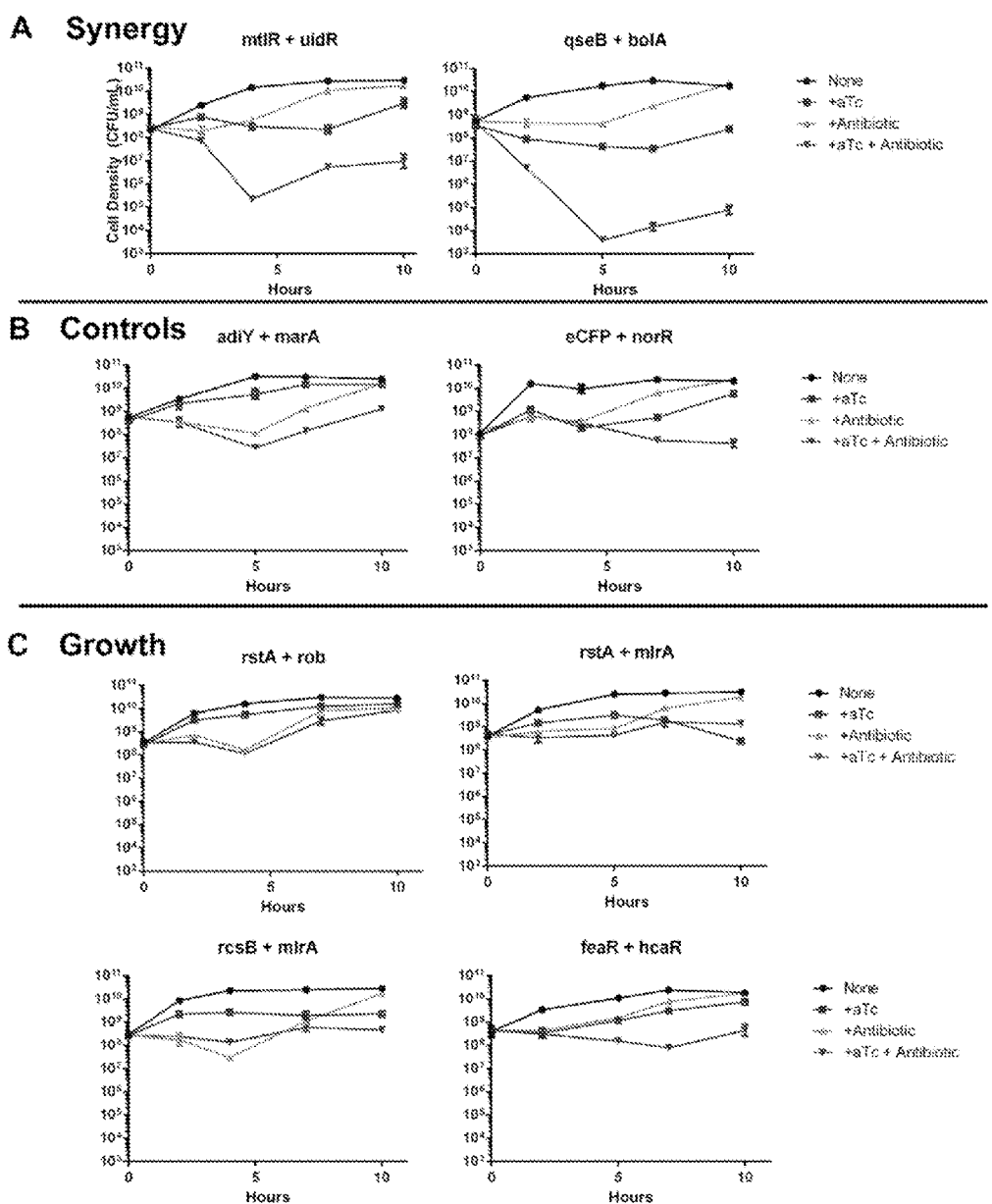
FIG. 20A depicts graphs showing synergy for NDM-1 antibiotic susceptibility phenotypes. NDM-1 antibiotic susceptibility phenotypes.
FIG. 20B depicts graphs showing controls for NDM-1 antibiotic susceptibility phenotypes. Combinations show minor potentiation of ceftriaxone. The onset of action of eCFP+norR is delayed compared to adiY+marA.
FIG. 20C depicts graphs showing growth advantage for NDM-1 antibiotic susceptibility phenotypes. Combinations show minimal effect upon induction throughout the course of the experiment.

Each gene pair was cloned and its activity validated in antibiotic susceptibility assays. Combinations identified as synergistic showed a significant amplification of killing by three to four orders of magnitude compared to antibiotic alone or aTc alone (FIG. 20A), and significantly greater amplification than controls (FIG. 20B). By contrast, combinations identified as advantageous showed minimal amplification of killing by antibiotic alone (FIG. 20C). Although the advantageous combinations did not confer additional survival beyond antibiotic alone, the innocuous expression of the gene pairs led to high abundances in the library experiments compared to synergistic and control combinations.

Figure 21:
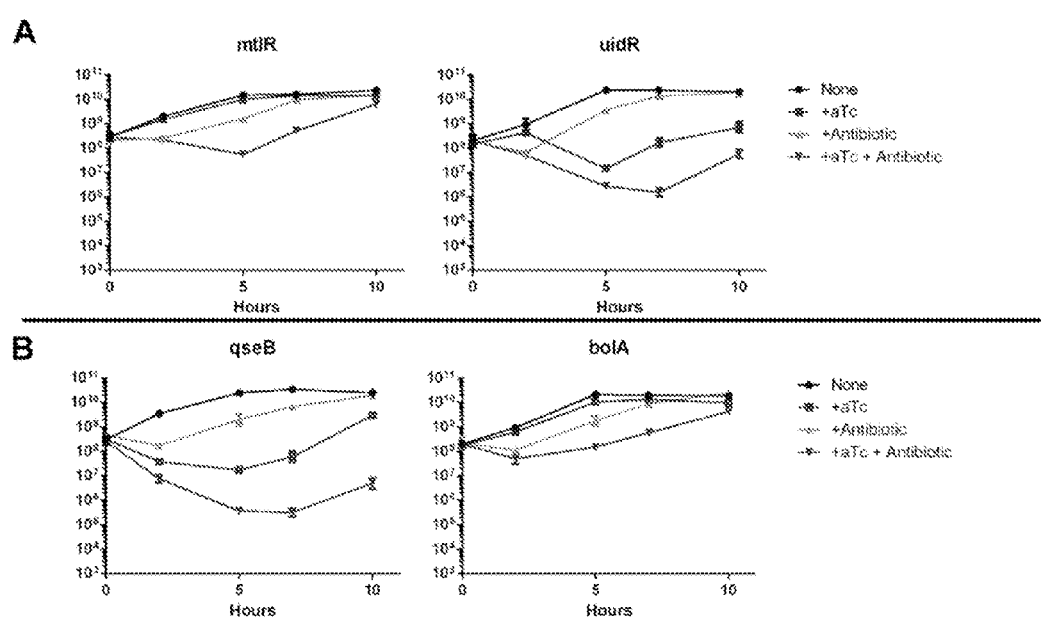
FIGS. 21A and 21B depict graphs showing antibiotic susceptibility of individual genes.

By enabling high-throughput screening of combinatorial libraries, Massively Parallel Combinatorial Genetics enables discovery of unexpected synergy between seemingly unrelated proteins. The synergistic combination mtlR and uidR regulate mannitol and β-glucoside metabolism, respectively. Each gene individually has not been reported to mediate antibiotic resistance and showed minimal effect in antibiotic susceptibility assays (FIG. 21A). Similarly, qseB and bolA are implicated in pathways associated with virulence and stress response, respectively, and showed significantly lower activity as individual genes compared to pairwise combinations (FIG. 21B).

Figure 22:
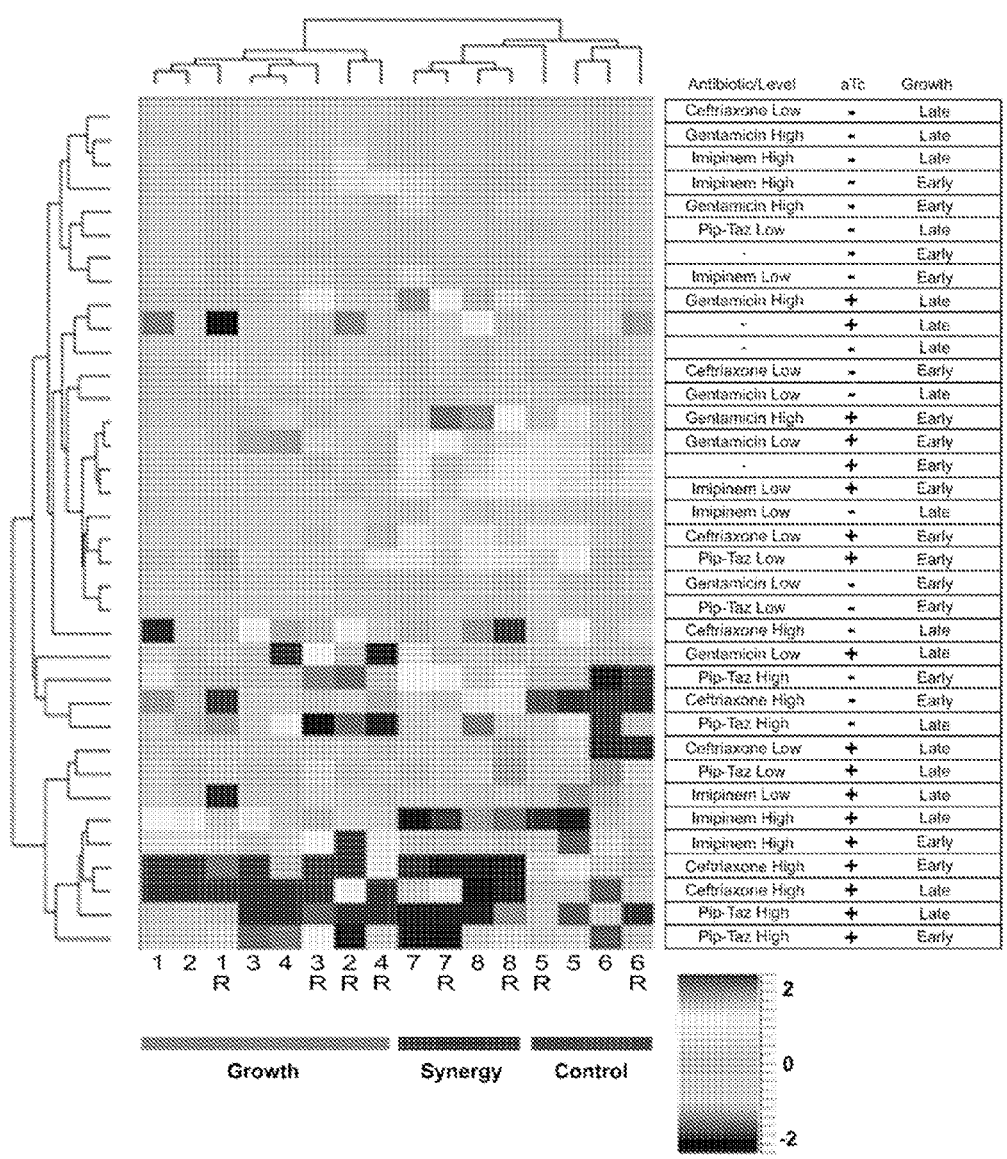
FIG. 22 depicts hierarchical clustering across the antibiotics ceftriaxone, imipenem, piperacillin-tazobactam and gentamicin. High-treatment of beta-lactams cluster together, separately from gentamicin.
Figure 25:
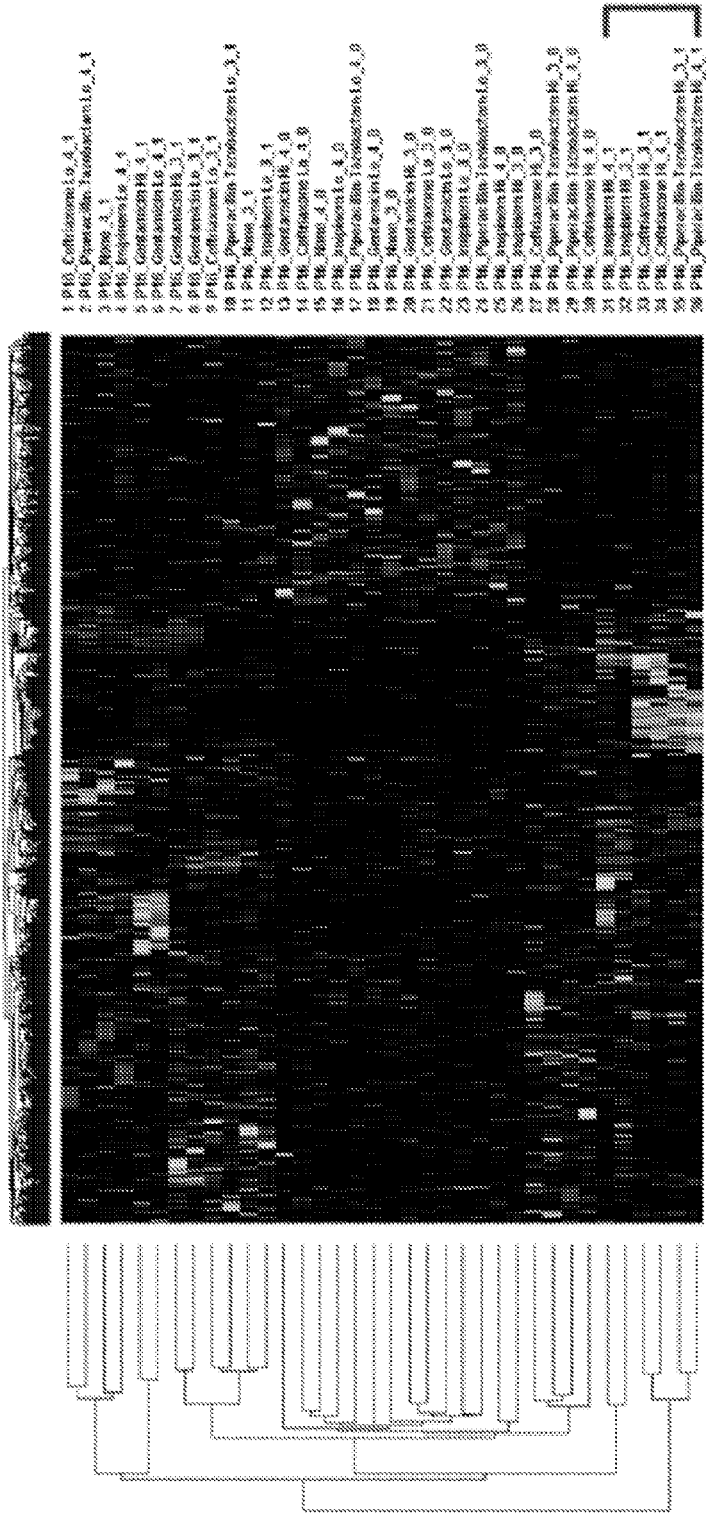
FIG. 25 depicts hierarchical clustering of top hits across all antibiotic-aTc conditions. 6311 gene pairs show at least one S-score above 2.4 or below −2.4, where 2.4 is three times the standard deviation of the S-score population distribution. Euclidean correlation with average linkage has been employed in clustering analysis. Hits for the beta-lactams imipenem, ceftriaxone, and piperacillin-tazobactam in the presence of aTc cluster together (red bracket), separately from gentamicin.

To study whether Massively Parallel Combinatorial Genetics can identify combinations across a range of antibiotics, the combinatorial library was exposed to the beta-lactam antibiotics imipenem and piperacillin-tazobactam, and to the aminoglycoside antibiotic, gentamicin. Along with ceftriaxone, each antibiotic is used widely in clinical scenarios and is degraded by the NDM-1 strain. Interestingly, the beta-lactam antibiotics clustered together separately from gentamicin, possibly because of their distinct mechanisms of action (FIGS. 22, 25). Massively Parallel Combinatorial Genetics is therefore able to distinguish nuances of experimental treatments.

Figure 23:
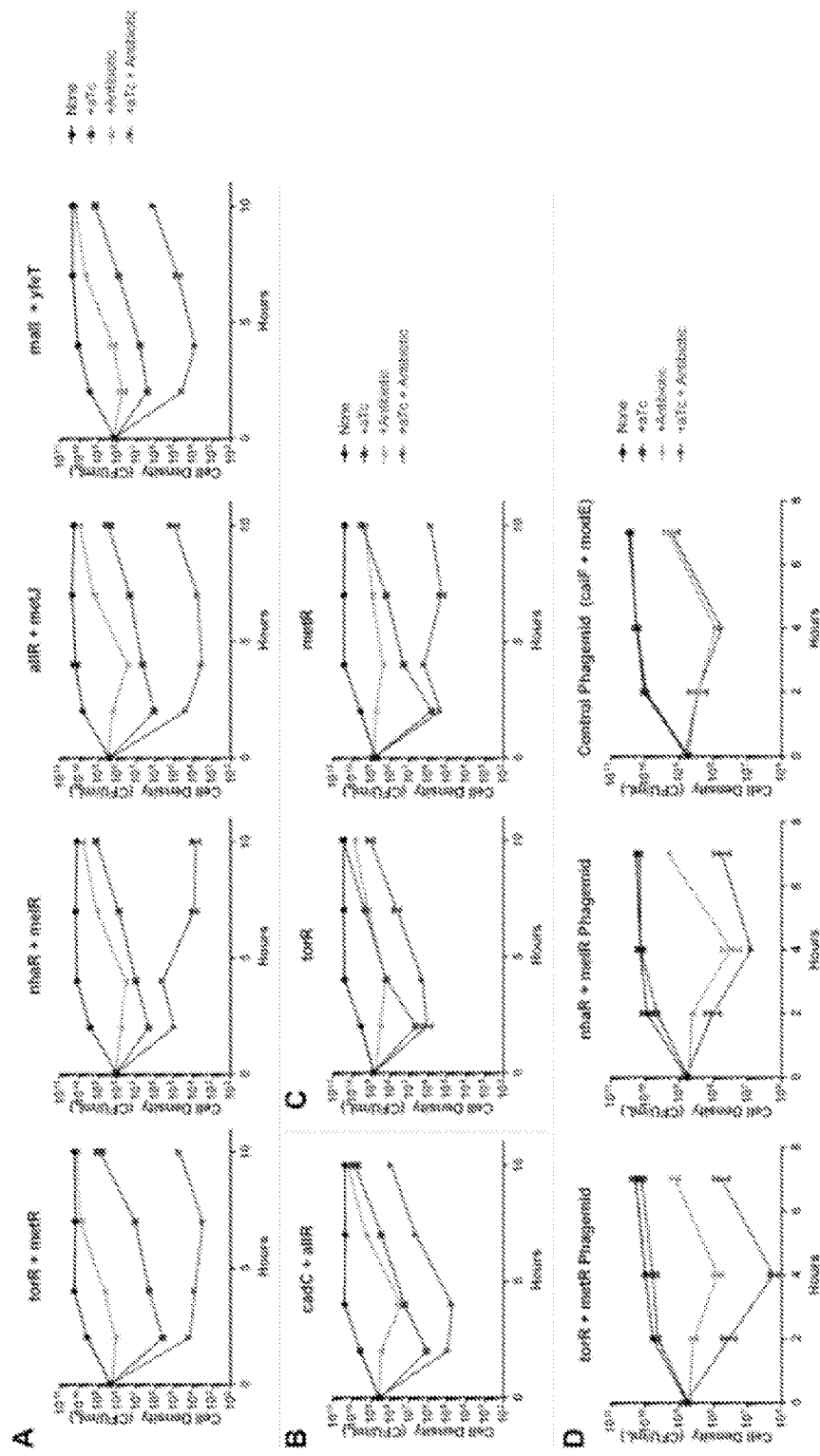
FIG. 23A depicts graphs showing that combinations potentiate antibiotic lethality by 4-6 orders of magnitude when induced and suppress growth for over 10 hours.
FIG. 23B depicts graphs showing that random lethal combinations such as cadC+allR show significantly less potent amplification of ceftriaxone and less sustained growth suppression over time.
FIG. 23C depicts graphs showing that torR and metR individually show significantly weaker amplification of ceftriaxone compared to the combination torR+metR.
FIG. 23D depicts graphs showing that phagemids containing torR+metR and nhaR+melR infecting NDM1 cells show amplified killing of cultures with ceftriaxone and induction.

To determine whether Massively Parallel Combinatorial Genetics can identify lethal combinations amplifying the bactericidal activity of antibiotics, combinations with reduced abundance in presence of aTc and aTc plus ceftriaxone were selected. Combinations that showed over 5 orders of magnitude greater killing of the bacterial population compared to ceftriaxone alone were discovered (FIG. 23A). Because many genes are toxic, random combinations of toxic genes were constructed to assess whether Massively Parallel Combinatorial Genetics can identify especially lethal combinations. Identified combinations showed an average of an order of magnitude greater killing at the point of lowest cell density (FIG. 23B). Furthermore, the combinations showed longer sustained killing over a period of 10 hours.

This study also assessed whether the large killing effect resulted from synergy between its two constituent genes. While torR and metR are toxic when expressed individually, the summation of their activities did not fully recapitulate the activity of the combination, suggesting a synergy between their effects (FIG. 23C). Massively parallel combinatorial genetics can therefore isolate combinatorial perturbations leading to strong phenotypes that are not ex ante apparent from the combination's individual constituents.

Toxic gene combinations could be effective adjuvants for antibiotic treatment if delivered, for example, by phage. Combination constructs were packaged in phagemids and an $E.$ $coli$ EMG2 strain conjugated with a clinical isolate of $Klebsiella$ $pneumoniae$ NDM-1 was infected. Induction of genes in conjunction with ceftriaxone led to greater killing of one to two orders of magnitude compared to ceftriaxone alone, whereas a control phagemid showed no improvement (FIG. 23D).

Figure 26:
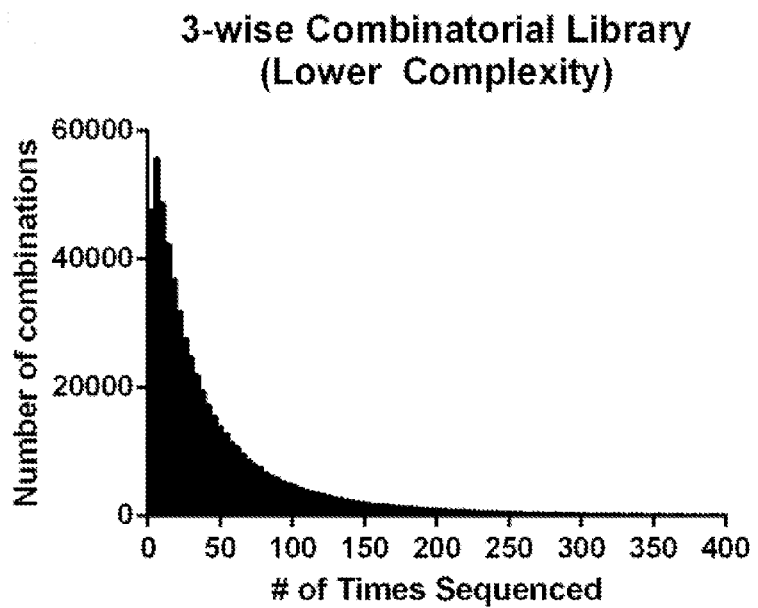
FIG. 26 depicts a graph showing a lower complexity tri-wise combinatorial library combining 189×187×18 genes. Out of 636174 possible combinations, 582,433 unique combinations (92% of all possible combinations) were recovered from approximately 30 million sequencing reads.
Figure 27:
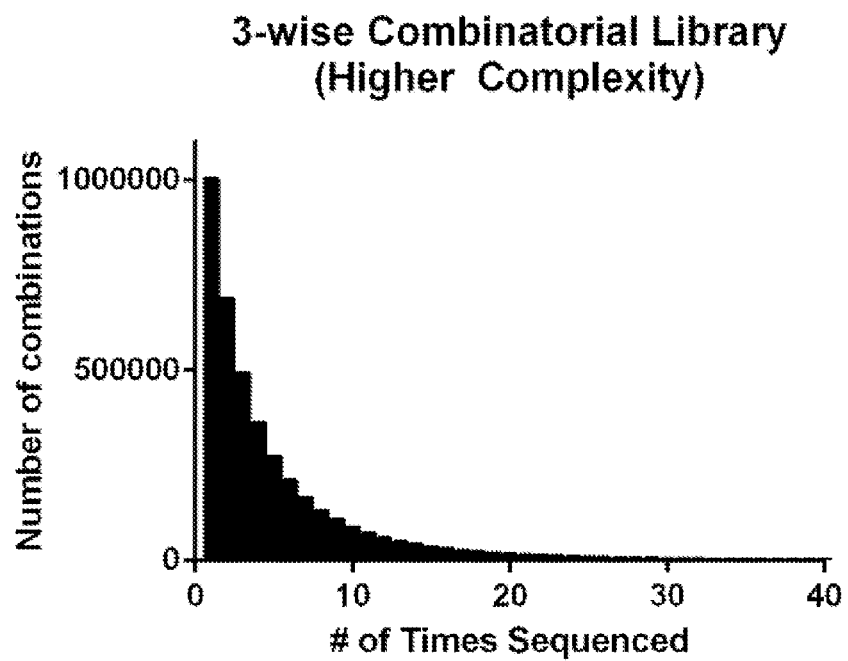
FIG. 27 depicts a graph showing a higher complexity tri-wise combinatorial library combining 189×187×187 genes. Out of 6,609,141 possible gene combinations, 4,042,316 combinations (61%) were recovered from approximately 20 million sequencing reads.

To demonstrate ready scalability of the Massively Parallel Combinatorial Genetics method to higher-order combinations, tri-wise combination libraries were constructed from the pairwise TF library. A lower complexity library was produced by combining 189×187×18 genes (FIG. 26). Out of 636,174 possible combinations, 516,798 unique combinations (81% of all possible combinations) were recovered from approximately 17 million sequencing reads. A higher complexity library was also produced by combining 189×187×187 genes (FIG. 27). Out of 6,609,141 possible gene combinations, 4,042,316 combinations (61%) were recovered from approximately 20 million sequencing reads. Greater coverage of the library can likely be achieved through additional electroporations and dedicating a greater number of reads to the sample.

Through Massively Parallel Combinatorial Genetics, gene combinations conferring strong phenotypes in antibiotic resistance were reliably identified. High-throughput sequencing applied to the library assembly strategy enabled censusing of pooled combinatorial populations at an unprecedented scale. The methods provided herein are flexible and can build high-order combinations of any DNA element of choice, including gene expression and knockdown constructs, synthetic circuit components, and genomic sequences. Massively parallel combinatorial genetics could be used to generate complex interactome datasets, screen for combinatorial inducers of desired phenotypes such as differentiation, and characterize synthetic circuits at unprecedented scale and efficiency. Massively parallel combinatorial genetics using restriction enzymes may also be adapted to Gibson isothermal assembly or recombinases in situations where the library is incompatible with restriction sites. Probing complex phenotypes and emergent network properties will greatly contribute to the understanding of biological systems and their applications.

Methods

Bacterial Strains and Culture Conditions.

$E.$ $coli$ DH5a cells used for cloning were obtained from New England Biolabs. $E.$ $coli$ ElectroTen-Blue cells used for library electroporation were obtained from Agilent. $E.$ $coli$ MG1655 cells conjugated with a clinical isolate of $K.$ $pneumonia$ producing NDM-1 were used for antibiotic susceptibility and persistence assays. Cultures grew in Luria-Bertoni (LB) broth with these chemical concentrations unless otherwise noted: aTc at 100 ng/μL, carbenicillin (Carb) at 50 μg/mL, chloramphenicol (Cm) at 30 μg/mL, ceftriaxone at 192 μg/mL.

Chemicals.

T4 DNA ligase, T5 exonuclease, and restriction enzymes were obtained from New England Biolabs. Polymerase chain reactions were performed with HiFi™ HotStart from Kapa Biosystems. Oligonucleotides were purchased from Integrated DNA Technologies. Antibiotics were purchased from Sigma and Enzo Life Sciences. All other chemicals were purchased from Sigma-Aldrich.

Library Construction.

To build the barcoded single-transcription factor (TF) library, Gibson isothermal assembly was used to ligate a unique 6-base pair barcode with the $P_L$tetO promoter, the TF open reading frame (ORF), and the vector backbone. Each barcode was 6 base pairs in length and separated by every other barcode by a genetic distance of at least 2 bases. Transcription factor ORF sequences were obtained from the ASKA Clone(-) library from NBRP-$E.$ $coli$ at NIG. All TF expression constructs were followed by terminator BBa_B1006 from the Registry of Standard Biological Parts. Each barcoded TF contained restriction sites in this configuration: SpeI-Barcode-AvrII-PspOMI-TF expression construct-NotI. Inserts were generated from each vector by PCR with two common primers.

To construct the pairwise combinatorial library, all vectors and inserts were measured for concentration on NanoDrop 2000 (Thermo Scientific) and pooled in equimolar amounts to form a vector pool and an insert pool. The vector pool was digested with AvrII and PspOMi, and the insert pool was digested with SpeI and NotI. Both digests were then purified through phenol/chloroform extraction and ethanol precipitation. The digest pools were ligated with T4 DNA ligase, purified with phenol/chloroform and ethanol precipitation, and electroporated into ElectroTen-Blue cells per manufacturer's protocol. A total of 3,000,000 transformants were obtained and grown to mid-log in 100 mL of LB+30 μg/mL chloramphenicol. Plasmids were isolated through Midi Prep (Qiagen) and electroporated into E. coli NDM-1.

Antibiotic Treatments.

Antibiotic assays were performed at 37° C. in a 96-well clear-bottom plate on a VersaMax™ Microplate Reader and shaker (Molecular Devices). All culture wells held 200 μL. Frozen stocks of NDM-1 with library were diluted into LB with or without 100 ng/μL aTc. When these cultures reached an OD600=0.6, they were diluted 1:100 into wells with or without antibiotic and with or without 100 ng/μL aTc. Antibiotic concentrations used were: ceftriaxone low: 64 μg/mL; ceftriaxone high: 256 μg/mL; imipenem low: 32 μg/mL; imipenem high: 96 μg/mL; piperacillin-tazobactam low: 64 μg/mL piperacillin, 8 μg/mL tazobactam; piperacillin-tazobactam high: 256 μg/mL piperacillin, 32 μg/mL tazobactam; gentamicin low: 32 μg/mL; gentamicin high: 256 μg/mL. These wells were grown until OD=0.3 or 0.9. All DNA from wells was harvested by alkaline lysis and ethanol precipitation. Each miniprep sample was assayed for concentration using SYBR® Fast qPCR kits (Kapa Bio systems).

High Throughput Sequencing.

Each sample was prepared for Illumina HiSeq™ sequencing by adding an indexing barcode and Illumina anchor sequences through polymerase chain reaction (PCR). To prevent PCR bias that would skew the population distribution, PCR reactions were terminated during exponential phase. PCR products were purified with AMPure XP beads (Agencourt®), concentration quantified via qPCR, and pooled in equimolar amounts. Multiplexed samples were then sequenced using the primers indicated below.

Primers for Amplifying CombiGEM Populations for Sequencing.

```
Forward primer:
                                       (SEQ ID NO: 2)
AATGATACGGCGACCACCGAGATCTACACCGCTGGCAAGTGTAGC Barcoded reverse primer:
                                       (SEQ ID NO: 3)
CAAGCAGAAGACGGCATACGAGATNNNNNNNGGGAGGGCCCGTTG Illumina sequencing primer:
                                       (SEQ ID NO: 4)
CCACGAGGATTCGAAAAGGTGAACCGACCCGGTCGATGCACTAGT Illumina indexing primer:
                                       (SEQ ID NO: 5)
CCTAGGAGCAAGTACGAACAACGGGCCCTCCC
```

Population Analysis.

Raw reads for each gene pair in each experiment were processed from sequencing data. To ensure valid log transformation downstream, a pseudo read of 1 was added for each gene pair-experiment combination. Reads for each combination were normalized to the total reads in each experiment and to fluorophore controls (pairwise combinations consisting only of eCFP (enhanced cyan fluorescent protein), GFP (green fluorescent protein), and mCherry) in each experiment. To correct for the batch effect of aTc using the multiplicative model, the normalized reads for each gene pair-experiment were divided by the median reads of that gene pair from all experiments in either aTc on or off. Finally, the normalized and batch corrected reads were log transformed, producing the comparable abundance for each combination of drug and gene pair. The difference between the abundances of a gene pair in two experiments corresponds to the log ratio of their normalized and batch corrected reads. The calculation of the interaction scores is based on the additive model between the comparable abundance for a gene pair under a particular drug condition and the mean of abundances for a reference set that consists of all the drug screens. The formula for the synergistic interaction S-score is defined as $$S_{ij}^k = \frac{\alpha_{ij}^k - \bar{\alpha}_{ij}}{\sigma_{ij}},$$

where i,j is a combination of genes i and j, k spans a set of experiments, $$\bar{\alpha}_{ij} = \frac{1}{n_{ij}} \sum_k \alpha_{ij}^k$$

is the mean of abundances $\alpha_{ij}^k$ from $n_{ij}$ experiments, and $\sigma_{ij}^k$ is the overall standard deviation with a minimum bound that accounts for the systematic variance.

Clustering Analysis.

Hierarchical clustering was performed across a subset of gene pairs and experiments with Pearson correlation and average linkage.

Antibiotic Susceptibility Assays.

Specific combinations identified through analysis were constructed on the vector backbone, verified through Sanger sequencing, and transformed into NDM-1. Frozen stocks were grown overnight in LB+Carb+Cm, then diluted 1:100 into 2 mL LB+Cm and grown at 37° C. for 1 hour. aTc and ceftriaxone were added where appropriate, and cultures were returned to 37° C. To obtain colony forming unit (cfu) counts at indicated time points, 100 μL of relevant cultures were collected, washed in phosphate buffered saline (PBS), and resuspended in 100 μL of PBS. Serial dilutions were performed with PBS, and 10 μL of each dilution was plated on LB agar plates. LB agar plates were incubated at 37° C. overnight before counting.

Flow Cytometry.

Cultures containing minimum and maximum fluorescence levels were used to calibrate the fluorescein isothiocyanate and PE-TexasRed® filter voltages on a BD LSRFortessa high-throughput sampler to measure GFP and mCherry expression levels, respectively. GFP was excited with a 488-nm laser and mCherry was excited with a 561-nm laser. Voltage compensation for fluorescein isothiocyanate and PE-TexasRed was not necessary for any experiment.

Example 7A

Demonstration of Massively Parallel Combinatorial Genetics in Yeast Cells

GFP and mCherry are each barcoded, placed under the control of a GAL-responsive promoter, and flanked by restriction sites for the restriction site methodology. These are placed in an pRS shuttle vector containing an E. coli pMB 1 origin, an ampicillin resistance cassette, a yeast centromere CEN6 origin, and the URA3 gene for auxotrophic selection.

Inserts are generated from vectors via PCR. A pooled combinatorial library is created and transformed into E. coli, from which plasmid is isolated and introduced into yeast cells. The pooled population containing all combinations of reporters is grown in the presence of galactose and analyzed via flow cytometry on green and red, showing three populations representing the three unique pairwise combinations of GFP and mCherry.

Example 7B

Demonstration of Massively Parallel Combinatorial Genetics in Yeast Cells

Massively parallel combinatorial genetics can be used to elucidate the pathological mechanisms underlying complex human diseases. For example, the methods provided herein may be used to investigate the regulation of lifespan and neurodegenerative disorders in yeast models. Through the exploration of high-order genetic interactions, the methods of the invention may be used to provide insights into novel therapeutic strategies and drug discovery in age-related diseases.

Two yeast models, one for Alzheimer's Disease (increased amyloid-β, Aβ, production) and the other for Parkinson's Disease (increased alpha-synuclein, αSyn), were used to explore combinatorial genetic factors that may be beneficial to clinical therapy.

Figure 28:
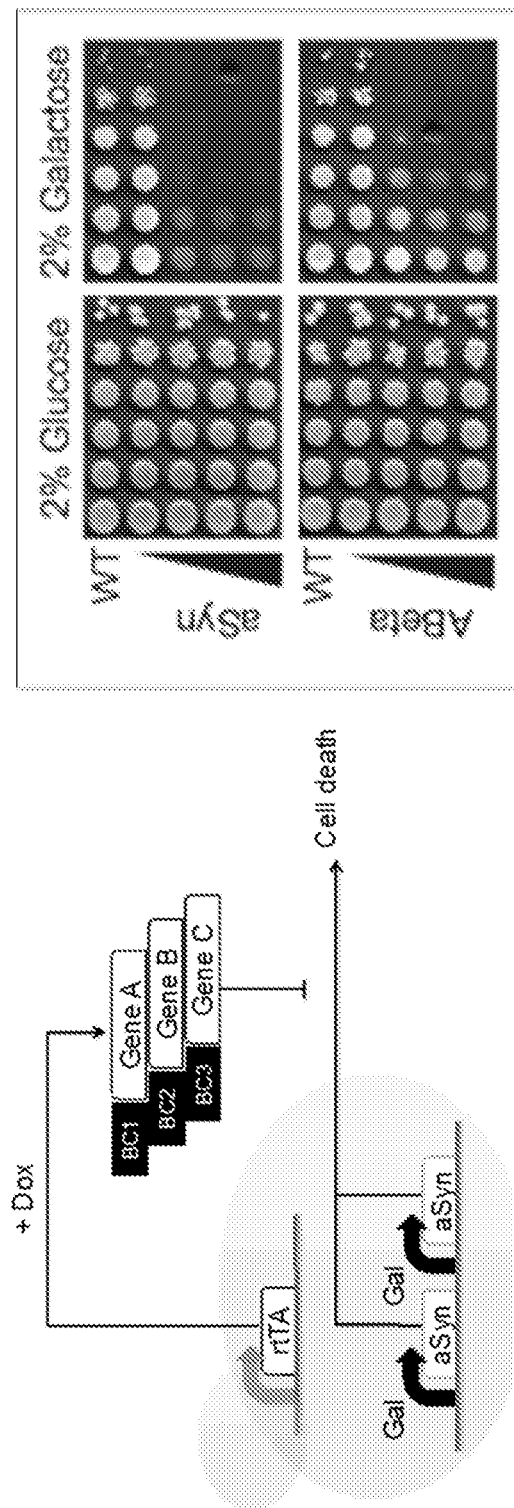
FIG. 28 depicts genetic screening strains generated by integrating multiple tandem copies of αSyn with a galactose (Gal)-inducible promoter. The expression of combinatorial libraries was controlled by the Tet-ON inducible system. The experiments were designed to recover genetic combinations that contribute to cell survival with Gal and doxycycline (Dox) treatment.

The repetitive Aβ or αSyn expression array was integrated in yeast genome (the W303 background) and controlled by galactose induction. FIG. 28 depicts a yeast strain generated by integrating multiple tandem copies of αSyn with a galactose (Gal)-inducible promoter. In order to minimize the size of plasmid backbone for library construction, the reverse tetracycline transactivator (rtTA), part of the Tet-ON expression system (Gossen, M. et al., *Science* 268(51218):1766-9 (1995)), was integrated into both yeast strains. The Tet-ON induction was tested by using different fluorescent proteins (such as eGFP and mCherry), and consistently detected robust gene activation (about 50-fold increase) with doxycycline (Dox) treatment. Furthermore, neither the integrated rtTA nor the Dox treatment affects cell growth or the inducible amyloid toxicity. Similarly, the rtTA was successfully integrated in wild-type strain (the BY4741 background) to study longevity.

Construction of Barcoded Combinatorial Library and Pairwise Combination Trial

An overexpression library of transcriptional regulators including 196 transcriptional factors and 29 histone modification enzymes was constructed. Amyloid toxicity is generally due to the dysfunction of protein quality control, therefore yeast genes involved in ubiquitin/proteasome, autophage, and chaperone pathways (another 224 genes) were also collected. With 54 genes known as Aβ (or αSyn) suppressors and yeast lifespan modulators, all the gene sequences were pooled together and two pairs of compatible restriction enzymes for BioBrick® assembly were identified. As shown in FIG. 29, each gene in the library and its unique barcode are flanked by universal restriction enzyme cutting sites so that one can, for example, systematically scale up the library assembly and perform high-throughput sequencing for genetic combinations, which is characteristic of Massively Parallel Combinatorial Genetics.

To validate the Massively Parallel Combinatorial Genetics strategy in yeast, a trial was set up with three fluorescent genes (EGFP, mCherry, and EBFP2). Each gene was cloned into the library backbone plasmid with an assigned barcode by the Gibson isothermal method. To construct pairwise combinations, individual barcoded plasmids were equally pooled together and then digested with AvrII and NotI as assembly vectors (FIG. 29). SpeI and PspOMI were used to create inserts from the same DNA pool. Through DNA ligation, all nine possible pairwise combinations were recovered by sequencing barcodes from random colonies.

Figure 30:
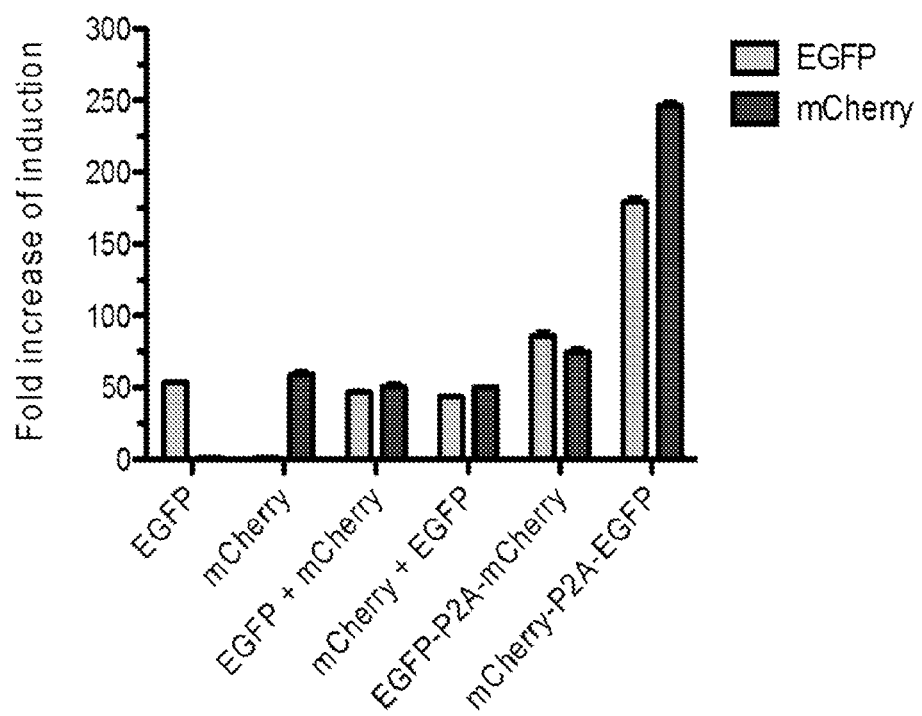
FIG. 30 depicts a graph showing quantitative analysis of gene expression of pairwise combinations of eGFP and mCherry constructed by Massively Parallel Combinatorial Genetics and P2A strategies.

Pairwise combinations of EGFP and mCherry were then chosen to examine gene expression in different order on the plasmid. In each case, both fluorescent genes show similar expression levels and are comparable to single gene construct (~50-fold induction) (FIG. 30). Massively parallel combinatorial genetics was compared with the P2A method for polycistronic expression (Fang et al., *Nature Biotechnology* 23:584-590 (2005)) to simultaneously express two fluorescent genes on the same plasmid. Unlike the expression profile of the Massively Parallel Combinatorial Genetics clones, the expression profile of the P2A clones is not predictable by exchanging the order of genes. Thus, the Massively Parallel Combinatorial Genetics strategy is powerful and reliable for building build a high-order combinatorial library.

CRISPR-Based Multiple Gene Targeting

In addition to Massively Parallel Combinatorial Genetics, a CRISPR (Clustered Regularly Interspaced Short Palindromic Repeats) strategy was used to program combinatorial gene expression in the yeast models. Generally, CRISPR carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Figure 31:
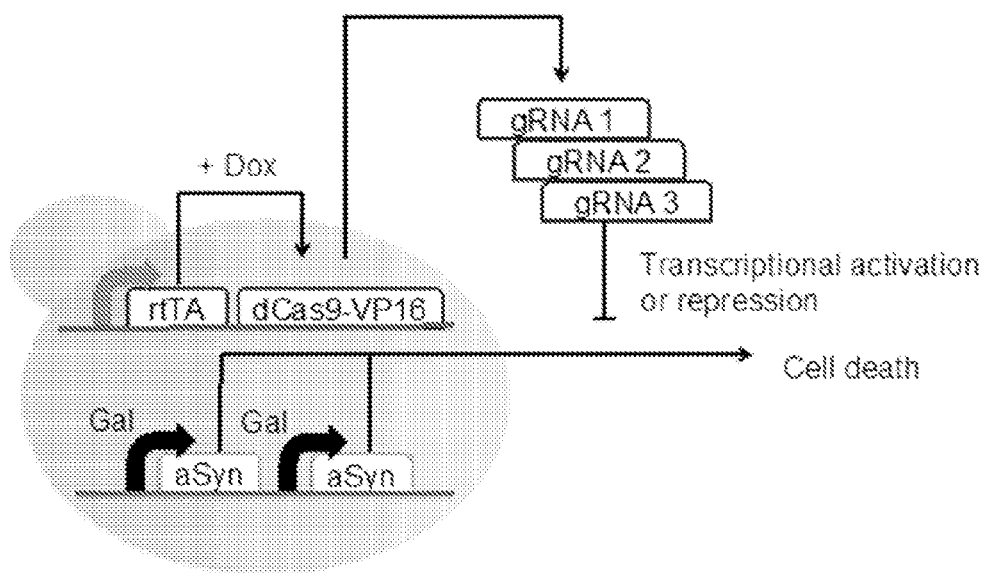
FIG. 31 depicts a massively parallel combinatorial genetic screen by RNA-guided transcriptional programming.

Herein, the synthetic Cas9 endonuclease complexes with designed guide RNAs (gRNAs) are used to determine site-specific digestion. By using a Cas9 nuclease mutant (dCas9) that retains the DNA-binding capacity, dCas9 was engineered to function as a transcriptional activator or repressor (dCas9-VP16), which is regulated by the Tet-ON inducible system, and integrated in the αSyn (also the longevity assay) strain (FIG. 31). The sequence binding specificity of gRNA is only contributed by its 16 nucleotide, suggesting that a single gRNA can mediate multiple gene targeting. In parallel, a combinatorial gRNA library for aging and age-related assays was also constructed. gRNAs are different only in 20 nucleotides, therefore they can be used as unique barcodes to recover genetic combinations by direct sequencing.

Figure 32:
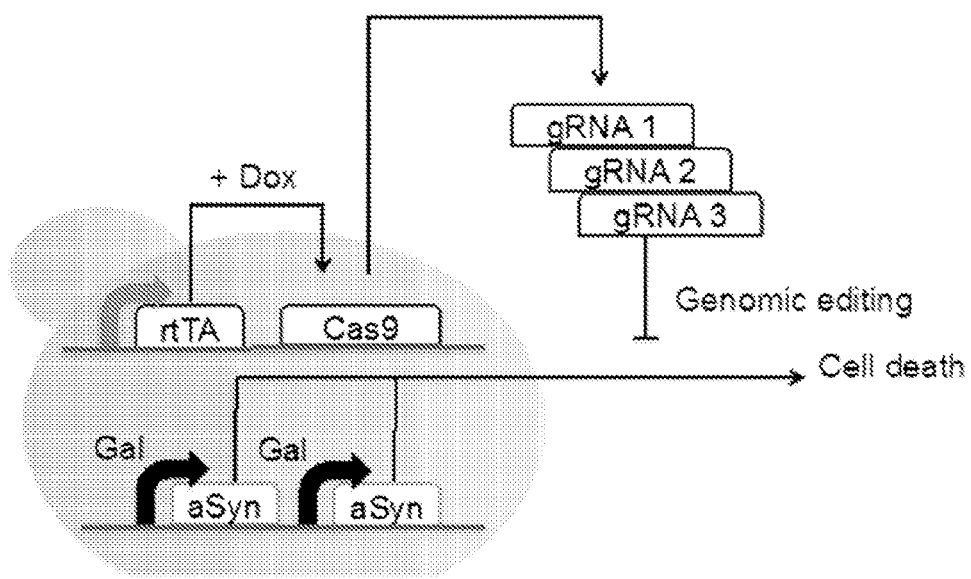
FIG. 32 depicts a massively parallel combinatorial genetic screen of genetic knockdowns.

Wild-type Cas9 was also integrated into the yeast model strains. With specific gRNA collections, early stop codons are introduced by gRNA-mediated genome editing. Thus, high-order combinatorial screening of genetic knockdown is performed (FIG. 32).

Example 8A

Demonstration of Massively Parallel Combinatorial Genetics in Mammalian Cells

GFP-mCherry combinations are also demonstrated in mammalian cells. GFP and mCherry are each barcoded, placed under the control of a tetracycline-responsive promoter (TRE), and flanked by restriction sites for the restriction site methodology. These are placed in a vector consisting of a pUC origin and a neomycin resistance cassette. Inserts are generated from vectors via PCR. A pooled combinatorial library is created and transformed into E. coli, from which plasmid is isolated and introduced into HeLa cells producing rtTA. The pooled population containing all combinations of reporters is grown in the presence of doxycycline and analyzed via flow cytometry on green and red, showing three populations representing the three unique pairwise combinations of GFP and mCherry.

Example 8B

Figure 33:
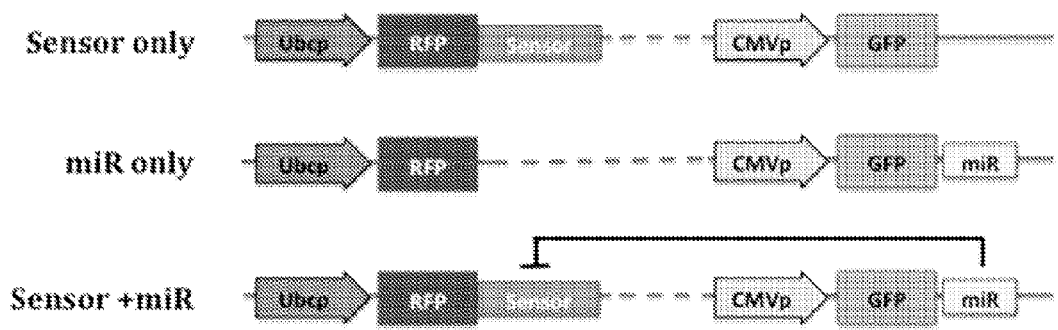
FIG. 33 depicts lentiviral vector designs. Tandem transcriptional units expressing precursor-miR along with a GFP gene driven by CMVp and/or a miR sensor sequence (e.g., four repeats of the miR's complementary target sequences) at the 3' UTR of a RFP gene driven by Ubcp were constructed in a lentiviral vector backbone. Ubcp, human ubiquitin C promoter; CMVp, human cytomegalovirus promoter; RFP, red fluorescent protein; GFP, green fluorescent protein.
Figure 34:
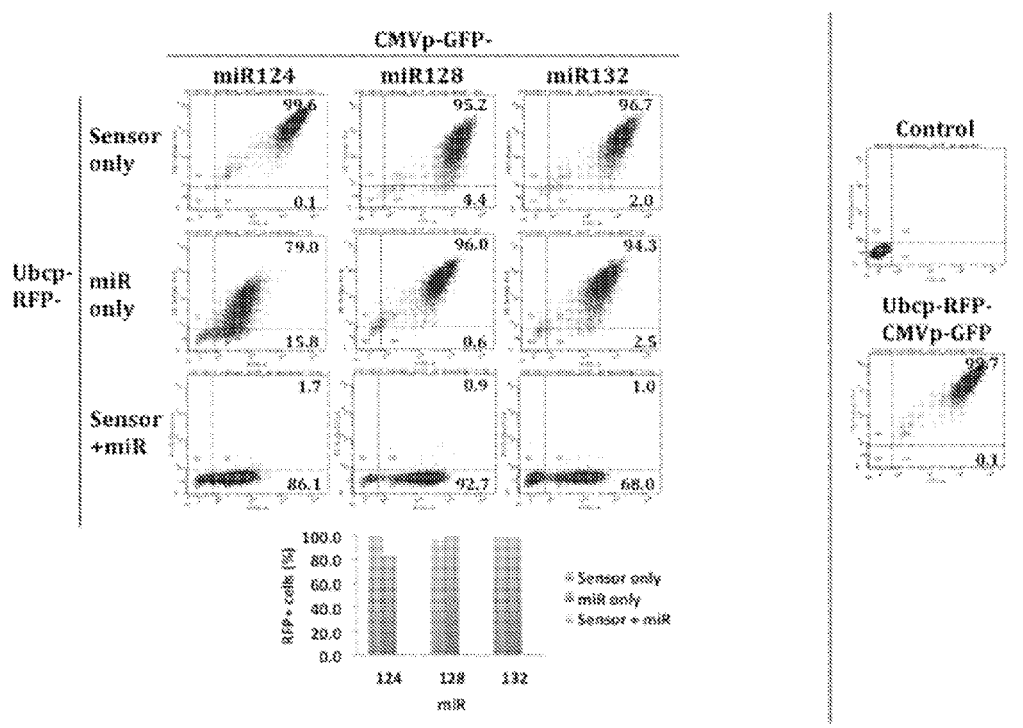
FIG. 34 depicts graphs showing precursor-miR expression in HEK293T cells. Lentiviruses containing tandem transcriptional units expressing three different precursor-miRs (i.e., miR-124, miR-128 and miR132) along with a GFP gene driven by CMVp and/or a miR sensor sequence at the 3'UTR of a RFP gene driven by Ubcp were used to infect HEK293T cells. Percentage of RFP cells over GFP$^+$ cells was determined by flow cytometer after gating with forward and side scatter. HEK293T; 4-day post-infection.
Figure 35:
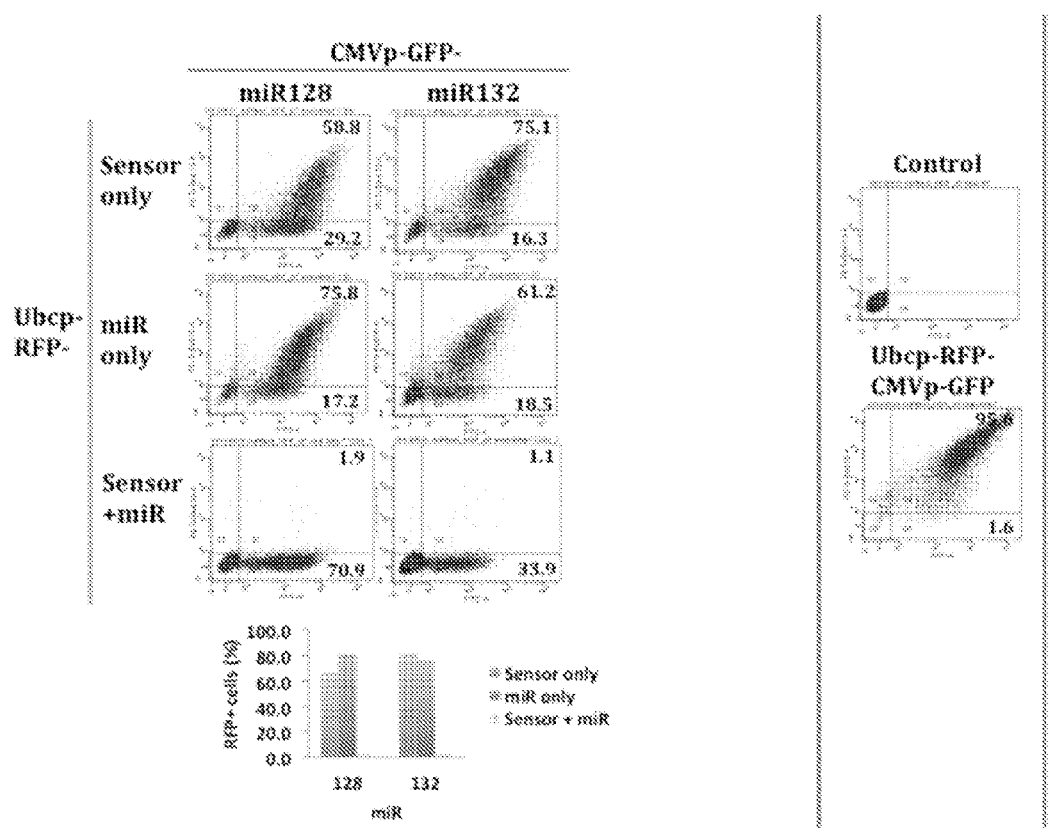
FIG. 35 depicts graphs showing precursor-miR expression in primary human dermal fibroblast (HDF) cells. Lentiviruses containing tandem transcriptional units expressing two different precursor-miRs (i.e., miR-128 and miR132) (SEQ ID NO:1) along with a GFP gene driven by a CMV promoter (CMVp) and/or a miR sensor sequence at the 3' UTR of an RFP gene driven by Ubcp were used to infect HDF cells. Percentage of RFP cells over GFP cells was determined by flow cytometer after gating with forward and side scatter. HEK293T; 7-day post-infection.
Figure 36:
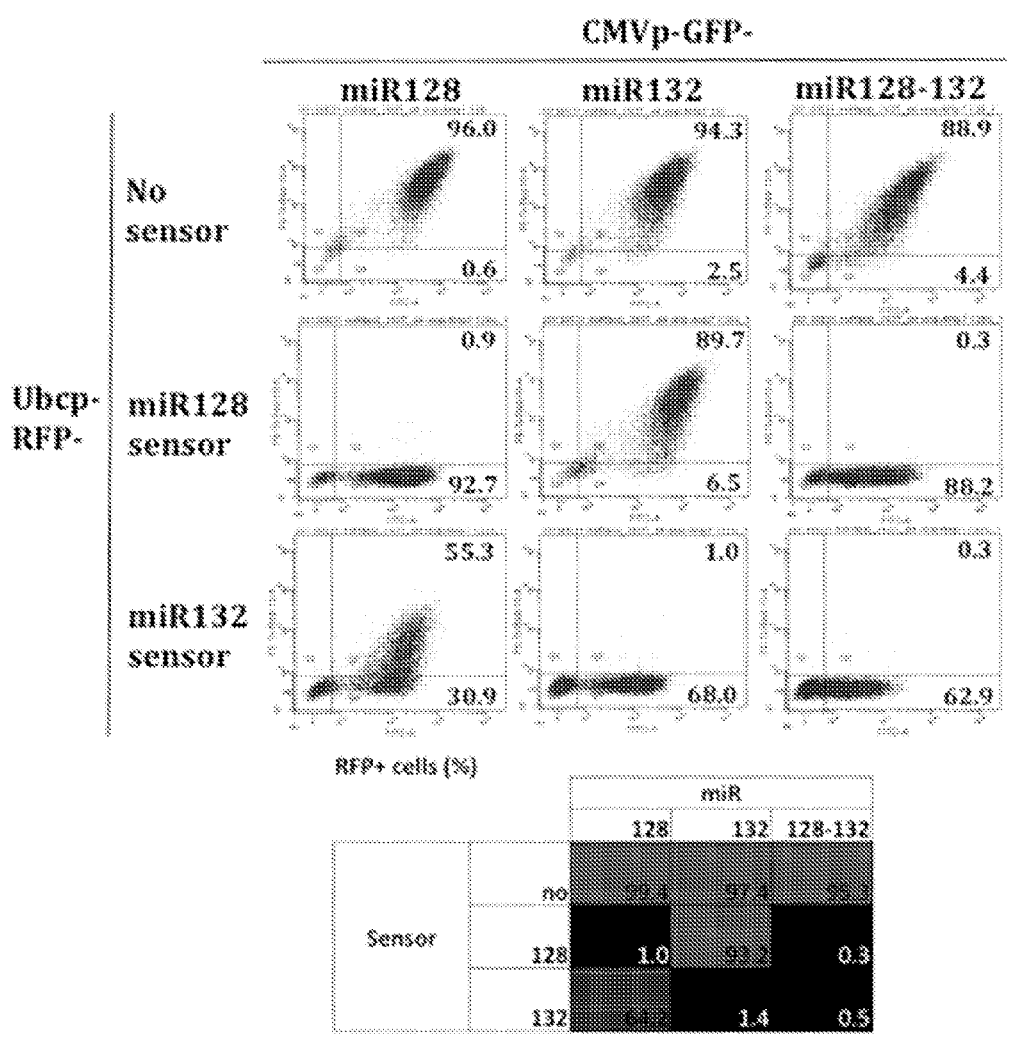
FIG. 36 depicts graphs showing combinatorial precursor-miR expression in HEK293T cells. Lentiviruses containing tandem transcriptional units expressing individual or combinatorial precursor-miRs (i.e., miR-128, miR-132, or miR-128-132) along with a GFP gene driven by CMVp and/or a miR sensor sequence at the 3' UTR of a RFP gene driven by Ubcp were used to infect HEK293T cells. Percentage of RFP cells over GFP$^+$ cells was determined by flow cytometer after gating with forward and side scatter. HEK293T; 4-day post-infection.
Figure 37:
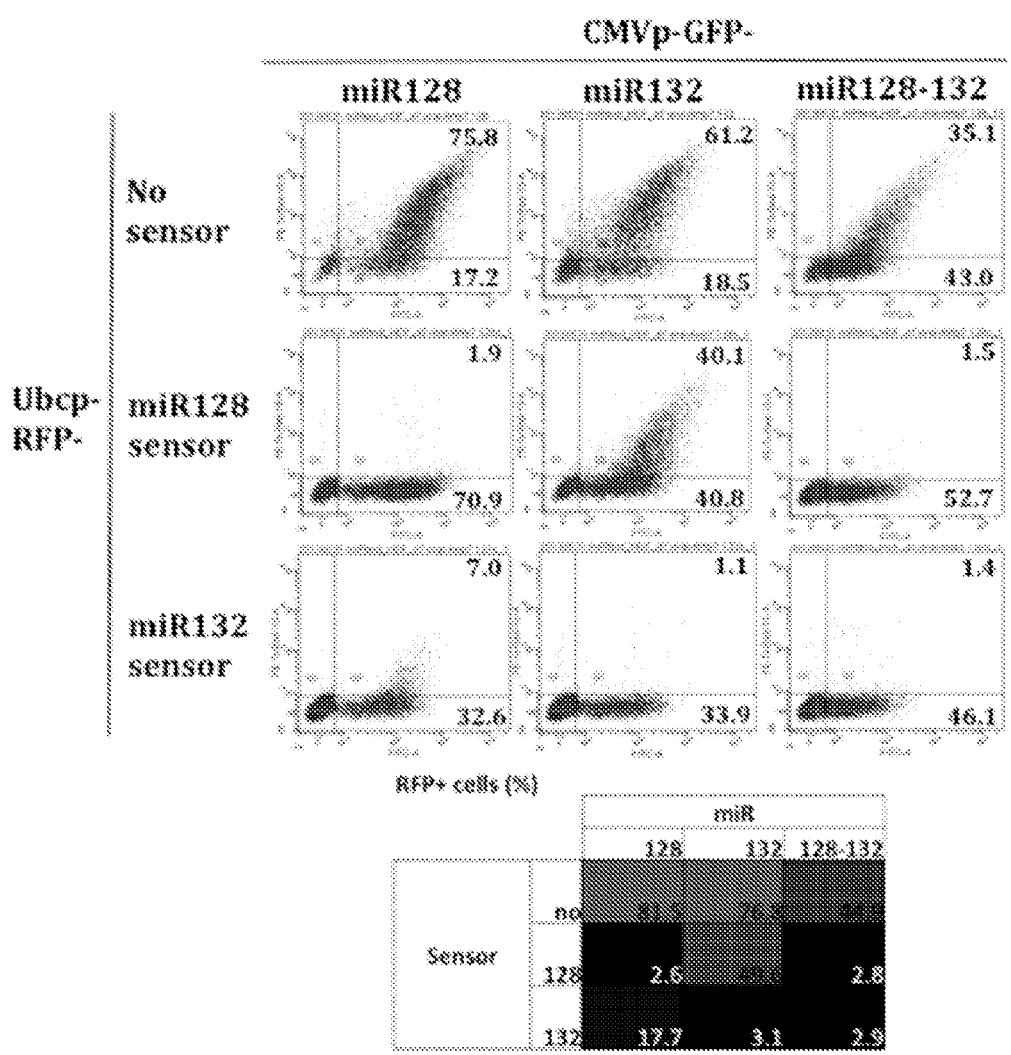
FIG. 37 depicts graphs showing combinatorial precursor-miR expression in primary HDF cells. Lentiviruses containing tandem transcriptional units expressing individual or combinatorial precursor-miRs (i.e., miR-128, miR-132, or miR-128-132) along with a GFP gene driven by CMVp and/or a miR sensor sequence at the 3'UTR of a RFP gene driven by Ubcp were used to infect HDF cells. Percentage of RFP cells over GFP$^+$ cells was determined by flow cytometer after gating with forward and side scatter. HEK293T; 7-day post-infection.
Figure 38:
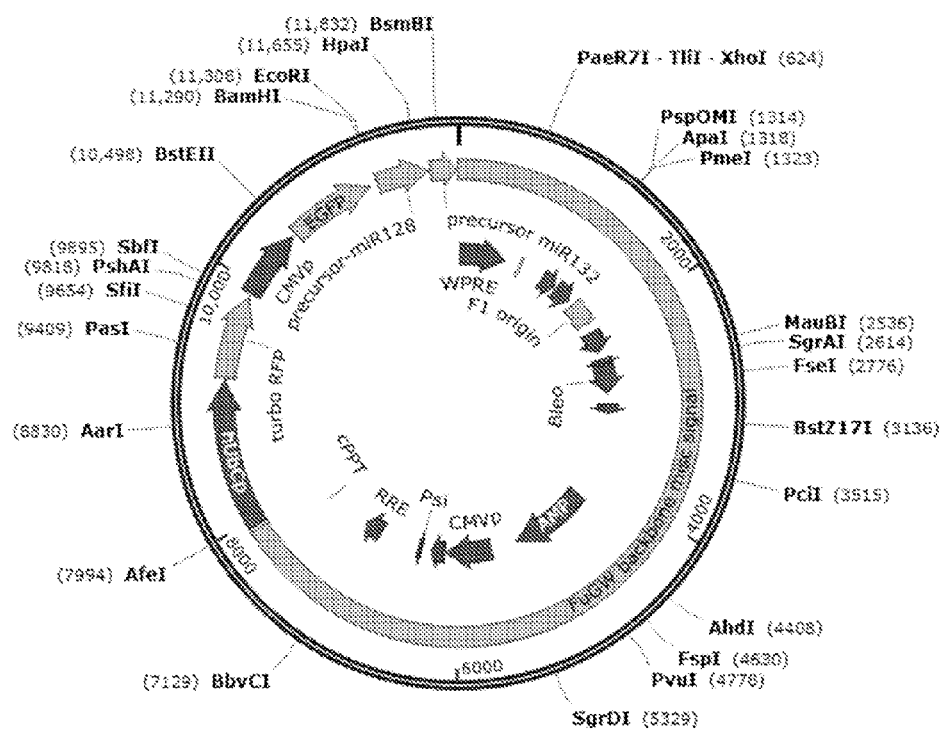
FIG. 38 depicts a map of a vector containing mir-128 and mir-132 in tandem.

Demonstration of Massively Parallel Combinatorial Genetics in Mammalian Cells Using Micro RNAs To express precursor-miR (microRNA) and measure its activity in human cells, a lentiviral vector consisted of tandem transcriptional units expressing precursor-miR along with a GFP gene and a miR sensor sequence (e.g., four repeats of the miR's complementary target sequences) at the 3'UTR of a RFP gene was constructed (FIG. 33). Control expression vectors without either precursor-miR or miR sensor sequence were also built for comparison (FIG. 33). Lentiviruses generated for each vector were used to infect human embryonic kidney cells (HEK293T) and primary human dermal fibroblasts (HDF). Flow cytometry was conducted to measure cell populations positive for GFP and RFP fluorescence, and the percentage of RFP+ cells over GFP+ cells was determined. Results revealed that the majority of GFP-precursor-miR-expressing cells did not display RFP fluorescence when the sensor sequence was included (FIGS. 34 and 35), indicating that individual precursor-miR can be expressed with our lentiviral vector in human cells. A single vector designed to allow combinatorial miRs expression would ensure their consistent expression ratio in all targeted cells. The lentiviral vector was next constructed to express two tandemly arranged precursor-miRs (e.g., miR-128-132) along with a GFP gene. The lentiviral vector may also be constructed with barcode elements, as described elsewhere herein. The expressed combinatorial precursor-miRs exhibited comparable activities as they were independently expressed (FIGS. 36 and 37). These results demonstrate that the lentiviral vector can be used to efficiently drive combinatorial miR expression in human cells. The lentiviral vectors used in this study are depicted in FIGS. 38 and 39.

Method
Lentiviral Vector Construction.
Precursor-miR (Table 3) and miR sensor (Table 4) sequences were PCR amplified from synthesized gene fragments and cloned into a lentiviral vector backbone.

TABLE 3

List of precursor-miR sequences used.

| Precursor-miR | Sequence |
| --- | --- |
| miR-124 | AGGTGGGAGTACTGCTCAGAGCTACAACTCTAGGAGTAG<br>GGACTCCAAGCCTAGAGCTCCAAGAGAGGGTGAAGGGCA<br>GGGAGAAAATTATAGTAATAGTTGCAATGAGTCACTTGCT<br>TCTAGATCAAGATCAGAGACTCTGCTCTCCGTGTTCACAG<br>CGGACCTTGATTTAATGTCATACAATTAAGGCACGCGGTG<br>AATGCCAAGAGCGGAGCCTACAGCTGCACTTGAAGGACA<br>TCCGAGAGAAGTTAGGAAGGGTGGGGAGAAACAATTCTA<br>GAATGAACCCATCCTGTGCGACAC (SEQ ID NO: 6) |

TABLE 3-continued

List of precursor-miR sequences used.

| Precursor-miR | Sequence |
| --- | --- |
| miR-128 | ATACTGTGAAGTACACTGCATATAAGGAGTGTGGTATAGT<br>ATAAAGAAACTTTCTGCAGGTAGTAATTATAGTGAAGATT<br>TTAGGTTTACAAAGCCCTAGCTGTTTTCTGTGTAGCTTTTA<br>TTATTCTTATGACTCTTGACAAGTTTGTAGCTTCACCATAT<br>ACATTTAATATTTTGCAATAATTGGCCTTGTTCCTGAGCTG<br>TTGGATTCGGGGCCGTAGCACTGTCTGAGAGGTTTACATT<br>TCTCACAGTGAACCGGTCTCTTTTTCAGCTGCTTCCTGGCT<br>TCTTTTTACTCAGGTTTCCACTGCTTTTTTGCTTTTTTTAAT<br>GCTGTATGAAGGTGTTAACATTTGTTTATATTTTTCATTAA<br>TTGTAATACCTTTAAATCATGCATCATACTCAGAAATAGG<br>GATTAGAATTTAAGTGACATCTTTGGCC<br>(SEQ ID NO: 7) |
| miR-132 | CTAGCCCCGCAGACACTAGCGCCACCCCCGCCGCCCGCG<br>GTGCTGACGTCAGCCTGCAAGCCCCGCCCCCGCGTCTCCA<br>GGGCAACCGTGGCTTTCGATTGTTACTGTGGGAACCGGAG<br>GTAACAGTCTACAGCCATGGTCGCCCCGCAGCACGCCCAC<br>GCTCCCCACCACTCCCGAGTTCTGCCAGCCTGGGTTTGGG<br>CAGATACAGAGCAAGAGGAGGCGGGG<br>(SEQ ID NO: 8) |

TABLE 4

List of miR sensor sequences used.

| miR sensors | Sequence |
| --- | --- |
| miR 124 | GGCACAGATAATAACCTGCAAAAAGGCATTCACCGCGTGC<br>CTTAGGCATTCACCGCGTGCCTTAGGCATTCACCGCGTGCC<br>TTAGGCATTCACCGCGTGCCTTAAATGCAGGCGGGCCAGAT<br>ATAC (SEQ ID NO: 9) |
| miR-128 | GGCACAGATAATAACCTGCAAAAAGAGACCGGTTCACTGT<br>GAAAAGAGACCGGTTCACTGTGAAAAGAGACCGGTTCAC<br>TGTGAAAAGAGACCGGTTCACTGTGAAATGCAGGCGGGC<br>CAGATATAC (SEQ ID NO: 10) |
| miR 132 | GGCACAGATAATAACCTGCAAAAACGACCATGGCTGTAGA<br>CTGTTACGACCATGGCTGTAGACTGTTACGACCATGGCTGT<br>AGACTGTTACGACCATGGCTGTAGACTGTTAAATGCAGGC<br>GGGCCAGATATAC (SEQ ID NO: 11) |

Example 9

Massively Parallel Combinatorial Genetics Using Recombinases

Massively parallel combinatorial genetics can also be achieved using recombinases. As shown in FIG. 9, recombination forms the basis behind techniques such as Gateway® cloning. Briefly, DNA pieces flanked by compatible recombination sequences can be exchanged using defined Clonase™ enzyme reaction mixes. For example, in Gateway® cloning, attB recombination sequences are compatible with attP sequences and form attL and attR sites after the recombination reaction. attL and attR sites are in turn compatible and generate attB and attP sites. In Gateway® technology, four orthogonal sets of attB, attP, attL and attR sequences exist.

A non-limiting example of a recombination-mediated combinatorial genetics technology is shown in FIG. 11. This embodiment employs two vector libraries, in which two recombination sequences are located between the DNA element and its barcode element. The inserts can be generated by PCR and can contain a flanking pair of orthogonal recombination sequences. att recombination sequences are represented by B, P, L or R. BC=Barcode, DNA=DNA element.

As shown in FIG. 12, to generate combinations iteratively, a vector from either library can be used. The iterative reaction proceeds by alternating between the two insert libraries, beginning with the inserts generated from the vector library that was not used for the initial recombination step.

The specific recombination sequences to be used can be altered as long as minimal requirements for compatibility are met to prevent undesired recombination. The approximate lengths of attB, attP, attL, and attR sequences are 30, 240, 100, and 160 nucleotides, respectively. In some embodiments, insertion of attB and attL sites between barcodes can optimize the length of sequence to be read by sequencing or other methods.

Example 10

Massively Parallel Combinatorial Genetics Using a Single Enzyme Separation Site

Massively parallel combinatorial genetics can be conducted using a single restriction site located between the DNA element and barcode element within a genetic construct. FIG. 15 demonstrates a vector in which a barcode element and DNA element are separated by a restriction site for the restriction enzyme BglII. Also depicted is an insert that contains a DNA element and a barcode element. The insert contains a restriction site for the restriction enzyme BglII located between the DNA element and barcode element, and restriction sites for the restriction enzyme AlwNI located outside the DNA element and barcode element. The restriction enzymes BglII and AlwNI generate compatible ends such that when the vector is cleaved by BglII and the insert is cleaved by AlwNI, the vector and insert are annealed to each other, generating a vector that contains two DNA elements and two barcode elements separated by a single restriction site for the enzyme BglII.

The invention is further described by the following numbered paragraphs:
1. A genetic construct comprising:
 a DNA element;
 a first compatible end element and a second compatible end element flanking the DNA element, wherein the first and second compatible end elements are capable of annealing to each other;
 a barcode element;
 a third compatible end element and a fourth compatible end element flanking the barcode element, wherein the third and fourth compatible end elements are capable of annealing to each other but are not capable of annealing to the first or second compatible end elements; and
 a separation site located between the fourth compatible end element and the first compatible end element, wherein the DNA element, first compatible end element and second compatible end element are on one side of the separation site, and the barcode element, third compatible end element and fourth compatible end element are on the other side of the separation site.
2. The genetic construct according to paragraph 1, wherein the DNA element contains at least two nucleotide sequences in tandem, each nucleotide sequence encoding a gene of interest.
3. The genetic construct according to paragraph 2, wherein the genetic construct contains at least two barcode elements in tandem.
4. The genetic construct according to any one of paragraphs 1-3, wherein each nucleotide sequence is operably linked to an inducible promoter.
5. The genetic construct according to any one of paragraphs 2-4, wherein the gene of interest is a transcription factor and/or histone modification enzyme.
6. The genetic construct according to any one of paragraphs 2-5, wherein:
 (a) at least one of the nucleotide sequences encodes mtlR and at least one of the nucleotide sequences encodes uidR;
 (b) at least one of the nucleotide sequences encodes qseB and at least one of the nucleotide sequences encodes bolA;
 (c) at least one of the nucleotide sequences encodes rstA and at least one of the nucleotide sequences encodes rob;
 (d) at least one of the nucleotide sequences encodes rstA and at least one of the nucleotide sequences encodes mirA;
 (e) at least one of the nucleotide sequences encodes rcsB and at least one of the nucleotide sequences encodes mirA;
 (f) at least one of the nucleotide sequences encodes feaR and at least one of the nucleotide sequences encodes hcaR;
 (g) at least one of the nucleotide sequences encodes feaR and at least one of the nucleotide sequences encodes hcaR;
 (h) at least one of the nucleotide sequences encodes torR and at least one of the nucleotide sequences encodes metR;
 (i) at least one of the nucleotide sequences encodes nhaR and at least one of the nucleotide sequences encodes melR;
 (j) at least one of the nucleotide sequences encodes allR and at least one of the nucleotide sequences encodes melR;
 (k) at least one of the nucleotide sequences encodes malL and at least one of the nucleotide sequences encodes yfeT;
 (l) at least one of the nucleotide sequences encodes cadC and at least one of the nucleotide sequences encodes allR;
 (m) at least one of the nucleotide sequences encodes torR; or
 (n) at least one of the nucleotide sequences encodes metR.
7. The genetic construct according to any one of paragraphs 2-6, wherein the at least two nucleotide sequences in tandem potentiate antibiotic lethality in a bacterial cell.
8. The genetic construct according to paragraph 7, wherein the bacterial cell is resistant to at least one antibiotic.
9. The genetic construct according to paragraph 7 or 8, wherein the bacterial cell is a New Delhi metallo-betalactamase 1 (NDM-1) *Escherichia coli* cell.
10. The genetic construct according to paragraph 8 or 9, wherein the antibiotic is ceftriaxone, imipenem, piperacillin, tazobactum, gentamicin or a combination of any two or more of the foregoing.
11. The genetic construct according to paragraph 1, wherein the DNA element contains at least one microRNA (miR) sequence, or at least two miR sequences in tandem.
12. The genetic construct according to paragraph 11, wherein the genetic construct contains at least two barcode elements in tandem.
13. The genetic construct according to paragraph 11 or 12, wherein the miR is operably linked to an inducible promoter.
14. The genetic construct according to any one of paragraphs 11-13, wherein the miR is selected from miR-124, miR-128 and miR-138.
15. The genetic construct according to any one of paragraphs 11-13, wherein the at least two miR in tandem are a combination selected from miR-124, miR-128 and miR-138.
16. A phagemid comprising at least one genetic construct according to any one of paragraphs 1-15.

17. A recombinant bacteriophage comprising the phagemid according to paragraph 16.

18. The recombinant bacteriophage according to paragraph 17, wherein the recombinant bacteriophage is of a family selected from Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae and Cystoviridae.

19. The recombinant bacteriophage according to paragraph 18, wherein the recombinant Inoviridae bacteriophage is an M13 or M13-like bacteriophage.

20. A method of screening for genes that potentiate antibiotic lethality, the method comprising:
transforming antibiotic resistant bacterial cells with the library comprising two of more genetic constructs according to any one of paragraphs 1-15;
subjecting the transformed bacterial cells to treatment with a cognate inducer, an antibiotic, and a combination of cognate inducer and antibiotic treatment; comparing cell phenotypes among each treatment condition; and
selecting phenotypes of synergistic killing, neutral growth and assessing cell phenotype for each treatment.

21. The method according to paragraph 20, further comprising sequencing genetic constructs from bacterial cells having selected phenotypes.

22. A method for generating a combinatorial genetic construct, comprising:
providing a vector containing a first genetic construct according to any one of paragraphs 1-15;
cleaving the vector at the separation site within the first genetic construct, resulting in the first genetic construct being separated into first and second segments;
providing a second genetic construct according to any one of paragraphs A1-A15; and
annealing the second genetic construct to the cleaved vector, wherein the annealing occurs at compatible end elements within the first and second genetic constructs that are capable of annealing to each other, and wherein after annealing, the second genetic construct is integrated between the first and second segments of the first genetic construct, creating a combinatorial genetic construct.

23. The method according to paragraph 22, wherein the method is iterative.

24. A method for identification of a DNA element or a plurality of DNA elements, comprising:
providing a genetic construct according to any one of paragraphs 1-15;
conducting an assay to determine the DNA sequence of the barcode or plurality of barcodes within the genetic construct and/or the DNA sequence of the DNA element or plurality of DNA elements within the genetic construct; and
identifying the DNA element or plurality of DNA elements.

25. A library comprising:
two or more genetic constructs according to any one of paragraphs 1-15.

26. A method for generating a combinatorial genetic construct, comprising:
providing a vector comprising:
a first DNA element,
a first barcode element, and
two site-specific recombination elements located between the first DNA element and the first barcode element;
providing a first insert comprising:
a second DNA element,
a second barcode element, and
site-specific recombination elements flanking each of the second DNA element and the second barcode element, such that two site-specific recombination elements are located between the second DNA element and the second barcode element that are not compatible with the site-specific recombination elements within the vector, and two site-specific recombination elements are located outside of the second DNA element and the second barcode element that are compatible with the site-specific recombination elements within the vector;
conducting site specific recombination between the vector and the first insert, wherein the site specific recombination occurs between the site-specific recombination elements within the vector located between the first DNA element and the first barcode element and the compatible site-specific recombination elements within the first insert located outside of the second DNA element and the second barcode element, and wherein following site-specific recombination, the first insert is located within the vector, and the vector contains multiple DNA elements and multiple barcode elements, with two site-specific recombination elements located between the multiple DNA elements and the multiple barcode elements;
providing a second insert comprising:
a third DNA element,
a third barcode element, and
site-specific recombination elements flanking each of the third DNA element and the third barcode element, such that two site-specific recombination elements are located between the third DNA element and the third barcode element that are not compatible with the two site-specific recombination elements located between the multiple DNA elements and the multiple barcode elements of the vector, and two site-specific recombination elements are located outside of the third DNA element and the third barcode element that are compatible with the two site-specific recombination elements located between the multiple DNA elements and the multiple barcode elements of the vector;
conducting site specific recombination between the vector and the second insert, wherein the site specific recombination occurs between the site-specific recombination elements within the vector located between the multiple DNA elements and the multiple barcode elements and the compatible site-specific recombination elements within the second insert located outside of the third DNA element and the third barcode element, and wherein following site-specific recombination, the second insert is located within the vector, and the vector contains multiple DNA elements and multiple barcode elements, with two site-specific recombination elements located between the multiple DNA elements and the multiple barcode elements; and
repeating the site-specific recombination an $n^{th}$ number of times, alternating between site-specific recombination between the vector and the first insert and site-specific recombination between the vector and the second insert, thereby creating a combinatorial genetic construct.

27. The method according to paragraph 26, wherein each DNA element contains a nucleotide sequence encoding a different, or unique, transcription factor and/or histone modification enzyme.

28. The method according to paragraph 26, wherein each DNA element contains a nucleotide sequence encoding a different, or unique, microRNA (miR)

29. A combinatorial genetic construct produced by the method according to any one of paragraphs 26-28.

30. A method for identification of a DNA element or a plurality of DNA elements, comprising:

providing a combinatorial genetic construct according to paragraph 29;
conducting an assay to determine the DNA sequence of one or more barcode elements within the combinatorial genetic construct and/or the DNA sequence of one or more DNA elements within the combinatorial genetic construct; and
identifying the DNA element or plurality of DNA elements.

31. A method for generating a combinatorial genetic construct, comprising:
providing a vector comprising:
a first DNA element,
a first barcode element, and
a recognition site for a first restriction enzyme located between the first DNA element and the first barcode element;
providing an insert comprising:
a second DNA element,
a second barcode element,
a recognition site for the first restriction enzyme located between the second DNA element and the second barcode element, and
two recognition sites for one or more restriction enzymes that are distinct from the first restriction enzyme located outside of the second DNA element and second barcode element, such that restriction digestion at the recognition site within the vector and at the two recognition sites located outside of the second DNA element and second barcode element within the insert generates compatible ends;
digesting the vector and insert with restriction enzymes;
annealing the insert to the vector, thereby producing a combinatorial genetic construct containing multiple DNA elements and multiple barcode elements; and
optionally repeating the method an $n^{th}$ number of times.

32. The method according to paragraph 31, wherein each DNA element contains a nucleotide sequence encoding a different, or unique, transcription factor and/or histone modification enzyme.

33. The method according to paragraph 31, wherein each DNA element contains a nucleotide sequence encoding a different, or unique, microRNA (miR)

34. A combinatorial genetic construct produced by the method according to any one of paragraphs 31-33.

35. A method for identification of a DNA element or a plurality of DNA elements, comprising:
providing a combinatorial genetic construct according to paragraph 34;
conducting an assay to determine the DNA sequence of one or more barcode elements within the combinatorial genetic construct and/or the DNA sequence of one or more DNA elements within the combinatorial genetic construct; and
identifying the DNA element or plurality of DNA elements.

SEQUENCES
SEQ ID NO: 1 - Tandem precursor-miR expression
CGATATCAAGCTTATCGATAATCAACCTCTGGATTACAAAATTTGTGAAA

GATTGACTGGTATTCTTAACTATGTTGCTCCTTTTACGCTATGTGGATAC

GCTGCTTTAATGCCTTTGTATCATGCTATTGCTTCCCGTATGGCTTTCAT

TTTCTCCTCCTTGTATAAATCCTGGTTGCTGTCTCTTTATGAGGAGTTGT

GGCCCGTTGTCAGGCAACGTGGCGTGGTGTGCACTGTGTTTGCTGACGCA

-continued
ACCCCCACTGGTTGGGGCATTGCCACCACCTGTCAGCTCCTTTCCGGGAC

TTTCGCTTTCCCCCTCCCTATTGCCACGGCGGAACTCATCGCCGCCTGCC

TTGCCCGCTGCTGGACAGGGGCTCGGCTGTTGGGCACTGACAATTCCGTG

GTGTTGTCGGGGAAATCATCGTCCTTTCCTTGGCTGCTCGCCTGTGTTGC

CACCTGGATTCTGCGCGGGACGTCCTTCTGCTACGTCCCTTCGGCCCTCA

ATCCAGCGGACCTTCCTTCCCGCGGCCTGCTGCCGGCTCTGCGGCCTCTT

CCGCGTCTTCGCCTTCGCCCTCAGACGAGTCGGATCTCCCTTTGGGCCGC

CTCCCCGCATCGATACCGTCGACCTCGAGACCTAGAAAAACATGGAGCAA

TCACAAGTAGCAATACAGCAGCTACCAATGCTGATTGTGCCTGGCTAGAA

GCACAAGAGGAGGAGGAGGTGGGTTTTCCAGTCACACCTCAGGTACCTTT

AAGACCAATGACTTACAAGGCAGCTGTAGATCTTAGCCACTTTTTAAAAG

AAAAGGGGGGACTGGAAGGGCTAATTCACTCCCAACGAAGACAAGATATC

CTTGATCTGTGGATCTACCACACACAAGGCTACTTCCCTGATTGGCAGAA

CTACACACCAGGGCCAGGGATCAGATATCCACTGACCTTTGGATGGTGCT

ACAAGCTAGTACCAGTTGAGCAAGAGAAGGTAGAAGAAGCCAATGAAGGA

GAGAACACCCGCTTGTTACACCCTGTGAGCCTGCATGGGATGGATGACCC

GGAGAGAGAAGTATTAGAGTGGAGGTTTGACAGCCGCCTAGCATTTCATC

ACATGGCCCGAGAGCTGCATCCGGACTGTACTGGGTCTCTCTGGTTAGAC

CAGATCTGAGCCTGGGAGCTCTCTGGCTAACTAGGGAACCCACTGCTTAA

GCCTCAATAAAGCTTGCCTTGAGTGCTTCAAGTAGTGTGTGCCCGTCTGT

TGTGTGACTCTGGTAACTAGAGATCCCTCAGACCCTTTTAGTCAGTGTGG

AAAATCTCTAGCAGGGCCCGTTTAAACCCGCTGATCAGCCTCGACTGTGC

CTTCTAGTTGCCAGCCATCTGTTGTTTGCCCCTCCCCCGTGCCTTCCTTG

ACCCTGGAAGGTGCCACTCCCACTGTCCTTTCCTAATAAAATGAGGAAAT

TGCATCGCATTGTCTGAGTAGGTGTCATTCTATTCTGGGGGGTGGGGTGG

GGCAGGACAGCAAGGGGGAGGATTGGGAAGACAATAGCAGGCATGCTGGG

GATGCGGTGGGCTCTATGGCTTCTGAGGCGGAAAGAACCAGCTGGGGCTC

TAGGGGGTATCCCCACGCGCCCTGTAGCGGCGCATTAAGCGCGGCGGGTG

TGGTGGTTACGCGCAGCGTGACCGCTACACTTGCCAGCGCCCTAGCGCCC

GCTCCTTTCGCTTTCTTCCCTTCCTTTCTCGCCACGTTCGCCGGCTTTCC

CCGTCAAGCTCTAAATCGGGGGCTCCCTTTAGGGTTCCGATTTAGTGCTT

TACGGCACCTCGACCCCAAAAAACTTGATTAGGGTGATGGTTCACGTAGT

GGGCCATCGCCCTGATAGACGGTTTTTCGCCCTTTGACGTTGGAGTCCAC

GTTCTTTAATAGTGGACTCTTGTTCCAAACTGGAACAACACTCAACCCTA

TCTCGGTCTATTCTTTTGATTTATAAGGGATTTTGCCGATTTCGGCCTAT

TGGTTAAAAAATGAGCTGATTTAACAAAAATTTAACGCGAATTAATTCTG

TGGAATGTGTGTCAGTTAGGGTGTGGAAAGTCCCCAGGCTCCCCAGCAGG

CAGAAGTATGCAAAGCATGCATCTCAATTAGTCAGCAACCAGGTGTGGAA

AGTCCCCAGGCTCCCCAGCAGGCAGAAGTATGCAAAGCATGCATCTCAAT

TAGTCAGCAACCATAGTCCCGCCCCTAACTCCGCCCATCCCGCCCCTAAC

TCCGCCCAGTTCCGCCCATTCTCCGCCCCATGGCTGACTAATTTTTTTTA

-continued

```
TTTATGCAGAGGCCGAGGCCGCCTCTGCCTCTGAGCTATTCCAGAAGTAG
TGAGGAGGCTTTTTTGGAGGCCTAGGCTTTTGCAAAAAGCTCCCGGGAGC
TTGTATATCCATTTTCGGATCTGATCAGCACGTGTTGACAATTAATCATC
GGCATAGTATATCGGCATAGTATAATACGACAAGGTGAGGAACTAAACCA
TGGCCAAGTTGACCAGTGCCGTTCCGGTGCTCACCGCGCGCGACGTCGCC
GGAGCGGTCGAGTTCTGGACCGACCGGCTCGGGTTCTCCCGGGACTTCGT
GGAGGACGACTTCGCCGGTGTGGTCCGGGACGACGTGACCCTGTTCATCA
GCGCGGTCCAGGACCAGGTGGTGCCGGACAACACCCTGGCCTGGGTGTGG
GTGCGCGGCCTGGACGAGCTGTACGCCGAGTGGTCGGAGGTCGTGTCCAC
GAACTTCCGGGACGCCTCCGGGCCGGCCATGACCGAGATCGGCGAGCAGC
CGTGGGGCGGGAGTTCGCCCTGCGCGACCCGGCCGGCAACTGCGTGCAC
TTCGTGGCCGAGGAGCAGGACTGACACGTGCTACGAGATTTCGATTCCAC
CGCCGCCTTCTATGAAAGGTTGGGCTTCGGAATCGTTTTCCGGGACGCCG
GCTGGATGATCCTCCAGCGCGGGGATCTCATGCTGGAGTTCTTCGCCCAC
CCCAACTTGTTTATTGCAGCTTATAATGGTTACAAATAAAGCAATAGCAT
CACAAATTTCACAAATAAAGCATTTTTTTCACTGCATTCTAGTTGTGGTT
TGTCCAAACTCATCAATGTATCTTATCATGTCTGTATACCGTCGACCTCT
AGCTAGAGCTTGGCGTAATCATGGTCATAGCTGTTTCCTGTGTGAAATTG
TTATCCGCTCACAATTCCACACAACATACGAGCCGGAAGCATAAAGTGTA
AAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATG
AATCGGCCAACGCGCGGGGAGAGGCGGTTTGCGTATTGGGCGCTCTTCCG
CTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGA
TAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTA
AGACACGACTTATCGCCACTGGCAGCAGCCACTGGTAACAGGATTAGCAG
AGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCA
GTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCT
CAGTGGAACGAAAACTCACGTTAAGGGATTTTGGTCATGAGATTATCAAA
AAGGATCTTCACCTAGATCCTTTTAAATTAAAAATGAAGTTTTAAATCAA
TCTAAAGTATATATGAGTAAACTTGGTCTGACAGTTACCAATGCTTAATC
AGTGAGGCACCTATCTCAGCGATCTGTCTATTTCGTTCATCCATAGTTGC
CTGACTCCCCGTCGTGTAGATAACTACGATACGGGAGGGCTTACCATCTG
GCCCCAGTGCTGCAATGATACCGCGAGACCCACGCTCACCGGCTCCAGAT
TTATCAGCAATAAACCAGCCAGCCGGAAGGGCCGAGCGCAGAAGTGGTCC
TGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTC
CGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCC
GCAGTGTTATCACTCATGGTTATGGCAGCACTGCATAATTCTCTTACTGT
CATGCCATCCGTAAGATGCTTTTCTGTGACTGGTGAGTACTCAACCAAGT
CATTCTGAGAATAGTGTATGCGGCGACCGAGTTGCTCTTGCCCGGCGTCA
ATACGGGATAATACCGCGCCACATAGCAGAACTTTAAAAGTGCTCATCAT
TGGAAAACGTTCTTCGGGGCGAAAACTCTCAAGGATCTTACCGCTGTTGA
GATCCAGTTCGATGTAACCCACTCGTGCACCCAACTGATCTTCAGCATCT
TTTACTTTCACCAGCGTTTCTGGGTGAGCAAAAACAGGAAGGCAAAATGC
CGCAAAAAAGGGAATAAGGGCGACACGGAAATGTTGAATACTCATACTCT
TCCTTTTTCAATATTATTGAAGCATTTATCAGGGTTATTGTCTCATGAGC
GGATACATATTTGAATGTATTTAGAAAAATAAACAAATAGGGGTTCCGCG
CACATTTCCCCGAAAAGTGCCACCTGACGTCGACGGATCGGGAGATCTCC
CGATCCCCTATGGTGCACTCTCAGTACAATCTGCTCTGATGCCGCATAGT
TAAGCCAGTATCTGCTCCCTGCTTGTGTGTTGGAGGTCGCTGAGTAGTGC
GCGAGCAAAATTTAAGCTACAACAAGGCAAGGCTTGACCGACAATTGCAT
GAAGAATCTGCTTAGGGTTAGGCGTTTTGCGCTGCTTCGCGATGTACGGG
CCAGATATACGCGTTGACATTGATTATTGACTAGTTATTAATAGTAATCA
ATTACGGGTCATTAGTTCATAGCCCATATATGGAGTTCCGCGTTACATA
ACTTACGGTAAATGGCCCGCCTGGCTGACCGCCCAACGACCCCCGCCCAT
TGACGTCAATAATGACGTATGTTCCCATAGTAACGCCAATAGGGACTTTC
CATTGACGTCAATGGGTGGAGTATTTACGGTAAACTGCCCACTTGGCAGT
ACATCAAGTGTATCATATGCCAAGTACGCCCCCTATTGACGTCAATGACG
GTAAATGGCCCGCCTGGCATTATGCCCAGTACATGACCTTATGGGACTTT
CCTACTTGGCAGTACATCTACGTATTAGTCATCGCTATTACCATGGTGAT
GCGGTTTTGGCAGTACATCAATGGGCGTGGATAGCGGTTTGACTCACGGG
GATTTCCAAGTCTCCACCCCATTGACGTCAATGGGAGTTTGTTTTGGCAC
CAAAATCAACGGGACTTTCCAAAATGTCGTAACAACTCCGCCCCATTGAC
GCAAATGGGCGGTAGGCGTGTACGGTGGGAGGTCTATATAAGCAGCGCGT
TTTGCCTGTACTGGGTCTCTCTGGTTAGACCAGATCTGAGCCTGGGAGCT
CTCTGGCTAACTAGGGAACCCACTGCTTAAGCCTCAATAAAGCTTGCCTT
GAGTGCTTCAAGTAGTGTGTGCCCGTCTGTTGTGTGACTCTGGTAACTAG
AGATCCCTCAGACCCTTTTAGTCAGTGTGGAAAATCTCTAGCAGTGGCGC
```

```
CCGAACAGGGACTTGAAAGCGAAAGGGAAACCAGAGGAGCTCTCTCGACG
CAGGACTCGGCTTGCTGAAGCGCGCACGGCAAGAGGCGAGGGGCGGCGAC
TGGTGAGTACGCCAAAAATTTTGACTAGCGGAGGCTAGAAGGAGAGAGAT
GGGTGCGAGAGCGTCAGTATTAAGCGGGGAGAATTAGATCGCGATGGGA
AAAAATTCGGTTAAGGCCAGGGGGAAAGAAAAAATATAAATTAAAACATA
TAGTATGGGCAAGCAGGGAGCTAGAACGATTCGCAGTTAATCCTGGCCTG
TTAGAAACATCAGAAGGCTGTAGACAAATACTGGGACAGCTACAACCATC
CCTTCAGACAGGATCAGAAGAACTTAGATCATTATATAATACAGTAGCAA
CCCTCTATTGTGTGCATCAAAGGATAGAGATAAAAGACACCAAGGAAGCT
TTAGACAAGATAGAGGAAGAGCAAAACAAAAGTAAGACCACCGCACAGCA
AGCGGCCGCTGATCTTCAGACCTGGAGGAGGAGATATGAGGGACAATTGG
AGAAGTGAATTATATAAATATAAAGTAGTAAAAATTGAACCATTAGGAGT
AGCACCCACCAAGGCAAAGAGAAGAGTGGTGCAGAGAGAAAAAGAGCAG
TGGGAATAGGAGCTTTGTTCCTTGGGTTCTTGGGAGCAGCAGGAAGCACT
ATGGGCGCAGCGTCAATGACGCTGACGGTACAGGCCAGACAATTATTGTC
TGGTATAGTGCAGCAGCAGAACAATTTGCTGAGGGCTATTGAGGCGCAAC
AGCATCTGTTGCAACTCACAGTCTGGGCATCAAGCAGCTCCAGGCAAGA
ATCCTGGCTGTGGAAAGATACCTAAAGGATCAACAGCTCCTGGGGATTTG
GGGTTGCTCTGGAAAACTCATTTGCACCACTGCTGTGCCTTGGAATGCTA
GTTGGAGTAATAAATCTCTGGAACAGATTTGGAATCACACGACCTGGATG
GAGTGGGACAGAGAAATTAACAATTACACAAGCTTAATACACTCCTTAAT
TGAAGAATCGCAAAACCAGCAAGAAAAGAATGAACAAGAATTATTGGAAT
TAGATAAATGGGCAAGTTTGTGGAATTGGTTTAACATAACAAATTGGCTG
TGGTATATAAAATTATTCATAATGATAGTAGGAGGCTTGGTAGGTTTAAG
AATAGTTTTTGCTGTACTTTCTATAGTGAATAGAGTTAGGCAGGGATATT
CACCATTATCGTTTCAGACCCACCTCCCAACCCCGAGGGGACCCGACAGG
CCCGAAGGAATAGAAGAAGAAGGTGGAGAGAGAGACAGAGACAGATCCAT
TCGATTAGTGAACGGATCGGCACTGCGTGCGCCAATTCTGCAGACAAATG
GCAGTATTCATCCACAATTTTAAAAGAAAAGGGGGATTGGGGGGTACAG
TGCAGGGGAAAGAATAGTAGACATAATAGCAACAGACATACAAACTAAAG
AATTACAAAAACAAATTACAAAAATTCAAAATTTTCGGGTTTATTACAGG
GACAGCAGAGATCCAGTTTGGTTAATTAAGGGTGCAGCGGCCTCCGCGCC
GGGTTTTGGCGCCTCCCGCGGGCGCCCCCTCCTCACGGCGAGCGCTGCC
ACGTCAGACGAAGGGCGCAGGAGCGTTCCTGATCCTTCCGCCCGGACGCT
CAGGACAGCGGCCCGCTGCTCATAAGACTCGGCCTTAGAACCCCAGTATC
AGCAGAAGGACATTTTAGGACGGGACTTGGGTGACTCTAGGGCACTGGTT
TTCTTTCCAGAGAGCGGAACAGGCGAGGAAAAGTAGTCCCTTCTCGGCGA
TTCTGCGGAGGGATCTCCGTGGGGCGGTGAACGCCGATGATTATATAAGG
ACGCGCCGGGTGTGGCACAGCTAGTTCCTCGCAGCCGGGATTTGGGTCG
CGGTTCTTGTTTGTGGATCGCTGTGATCGTCACTTGGTGAGTTGCGGGCT
GCTGGGCTGGCCGGGGCTTTCGTGGCCGCCGGGCCGCTCGGTGGGACGGA
AGCGTGTGGAGAGACCGCCAAGGGCTGTAGTCTGGGTCCGCGAGCAAGGT
TGCCCTGAACTGGGGGTTGGGGGGAGCGCACAAAATGGCGGCTGTTCCCG
AGTCTTGAATGGAAGACGCTTGTAAGGCGGGCTGTGAGGTCGTTGAAACA
AGGTGGGGGGCATGGTGGGCGGCAAGAACCCAAGGTCTTGAGGCCTTCGC
TAATGCGGGAAAGCTCTTATTCGGGTGAGATGGGCTGGGGCACCATCTGG
GGACCCTGACGTGAAGTTTGTCACTGACTGGAGAACTCGGGTTTGTCGTC
TGGTTGCGGGGCGGCAGTTATGCGGTGCCGTTGGGCAGTGCACCCGTAC
CTTTGGGAGCGCGCGCCTCGTCGTGTCGTGACGTCACCCGTTCTGTTGGC
TTATAATGCAGGGTGGGGCCACCTGCCGGTAGGTGTGCGGTAGGCTTTTC
TCCGTCGCAGGACGCAGGGTTCGGGCCTAGGGTAGGCTCTCCTGAATCGA
CAGGCGCCGGACCTCTGGTGAGGGGAGGGATAAGTGAGGCGTCAGTTTCT
TTGGTCGGTTTTATGTACCTATCTTCTTAAGTAGCTGAAGCTCCGGTTTT
GAACTATGCGCTCGGGGTTGGCGAGTGTGTTTTGTGAAGTTTTTTAGGCA
CCTTTTGAAATGTAATCATTTGGGTCAATATGTAATTTTCAGTGTTAGAC
TAGTAAAGCTTCTGCAGGTCGACTCTAGAAAATTGTCCGCTAAATTCTGG
CCGTTTTTGGCTTTTTTGTTAGACAGTTAATTAAGCCACCATGAGCGAGC
TGATCAAGGAGAACATGCACATGAAGCTGTACATGGAGGGCACCGTGAAC
AACCACCACTTCAAGTGCACATCCGAGGGCGAAGGCAAGCCCTACGAGGG
CACCCAGACCATGAAGATCAAGGTGGTCGAGGGCGGCCCTCTCCCCTTCG
CCTTCGACATCCTGGCTACCAGCTTCATGTACGGCAGCAAAGCCTTCATC
AACCACACCCAGGGCATCCCCGACTTCTTTAAGCAGTCCTTCCCTGAGGG
CTTCACATGGGAGAGAATCACCACATACGAAGACGGGGGCGTGCTGACCG
CTACCCAGGACACCAGCTTCCAGAACGGCTGCATCATCTACAACGTCAAG
ATCAACGGGGTGAACTTCCCATCCAACGCCCTGTGATGCAGAAGAAAAC
ACGCGGCTGGGAGGCCAACACCGAGATGCTGTACCCCGCTGACGGCGGCC
TGAGAGGCCACAGCCAGATGGCCCTGAAGCTCGTGGGCGGGGGCTACCTG
CACTGCTCCTTCAAGACCACATACAGATCCAAGAAACCCGCTAAGAACCT
CAAGATGCCCGGCTTCCACTTCGTGGACCACAGACTGGAAAGAATCAAGG
AGGCCGACAAAGAGACCTACGTCGAGCAGCACGAGATGGCTGTGGCCAAG
TACTGCGACCTCCCTAGCAAACTGGGGCACAGATAATAACCTGCAGGCGG
GCCAGATATACGCGTTGACATTGATTATTGACTAGTTATTAATAGTAATC
AATTACGGGGTCATTAGTTCATAGCCCATATATGGAGTTCCGCGTTACAT
AACTTACGGTAAATGGCCCGCCTGGCTGACCGCCCAACGACCCCCGCCCA
TTGACGTCAATAATGACGTATGTTCCCATAGTAACGCCAATAGGGACTTT
CCATTGACGTCAATGGGTGGAGTATTTACGGTAAACTGCCCACTTGGCAG
TACATCAAGTGTATCATATGCCAAGTACGCCCCCTATTGACGTCAATGAC
GGTAAATGGCCCGCCTGGCATTATGCCCAGTACATGACCTTATGGGACTT
TCCTACTTGGCAGTACATCTACGTATTAGTCATCGCTATTACCATGGTGA
TGCGGTTTTGGCAGTACATCAATGGGCGTGGATAGCGGTTTGACTCACGG
GGATTTCCAAGTCTCCACCCCATTGACGTCAATGGGAGTTTGTTTTGGCA
```

-continued

CCAAAATCAACGGGACTTTCCAAAATGTCGTAACAACTCCGCCCCATTGA

CGCAAATGGGCGGTAGGCGTGTACGGTGGGAGGTCTATATAAGCAGCGGT

AACCCCCGGGTACCGGTCGCCACCATGGTGAGCAAGGGCGAGGAGCTGTT

CACCGGGGTGGTGCCCATCCTGGTCGAGCTGGACGGCGACGTAAACGGCC

ACAAGTTCAGCGTGTCCGGCGAGGGCGAGGGCGATGCCACCTACGGCAAG

CTGACCCTGAAGTTCATCTGCACCACCGGCAAGCTGCCCGTGCCCTGGCC

CACCCTCGTGACCACCCTGACCTACGGCGTGCAGTGCTTCAGCCGCTACC

CCGACCACATGAAGCAGCACGACTTCTTCAAGTCCGCCATGCCCGAAGGC

TACGTCCAGGAGCGCACCATCTTCTTCAAGGACGACGGCAACTACAAGAC

CCGCGCCGAGGTGAAGTTCGAGGGCGACACCCTGGTGAACCGCATCGAGC

TGAAGGGCATCGACTTCAAGGAGGACGGCAACATCCTGGGGCACAAGCTG

GAGTACAACTACAACAGCCACAACGTCTATATCATGGCCGACAAGCAGAA

GAACGGCATCAAGGTGAACTTCAAGATCCGCCACAACATCGAGGACGGCA

GCGTGCAGCTCGCCGACCACTACCAGCAGAACACCCCCATCGGCGACGGC

CCCGTGCTGCTGCCCGACAACCACTACCTGAGCACCCAGTCCGCCCTGAG

CAAAGACCCCAACGAGAAGCGCGATCACATGGTCCTGCTGGAGTTCGTGA

CCGCCGCCGGGATCACTCTCGGCATGGACGAGCTGTACAAGTAAAGCGGC

CGCGACTCTAGAGATCTCTACAGGAGGATCTCATGCATCGGATCCGCGAA

AAGTCCGGAATTCATACTGTGAAGTACACTGCATATAAGGAGTGTGGTAT

AGTATAAAGAAACTTTCTGCAGGTAGTAATTATAGTGAAGATTTTAGGTT

TACAAAGCCCTAGCTGTTTTCTGTGTAGCTTTTATTATTCTTATGACTCT

TGACAAGTTTGTAGCTTCACCATATACATTTAATATTTTGCAATAATTGG

CCTTGTTCCTGAGCTGTTGGATTCGGGGCCGTAGCACTGTCTGAGAGGTT

TACATTTCTCACAGTGAACCGGTCTCTTTTTCAGCTGCTTCCTGGCTTCT

TTTTACTCAGGTTTCCACTGCTTTTTTGCTTTTTTTAATGCTGTATGAAG

GTGTTAACATTTGTTTATATTTTTCATTAATTGTAATACCTTTAAATCAT

GCATCATACTCAGAAATAGGGATTAGAATTTAAGTGACATCTTTGGCCCA

ATTCCTAGCCCCGCAGACACTAGCGCCACCCCCGCCGCCCGCGGTGCTGA

CGTCAGCCTGCAAGCCCCGCCCCCGCGTCTCCAGGGCAACCGTGGCTTTC

GATTGTTACTGTGGGAACCGGAGGTAACAGTCTACAGCCATGGTCGCCCC

GCAGCACGCCCACGCTCCCCACCACTCCCGAGTTCTGCCAGCCTGGGTTT

GGGCAGATACAGAGCAAGAGGAGGCGGGGCAATTG

| Name | Type | Minimum | Maximum | Length |
|---|---|---|---|---|
| precursor miR132 | ncRNA | 11,755 | 11,979 | 225 |
| precursor-miR128 | ncRNA | 11,314 | 11,748 | 435 |
| EGFP CDS | gene | 10,525 | 11,244 | 720 |
| CMVp CDS | CDS | 9,918 | 10,494 | 577 |
| turbo RFP | gene | 9,191 | 9,886 | 696 |
| hUbCp CDS | CDS | 7,946 | 9,174 | 1,229 |
| cPPT CDS | CDS | 7,772 | 7,787 | 16 |
| RRE CDS | CDS | 7,008 | 7,241 | 234 |
| Psi CDS | CDS | 6,454 | 6,498 | 45 |
| 5'LTR CDS; del3'LTR CDS | CDS | 6,163 | 6,343 | 181 |

-continued

| Name | Type | Minimum | Maximum | Length |
|---|---|---|---|---|
| CMVp CDS | CDS | 5,567 | 6,143 | 577 |
| AMP CDS | CDS | 4,238 | 5,238 | 1,001 |
| SV40-pA CDS | CDS | 3,007 | 3,126 | 120 |
| Bleo CDS | CDS | 2,500 | 2,871 | 372 |
| EM7p CDS | CDS | 2,432 | 2,499 | 68 |
| SV40p CDS | CDS | 2,070 | 2,338 | 269 |
| F1 origin | misc_feature | 1,632 | 1,938 | 307 |
| bGH-Ter CDS | CDS | 1,342 | 1,569 | 228 |
| 5'LTR CDS; del3'LTR CDS | CDS | 1,133 | 1,313 | 181 |
| U3PPT CDS | CDS | 796 | 817 | 22 |
| WPRE CDS | CDS | 22 | 609 | 588 |
| FuGW backbone misc signal | misc_signal | 1 | 7,926 | 7,926 |

SEQ ID NO: 2 - Forward primer:
(SEQ ID NO: 2)
AATGATACGGCGACCACCGAGATCTACACCGCTGGCAAGTGTAGC SEQ ID NO: 3 - Barcoded reverse primer:
(SEQ ID NO: 3)
CAAGCAGAAGACGGCATACGAGATNNNNNNGGGAGGGCCCGTTG SEQ ID NO: 4 - Illumina sequencing primer:
(SEQ ID NO: 4)
CCACGAGGATTCGAAAAGGTGAACCGACCCGGTCGATGCACTAGT SEQ ID NO: 5 - Illumina indexing primer:
(SEQ ID NO: 5)
CCTAGGAGCAAGTACGAACAACGGGCCCTCCC SEQ ID NO: 6 - precursor miR-124
AGGTGGGAGTACTGCTCAGAGCTACAACTCTAGGAGTAGGGACTCCAAGC

CTAGAGCTCCAAGAGAGGGTGAAGGGCAGGGAGAAAATTATAGTAATAGT

TGCAATGAGTCACTTGCTTCTAGATCAAGATCAGAGACTCTGCTCTCCGT

GTTCACAGCGGACCTTGATTTAATGTCATACAATTAAGGCACGCGGTGAA

TGCCAAGAGCGGAGCCTACAGCTGCACTTGAAGGACATCCGAGAGAAGTT

AGGAAGGGTGGGAGAAACAATTCTAGAATGAACCCATCCTGTGCGACAC

SEQ ID NO: 7 - precursor miR-128
ATACTGTGAAGTACACTGCATATAAGGAGTGTGGTATAGTATAAAGAAAC

TTTCTGCAGGTAGTAATTATAGTGAAGATTTTAGGTTTACAAAGCCCTAG

CTGTTTTCTGTGTAGCTTTTATTATTCTTATGACTCTTGACAAGTTTGTA

GCTTCACCATATACATTTAATATTTTGCAATAATTGGCCTTGTTCCTGAG

CTGTTGGATTCGGGGCCGTAGCACTGTCTGAGAGGTTTACATTTCTCACA

GTGAACCGGTCTCTTTTTCAGCTGCTTCCTGGCTTCTTTTTACTCAGGTT

TCCACTGCTTTTTTGCTTTTTTTAATGCTGTATGAAGGTGTTAACATTTG

TTTATATTTTTCATTAATTGTAATACCTTTAAATCATGCATCATACTCAG

AAATAGGGATTAGAATTTAAGTGACATCTTTGGCC

SEQ ID NO: 8 - precursor miR-132
CTAGCCCCGCAGACACTAGCGCCACCCCCGCCGCCCGCGGTGCTGACGTC

AGCCTGCAAGCCCCGCCCCCGCGTCTCCAGGGCAACCGTGGCTTTCGATT

GTTACTGTGGGAACCGGAGGTAACAGTCTACAGCCATGGTCGCCCCGCAG

CACGCCCACGCTCCCCACCACTCCCGAGTTCTGCCAGCCTGGGTTTGGGC

AGATACAGAGCAAGAGGAGGCGGGG

-continued

SEQ ID NO: 9 - miR-124 sensor
GGCACAGATAATAACCTGCAAAAAGGCATTCACCGCGTGCCTTAGGCATT

CACCGCGTGCCTTAGGCATTCACCGCGTGCCTTAGGCATTCACCGCGTGC

CTTAAATGCAGGCGGGCCAGATATAC

SEQ ID NO: 10 - miR-128 sensor
GGCACAGATAATAACCTGCAAAAAGAGACCGGTTCACTGTGAAAAGAGAC

CGGTTCACTGTGAAAAGAGACCGGTTCACTGTGAAAAGAGACCGGTTCAC

TGTGAAATGCAGGCGGGCCAGATATAC

SEQ ID NO: 11 - miR-132 sensor
GGCACAGATAATAACCTGCAAAAACGACCATGGCTGTAGACTGTTACGAC

CATGGCTGTAGACTGTTACGACCATGGCTGTAGACTGTTACGACCATGGC

TGTAGACTGTTAAATGCAGGCGGGCCAGATATAC

REFERENCES

1. Kitagawa M, Ara T, Arifuzzaman M, Ioka-Nakamichi T, Inamoto E, et al. 2005. Complete set of ORF clones of *Escherichia coli* ASKA library (a complete set of *E. coli* K-12 ORF archive): unique resources for biological research. *DNA research*: an international journal for rapid publication of reports on genes and genomes 12:291-9
2. Soo V W, Hanson-Manful P, Patrick W M. 2011. Artificial gene amplification reveals an abundance of promiscuous resistance determinants in *Escherichia coli. Proceedings of the National Academy of Sciences of the United States of America* 108:1484-9
3. Butland G, Babu M, Diaz-Mejia J J, Bohdana F, Phanse S, et al. 2008. eSGA: *E. coli* synthetic genetic array analysis. *Nature Methods* 5:789-95
4. Pan X, Yuan D S, Xiang D, Wang X, Sookhai-Mahadeo S, et al. 2004. A robust toolkit for functional profiling of the yeast genome. *Molecular Cell* 16:487-96
5. Tong A H, Lesage G, Bader G D, Ding H, Xu H, et al. 2004. Global mapping of the yeast genetic interaction network. *Science* 303:808-13
6. Gibson D G, Young L, Chuang R Y, Venter J C, Hutchison C A, 3rd, Smith H O. 2009. Enzymatic assembly of DNA molecules up to several hundred kilobases. *Nature Methods* 6:343-5
7. Anderson J C, Dueber J E, Leguia M, Wu G C, Goler J A, et al. 2010. BglBricks: A flexible standard for biological part assembly. *Journal of Biological Engineering* 4:1
8. Son E Y, Ichida J K, Wainger B J, Toma J S, Rafuse V F, et al. 2011. Conversion of mouse and human fibroblasts into functional spinal motor neurons. *Cell Stem Cell* 9:205-18
9. Merryman C G, D. G. 2012. Methods and applications for assembling large DNA constructs. *Metabolic Engineering* 14:196-204
10. Roth F P, Suzuki Y, Mellor J. US Patent Publication No. US 2009/0098555.
11. Wang H H, Isaacs F J, Carr P A, Sun Z Z, Xu G, et al. 2009. Programming cells by multiplex genome engineering and accelerated evolution. *Nature* 460:894-8
12. Mochon, A. B. et al. 2011. New Delhi metallo-beta-lactamase (NDM-1)-producing *Klebsiella pneumoniae*: case report and laboratory detection strategies. *Journal of clinical microbiology* 49:1667-1670.
13. Yu, H. et al. Next-generation sequencing to generate interactome datasets. Nature methods 8, 478-480, doi:10.1038/nmeth.1597 (2011).
14. Berezikov, E. et al. Evolution of microRNA diversity and regulation in animals. Nat Rev Genet 12, 846-860 (2011).
15. Ambros, V. The functions of animal microRNAs. Nature 431, 350-355 (2004).
16. Gangarajiu, V. K. and Lin, H. MicroRNAs: key regulators of stem cells. Nat Rev Mol Cell Bio 10, 116-125 (2009).
17. Inui, M. et al. MicroRNA control of signal transduction. Nat Rev Mol Cell Bio 11, 222-263 (2010).
18. Esteller M., et al., Non-coding RNAs in human disease. Nat Rev Genet 12, 861-874 (2011).
19. Eacker, S. M. et al. Understanding microRNAs in neurodegeneration. Nat Rev Neurosci 10, 837-841 (2009).
20. Kong, Y. W. et al. MicroRNAs in cancer management. Lancet Oncol 13, e249-258 (2012).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or," as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A genetic construct comprising:
   a DNA element;
   a first compatible end element and a second compatible end element flanking the DNA element, wherein the first and second compatible end elements are capable of annealing to each other;
   a barcode element;
   a third compatible end element and a fourth compatible end element flanking the barcode element, wherein the third and fourth compatible end elements are capable of annealing to each other but are not capable of annealing to the first or second compatible end elements; and
   a separation site located between the fourth compatible end element and the first compatible end element, wherein the DNA element, first compatible end element and second compatible end element are on one side of the separation site, and the barcode element, third compatible end element and fourth compatible end element are on the other side of the separation site.

2. A genetic construct comprising:
   a plurality of DNA elements;
   a first compatible end element and a second compatible end element flanking the plurality of DNA elements, wherein the first and second compatible end elements are capable of annealing to each other;
   a plurality of barcode elements;
   a third compatible end element and a fourth compatible end element flanking the plurality of barcode elements, wherein the third and fourth compatible end elements are capable of annealing to each other but are not capable of annealing to the first or second compatible end elements; and
   a separation site located between the plurality of DNA elements and the plurality of barcode elements.

3. A method for generating a combinatorial genetic construct, comprising:
   providing a vector containing a first genetic construct according to claim 1;
   cleaving the vector at the separation site within the first genetic construct, resulting in the first genetic construct being separated into first and second segments;
   providing a second genetic construct according to claim 1; and
   annealing the second genetic construct to the cleaved vector, wherein the annealing occurs at compatible end elements within the first and second genetic constructs that are capable of annealing to each other, and wherein after annealing, the second genetic construct is integrated between the first and second segments of the first genetic construct, creating a combinatorial genetic construct.

4. The method of claim 3, wherein the method is iterative.

5. A method for identification of a DNA element or a plurality of DNA elements, comprising:
   providing a genetic construct according to claim 1;
   conducting an assay to determine the DNA sequence of the barcode or plurality of barcodes within the genetic construct and/or the DNA sequence of the DNA element or plurality of DNA elements within the genetic construct; and identifying the DNA element or plurality of DNA elements.

6. A library comprising:

two or more genetic constructs according to claim 1.

7. A method for generating a combinatorial genetic construct, comprising:

providing a vector comprising:
  a first DNA element,
  a first barcode element, and
  two site-specific recombination elements located between the first DNA element and the first barcode element;

providing a first insert comprising:
  a second DNA element,
  a second barcode element, and
  site-specific recombination elements flanking each of the second DNA element and the second barcode element, such that two site-specific recombination elements are located between the second DNA element and the second barcode element that are not compatible with the site-specific recombination elements within the vector, and two site-specific recombination elements are located outside of the second DNA element and the second barcode element that are compatible with the site-specific recombination elements within the vector;

conducting site specific recombination between the vector and the first insert, wherein the site specific recombination occurs between the site-specific recombination elements within the vector located between the first DNA element and the first barcode element and the compatible site-specific recombination elements within the first insert located outside of the second DNA element and the second barcode element, and wherein following site-specific recombination, the first insert is located within the vector, and the vector contains multiple DNA elements and multiple barcode elements, with two site-specific recombination elements located between the multiple DNA elements and the multiple barcode elements;

providing a second insert comprising:
  a third DNA element,
  a third barcode element, and
  site-specific recombination elements flanking each of the third DNA element and the third barcode element, such that two site-specific recombination elements are located between the third DNA element and the third barcode element that are not compatible with the two site-specific recombination elements located between the multiple DNA elements and the multiple barcode elements of the vector, and two site-specific recombination elements are located outside of the third DNA element and the third barcode element that are compatible with the two site-specific recombination elements located between the multiple DNA elements and the multiple barcode elements of the vector;

conducting site specific recombination between the vector and the second insert, wherein the site specific recombination occurs between the site-specific recombination elements within the vector located between the multiple DNA elements and the multiple barcode elements and the compatible site-specific recombination elements within the second insert located outside of the third DNA element and the third barcode element, and wherein following site-specific recombination, the second insert is located within the vector, and the vector contains multiple DNA elements and multiple barcode elements, with two site-specific recombination elements located between the multiple DNA elements and the multiple barcode elements; and repeating the site-specific recombination an $n^{th}$ number of times, alternating between site-specific recombination between the vector and the first insert and site-specific recombination between the vector and the second insert, thereby creating a combinatorial genetic construct.

8. A combinatorial genetic construct produced by the method of claim 7.

9. A method for identification of a DNA element or a plurality of DNA elements, comprising:

providing a combinatorial genetic construct according to claim 8;

conducting an assay to determine the DNA sequence of one or more barcode elements within the combinatorial genetic construct and/or the DNA sequence of one or more DNA elements within the combinatorial genetic construct; and identifying the DNA element or plurality of DNA elements.

10. A method for generating a combinatorial genetic construct, comprising:

providing a vector comprising:
  a first DNA element,
  a first barcode element, and
  a recognition site for a first restriction enzyme located between the first DNA element and the first barcode element;

providing an insert comprising:
  a second DNA element,
  a second barcode element,
  a recognition site for the first restriction enzyme located between the second DNA element and the second barcode element, and
  two recognition sites for one or more restriction enzymes that are distinct from the first restriction enzyme located outside of the second DNA element and second barcode element, such that restriction digestion at the recognition site within the vector and at the two recognition sites located outside of the second DNA element and second barcode element within the insert generates compatible ends;

digesting the vector and insert with restriction enzymes;

annealing the insert to the vector, thereby producing a combinatorial genetic construct containing multiple DNA elements and multiple barcode elements; and optionally repeating the method an $n^{th}$ number of times.

11. A combinatorial genetic construct produced by the method of claim 10.

12. A method for identification of a DNA element or a plurality of DNA elements, comprising:

providing a combinatorial genetic construct according to claim 11;

conducting an assay to determine the DNA sequence of one or more barcode elements within the combinatorial genetic construct and/or the DNA sequence of one or more DNA elements within the combinatorial genetic construct; and identifying the DNA element or plurality of DNA elements.

13. A method for generating a combinatorial genetic construct, comprising:

providing a vector containing a first genetic construct according to claim 2;

cleaving the vector at the separation site within the first genetic construct, resulting in the first genetic construct being separated into first and second segments;

providing a second genetic construct according to claim 2; and annealing the second genetic construct to the cleaved vector, wherein the annealing occurs at compatible end elements within the first and second genetic constructs that are capable of annealing to each other, and wherein after annealing, the second genetic construct is integrated between the first and second segments of the first genetic construct, creating a combinatorial genetic construct.

14. The method of claim 13, wherein the method is iterative.

15. A method for identification of a DNA element or a plurality of DNA elements, comprising:

providing a genetic construct according to claim 2;

conducting an assay to determine the DNA sequence of the barcode or plurality of barcodes within the genetic construct and/or the DNA sequence of the DNA element or plurality of DNA elements within the genetic construct; and identifying the DNA element or plurality of DNA elements.

16. A library comprising:

two or more genetic constructs according to claim 2.

* * * * *

SEQUENCE LISTING

```
<160> NUMBER OF SEQ ID NOS: 27

<210> SEQ ID NO 1
<211> LENGTH: 11985
<212> TYPE: DNA
<213> ORGANISM: Artificial Sequence
<220> FEATURE:
<223> OTHER INFORMATION: Tandem precursor-miR

<400> SEQUENCE: 1
cgatatcaag cttatcgata atcaacctct ggattacaaa atttgtgaaa gattgactgg      60
tattcttaac tatgttgctc cttttacgct atgtggatac gctgctttaa tgcctttgta     120
tcatgctatt gcttcccgta tggctttcat tttctcctcc ttgtataaat cctggttgct     180
gtctctttat gaggagttgt ggcccgttgt caggcaacgt ggcgtggtgt gcactgtgtt     240
tgctgacgca accccactg gttggggcat tgccaccacc tgtcagctcc tttccgggac      300
tttcgctttc cccctcccta ttgccacggc ggaactcatc gccgcctgcc ttgcccgctg     360
ctggacaggg gctcggctgt tgggcactga caattccgtg gtgttgtcgg ggaaatcatc     420
gtcctttcct tggctgctcg cctgtgttgc cacctggatt ctgcgcggga cgtccttctg     480
ctacgtccct tcggccctca atccagcgga ccttccttcc cgcggcctgc tgccggctct     540
gcggcctctt ccgcgtcttc gccttcgccc tcagacgagt cggatctccc tttgggccgc     600
ctccccgcat cgataccgtc gacctcgaga cctagaaaaa catggagcaa tcacaagtag     660
caatacagca gctaccaatg ctgattgtgc ctggctagaa gcacaagagg aggaggaggt     720 gggtttttcca gtcacacctc aggtaccttt aagaccaatg acttacaagg cagctgtaga    780
```

```
tcttagccac ttttaaaag aaaggggggg actggaaggg ctaattcact cccaacgaag    840
acaagatatc cttgatctgt ggatctacca cacacaaggc tacttccctg attggcagaa    900
ctacacacca gggccaggga tcagatatcc actgaccttt ggatggtgct acaagctagt    960
accagttgag caagagaagg tagaagaagc caatgaagga gagaacaccc gcttgttaca   1020
ccctgtgagc ctgcatggga tggatgaccc ggagagagaa gtattagagt ggaggtttga   1080
cagccgccta gcatttcatc acatggcccg agagctgcat ccggactgta ctgggtctct   1140
ctggttagac cagatctgag cctgggagct ctctggctaa ctagggaacc cactgcttaa   1200
gcctcaataa agcttgcctt gagtgcttca agtagtgtgt gcccgtctgt tgtgtgactc   1260
tggtaactag agatccctca gacccttta gtcagtgtgg aaaatctcta gcagggcccg   1320
tttaaacccg ctgatcagcc tcgactgtgc cttctagttg ccagccatct gttgtttgcc   1380
cctcccccgt gccttccttg accctggaag gtgccactcc cactgtcctt tcctaataaa   1440
atgaggaaat tgcatcgcat tgtctgagta ggtgtcattc tattctgggg ggtgggtgg    1500
ggcaggacag caaggggag gattgggaag acaatagcag gcatgctggg gatgcggtgg   1560
gctctatggc ttctgaggcg gaaagaacca gctggggctc tagggggtat ccccacgcgc   1620
cctgtagcgg cgcattaagc gcggcgggtg tggtggttac gcgcagcgtg accgctacac   1680
ttgccagcgc cctagcgccc gctcctttcg ctttcttccc ttcctttctc gccacgttcg   1740
ccggctttcc ccgtcaagct ctaaatcggg ggctccctt agggttccga tttagtgctt   1800
tacggcacct cgaccccaaa aaacttgatt agggtgatgg ttcacgtagt gggccatcgc   1860
cctgatagac ggtttttcgc cctttgacgt tggagtccac gttctttaat agtggactct   1920
tgttccaaac tggaacaaca ctcaacccta tctcggtcta ttcttttgat ttataaggga   1980
ttttgccgat ttcggcctat tggttaaaaa atgagctgat ttaacaaaaa tttaacgcga   2040
attaattctg tggaatgtgt gtcagttagg gtgtggaaag tccccaggct ccccagcagg   2100
cagaagtatg caaagcatgc atctcaatta gtcagcaacc aggtgtggaa agtccccagg   2160
ctccccagca ggcagaagta tgcaaagcat gcatctcaat tagtcagcaa ccatagtccc   2220
gcccctaact ccgcccatcc cgcccctaac tccgcccagt tccgcccatt ctccgcccca   2280
tggctgacta ttttttttta tttatgcaga ggccgaggcc gcctctgcct ctgagctatt   2340
ccagaagtag tgaggaggct ttttggagg cctaggcttt tgcaaaaagc tcccgggagc   2400
ttgtatatcc attttcggat ctgatcagca cgtgttgaca attaatcatc ggcatagtat   2460
atcggcatag tataatacga caaggtgagg aactaaacca tggccaagtt gaccagtgcc   2520
gttccggtgc tcaccgcgcg cgacgtcgcc ggagcggtcg agttctggac cgaccggctc   2580
gggttctccc gggacttcgt ggaggacgac ttcgccggtg tggtccggga cgacgtgacc   2640
ctgttcatca gcgcggtcca ggaccaggtg gtgccggaca cacctggc ctgggtgtgg   2700
gtgcgcggcc tggacgagct gtacgccgag tggtcggagg tcgtgtccac gaacttccgg   2760
gacgcctccg ggccggccat gaccgagatc ggcgagcagc cgtggggcg ggagttcgcc   2820
ctgcgcgacc cggccggcaa ctgcgtgcac ttcgtggccg aggagcagga ctgacacgtg   2880
ctacgagatt tcgattccac cgccgccttc tatgaaaggt tgggcttcgg aatcgttttc   2940
cgggacgccg gctggatgat cctccagcgc ggggatctca tgctggagtt cttcgcccac   3000
cccaacttgt ttattgcagc ttataatggt tacaaataaa gcaatagcat cacaaatttc   3060
acaaataaag catttttttc actgcattct agttgtggtt tgtccaaact catcaatgta   3120
```

-continued

```
tcttatcatg tctgtatacc gtcgacctct agctagagct tggcgtaatc atggtcatag    3180
ctgtttcctg tgtgaaattg ttatccgctc acaattccac acaacatacg agccggaagc    3240
ataaagtgta aagcctgggg tgcctaatga gtgagctaac tcacattaat tgcgttgcgc    3300
tcactgcccg ctttccagtc gggaaacctg tcgtgccagc tgcattaatg aatcggccaa    3360
cgcgcgggga gaggcggttt gcgtattggg cgctcttccg cttcctcgct cactgactcg    3420
ctgcgctcgg tcgttcggct gcggcgagcg gtatcagctc actcaaaggc ggtaatacgg    3480
ttatccacag aatcagggga taacgcagga agaacatgt gagcaaaagg ccagcaaaag    3540
gccaggaacc gtaaaaaggc cgcgttgctg gcgtttttcc ataggctccg ccccctgac    3600
gagcatcaca aaaatcgacg ctcaagtcag aggtggcgaa acccgacagg actataaaga    3660
taccaggcgt ttccccctgg aagctccctc gtgcgctctc ctgttccgac cctgccgctt    3720
accggatacc tgtccgcctt tctcccttcg ggaagcgtgg cgctttctca tagctcacgc    3780
tgtaggtatc tcagttcggt gtaggtcgtt cgctccaagc tgggctgtgt gcacgaaccc    3840
cccgttcagc ccgaccgctg cgccttatcc ggtaactatc gtcttgagtc caacccggta    3900
agacacgact tatcgccact ggcagcagcc actggtaaca ggattagcag agcgaggtat    3960
gtaggcggtg ctacagagtt cttgaagtgg tggcctaact acggctacac tagaagaaca    4020
gtatttggta tctgcgctct gctgaagcca gttaccttcg gaaaaagagt tggtagctct    4080
tgatccggca aacaaaccac cgctggtagc ggtggttttt ttgtttgcaa gcagcagatt    4140
acgcgcagaa aaaaggatc tcaagaagat cctttgatct tttctacggg gtctgacgct    4200
cagtggaacg aaaactcacg ttaagggatt ttggtcatga gattatcaaa aaggatcttc    4260
acctagatcc ttttaaatta aaaatgaagt tttaaatcaa tctaaagtat atatgagtaa    4320
acttggtctg acagttacca atgcttaatc agtgaggcac ctatctcagc gatctgtcta    4380
tttcgttcat ccatagttgc ctgactcccc gtcgtgtaga taactacgat acgggagggc    4440
ttaccatctg gccccagtgc tgcaatgata ccgcgagacc cacgctcacc ggctccagat    4500
ttatcagcaa taaaccagcc agccggaagg gccgagcgca gaagtggtcc tgcaacttta    4560
tccgcctcca tccagtctat taattgttgc cgggaagcta gagtaagtag ttcgccagtt    4620
aatagtttgc gcaacgttgt tgccattgct acaggcatcg tggtgtcacg ctcgtcgttt    4680
ggtatggctt cattcagctc cggttcccaa cgatcaaggc gagttacatg atcccccatg    4740
ttgtgcaaaa aagcggttag ctccttcggt cctccgatcg ttgtcagaag taagttggcc    4800
gcagtgttat cactcatggt tatggcagca ctgcataatt ctcttactgt catgccatcc    4860
gtaagatgct tttctgtgac tggtgagtac tcaaccaagt cattctgaga atagtgtatg    4920
cggcgaccga gttgctcttg cccggcgtca atacgggata taccgcgcc acatagcaga    4980
actttaaaag tgctcatcat tggaaaacgt tcttcggggc gaaaactctc aaggatctta    5040
ccgctgttga tccagttcg atgtaaccca ctcgtgcac ccaactgatc ttcagcatct    5100
tttactttca ccagcgtttc tgggtgagca aaaacaggaa ggcaaaatgc cgcaaaaaag    5160
ggaataaggg cgacacggaa atgttgaata ctcatactct tccttttca atattattga    5220
agcatttatc agggttattg tctcatgagc ggatacatat ttgaatgtat ttagaaaaat    5280
aaacaaatag gggttccgcg cacatttccc cgaaaagtgc cacctgacgt cgacggatcg    5340
ggagatctcc cgatcccta tggtgcactc tcagtacaat ctgctctgat gccgcatagt    5400
taagccagta tctgctccct gcttgtgtgt tggaggtcgc tgagtagtgc gcgagcaaaa    5460
tttaagctac aacaaggcaa ggcttgaccg acaattgcat gaagaatctg cttagggtta    5520
```

```
ggcgttttgc gctgcttcgc gatgtacggg ccagatatac gcgttgacat tgattattga   5580
ctagttatta atagtaatca attacggggt cattagttca tagcccatat atggagttcc   5640
gcgttacata acttacggta aatggcccgc ctggctgacc gcccaacgac ccccgcccat   5700
tgacgtcaat aatgacgtat gttcccatag taacgccaat agggactttc cattgacgtc   5760
aatgggtgga gtatttacgg taaactgccc acttggcagt acatcaagtg tatcatatgc   5820
caagtacgcc ccctattgac gtcaatgacg gtaaatggcc cgcctggcat tatgcccagt   5880
acatgacctt atgggacttt cctacttggc agtacatcta cgtattagtc atcgctatta   5940
ccatggtgat gcggttttgg cagtacatca atgggcgtgg atagcggttt gactcacggg   6000
gatttccaag tctccacccc attgacgtca atgggagttt gttttggcac caaaatcaac   6060
gggactttcc aaaatgtcgt aacaactccg ccccattgac gcaaatgggc ggtaggcgtg   6120
tacggtggga ggtctatata agcagcgcgt tttgcctgta ctgggtctct ctggttagac   6180
cagatctgag cctgggagct ctctggctaa ctagggaacc cactgcttaa gcctcaataa   6240
agcttgcctt gagtgcttca agtagtgtgt gcccgtctgt tgtgtgactc tggtaactag   6300
agatccctca gacccttta gtcagtgtgg aaaatctcta gcagtggcgc ccgaacaggg   6360
acttgaaagc gaaagggaaa ccagaggagc tctctcgacg caggactcgg cttgctgaag   6420
cgcgcacggc aagaggcgag gggcggcgac tggtgagtac gccaaaaatt ttgactagcg   6480
gaggctagaa ggagagagat gggtgcgaga gcgtcagtat taagcggggg agaattagat   6540
cgcgatggga aaaaattcgg ttaaggccag ggggaagaa aaatataaa ttaaaacata   6600
tagtatgggc aagcagggag ctagaacgat tcgcagttaa tcctggcctg ttagaaacat   6660
cagaaggctg tagacaaata ctgggacagc tacaaccatc ccttcagaca ggatcagaag   6720
aacttagatc attatataat acagtagcaa ccctctattg tgtgcatcaa aggatagaga   6780
taaaagacac caaggaagct ttagacaaga tagaggaaga gcaaaacaaa agtaagacca   6840
ccgcacagca agcggccgct gatcttcaga cctggaggag gagatatgag ggacaattgg   6900
agaagtgaat tatataaata taaagtagta aaaattgaac cattaggagt agcacccacc   6960
aaggcaaaga gaagagtggt gcagagagaa aaaagagcag tgggaatagg agctttgttc   7020
cttgggttct tgggagcagc aggaagcact atgggcgcag cgtcaatgac gctgacggta   7080
caggccagac aattattgtc tggtatagtg cagcagcaga acaatttgct gagggctatt   7140
gaggcgcaac agcatctgtt gcaactcaca gtctggggca tcaagcagct ccaggcaaga   7200
atcctggctg tggaaagata cctaaaggat caacagctcc tggggatttg ggttgctct   7260
ggaaaactca tttgcaccac tgctgtgcct tggaatgcta gttggagtaa taaatctctg   7320
gaacagattt ggaatcacac gacctggatg gagtgggaca gagaaattaa caattacaca   7380
agcttaatac actccttaat tgaagaatcg caaaaccagc aagaaaagaa tgaacaagaa   7440
ttattggaat tagataaatg gcaagtttg tggaattggt ttaacataac aaattggctg   7500
tggtatataa aattattcat aatgatagta ggaggcttgg taggtttaag aatagttttt   7560
gctgtacttt ctatagtgaa tagagttagg cagggatatt caccattatc gtttcagacc   7620
cacctcccaa ccccgagggg acccgacagg cccgaaggaa tagaagaaga aggtggagag   7680
agagacagag acagatccat tcgattagtg aacggatcgg cactgcgtgc gccaattctg   7740
cagacaaatg gcagtattca tccacaattt taaaagaaaa ggggggattg ggggtacag   7800
tgcagggaa agaatagtag acataatagc aacagacata caaactaaag aattacaaaa   7860
```

```
acaaattaca aaaattcaaa attttcgggt ttattacagg gacagcagag atccagtttg    7920
gttaattaag ggtgcagcgg cctccgcgcc gggttttggc gcctcccgcg ggcgccccc     7980
tcctcacggc gagcgctgcc acgtcagacg aagggcgcag gagcgttcct gatccttccg    8040
cccggacgct caggacagcg gcccgctgct cataagactc ggccttagaa ccccagtatc    8100
agcagaagga cattttagga cgggacttgg gtgactctag ggcactggtt ttcttttccag   8160
agagcggaac aggcgaggaa aagtagtccc ttctcggcga ttctgcggag ggatctccgt    8220
ggggcggtga acgccgatga ttatataagg acgcgccggg tgtggcacag ctagttccgt    8280
cgcagccggg attgggtcg cggttcttgt ttgtggatcg ctgtgatcgt cacttggtga     8340
gttgcgggct gctgggctgg ccggggcttt cgtggccgcc gggccgctcg gtgggacgga    8400
agcgtgtgga gagaccgcca agggctgtag tctgggtccg cgagcaaggt tgccctgaac    8460
tgggggttgg ggggagcgca caaaatggcg gctgttcccg agtcttgaat ggaagacgct    8520
tgtaaggcgg gctgtgaggt cgttgaaaca aggtgggggg catggtgggc ggcaagaacc    8580
caaggtcttg aggccttcgc taatgcggga aagctcttat tcgggtgaga tgggctgggg    8640
caccatctgg ggaccctgac gtgaagtttg tcactgactg gagaactcgg gtttgtcgtc    8700
tggttgcggg ggcggcagtt atgcggtgcc gttgggcagt gcacccgtac ctttgggagc    8760
gcgcgcctcg tcgtgtcgtg acgtcacccg ttctgttggc ttataatgca gggtggggcc    8820
acctgccggt aggtgtgcgg taggcttttc tccgtcgcag gacgcagggt tcgggcctag    8880
ggtaggctct cctgaatcga caggcgccgg acctctggtg aggggaggga taagtgaggc    8940
gtcagtttct ttggtcggtt ttatgtacct atcttcttaa gtagctgaag ctccggtttt    9000
gaactatgcg ctcggggttg gcgagtgtgt tttgtgaagt ttttttaggca ccttttgaaa   9060
tgtaatcatt tgggtcaata tgtaattttc agtgttagac tagtaaagct tctgcaggtc    9120
gactctagaa aattgtccgc taaattctgg ccgttttttgg cttttttgtt agacagttaa   9180
ttaagccacc atgagcgagc tgatcaagga gaacatgcac atgaagctgt acatggaggg    9240
caccgtgaac aaccaccact tcaagtgcac atccgagggc gaaggcaagc cctacgaggg    9300
cacccagacc atgaagatca aggtggtcga gggcggccct ctccccttcg ccttcgacat    9360
cctggctacc agcttcatgt acggcagcaa agccttcatc aaccacaccc agggcatccc    9420
cgacttcttt aagcagtcct tccctgaggg cttcacatgg gagagaatca ccacatacga    9480
agacggggc gtgctgaccg ctacccagga caccagcttc cagaacggct gcatcatcta     9540
caacgtcaag atcaacgggg tgaacttccc atccaacggc cctgtgatgc agaagaaaac    9600
acgcggctgg gaggccaaca ccgagatgct gtaccccgct gacggcggcc tgagaggcca    9660
cagccagatg gccctgaagc tcgtgggcgg gggctacctg cactgctcct tcaagaccac    9720
atacagatcc aagaaacccg ctaagaacct caagatgccc ggcttccact tcgtggacca    9780
cagactggaa agaatcaagg aggccgacaa agagacctac gtcgagcagc acgagatggc    9840
tgtggccaag tactgcgacc tccctagcaa actggggcac agataataac ctgcaggcg     9900
gccagatata cgcgttgaca ttgattattg actagttatt aatagtaatc aattacgggg    9960
tcattagttc atagcccata tatggagttc cgcgttacat aacttacggt aaatggcccg   10020
cctggctgac cgcccaacga ccccgcccca ttgacgtcaa taatgacgta tgttcccata   10080
gtaacgccaa tagggacttt ccattgacgt caatgggtgg agtatttacg gtaaactgcc   10140
cacttggcag tacatcaagt gtatcatatg ccaagtacgc cccctattga cgtcaatgac   10200
ggtaaatggc ccgcctggca ttatgcccag tacatgacct tatgggactt tcctacttgg   10260
```

```
cagtacatct acgtattagt catcgctatt accatggtga tgcggttttg gcagtacatc    10320
aatgggcgtg gatagcggtt tgactcacgg ggatttccaa gtctccaccc cattgacgtc    10380
aatgggagtt tgttttggca ccaaaatcaa cgggactttc caaaatgtcg taacaactcc    10440
gccccattga cgcaaatggg cggtaggcgt gtacggtggg aggtctatat aagcagcggt    10500
aaccccgggg taccggtcgc caccatggtg agcaagggcg aggagctgtt caccggggtg    10560
gtgcccatcc tggtcgagct ggacggcgac gtaaacggcc acaagttcag cgtgtccggc    10620
gagggcgagg gcgatgccac ctacggcaag ctgaccctga agttcatctg caccaccggc    10680
aagctgcccg tgccctggcc caccctcgtg accaccctga cctacggcgt gcagtgcttc    10740
agccgctacc ccgaccacat gaagcagcac gacttcttca gtccgccat gcccgaaggc     10800
tacgtccagg agcgcaccat cttcttcaag gacgacggca actacaagac ccgcgccgag    10860
gtgaagttcg agggcgacac cctggtgaac cgcatcgagc tgaagggcat cgacttcaag    10920
gaggacggca acatcctggg gcacaagctg gagtacaact acaacagcca caacgtctat    10980
atcatggccg acaagcagaa gaacggcatc aaggtgaact tcaagatccg ccacaacatc    11040
gaggacggca gcgtgcagct cgccgaccac taccagcaga caccccccat cggcgacggc    11100
cccgtgctgc tgcccgacaa ccactacctg agcacccagt ccgccctgag caaagacccc    11160
aacgagaagc gcgatcacat ggtcctgctg gagttcgtga ccgccgccgg gatcactctc    11220
ggcatggacg agctgtacaa gtaaagcggc cgcgactcta gagatctcta caggaggatc    11280
tcatgcatcg gatccgcgaa aagtccggaa ttcatactgt gaagtacact gcatataagg    11340
agtgtggtat agtataaaga aactttctgc aggtagtaat tatagtgaag attttaggtt    11400
tacaaagccc tagctgtttt ctgtgtagct tttattattc ttatgactct tgacaagttt    11460
gtagcttcac catatacatt taatattttg caataattgg ccttgttcct gagctgttgg    11520
attcggggcc gtagcactgt ctgagaggtt tacatttctc acagtgaacc ggtctctttt    11580
tcagctgctt cctggcttct ttttactcag gtttccactg cttttttgct tttttaatg     11640
ctgtatgaag gtgttaacat tgtttatat ttttcattaa ttgtaatacc tttaaatcat     11700
gcatcatact cagaaatagg gattagaatt taagtgacat ctttggccca attcctagcc    11760
ccgcagacac tagcgccacc cccgccgccc gcggtgctga cgtcagcctg caagccccgc    11820
ccccgcgtct ccagggcaac cgtggctttc gattgttact gtgggaaccg gagtaacag     11880
tctacagcca tggtcgcccc gcagcacgcc cacgctcccc accactcccg agttctgcca    11940
gcctgggttt gggcagatac agagcaagag gaggcggggc aattg                    11985
```

```
<210> SEQ ID NO 2
<211> LENGTH: 45
<212> TYPE: DNA
<213> ORGANISM: Artificial Sequence
<220> FEATURE:
<223> OTHER INFORMATION: forward primer

<400> SEQUENCE: 2
aatgatacgg cgaccaccga gatctacacc gctggcaagt gtagc              45

<210> SEQ ID NO 3
<211> LENGTH: 44
<212> TYPE: DNA
<213> ORGANISM: Artificial Sequence
<220> FEATURE:
<223> OTHER INFORMATION: barcoded reverse primer
<220> FEATURE:
```

```
<221> NAME/KEY: misc_feature
<222> LOCATION: (25)..(30)
<223> OTHER INFORMATION: n is a, c, g, or t

<400> SEQUENCE: 3
caagcagaag acggcatacg agatnnnnnn gggagggccc gttg                44

<210> SEQ ID NO 4
<211> LENGTH: 45
<212> TYPE: DNA
<213> ORGANISM: Artificial Sequence
<220> FEATURE:
<223> OTHER INFORMATION: Illumina sequencing primer

<400> SEQUENCE: 4
ccacgaggat tcgaaaaggt gaaccgaccc ggtcgatgca ctagt              45

<210> SEQ ID NO 5
<211> LENGTH: 32
<212> TYPE: DNA
<213> ORGANISM: Artificial Sequence
<220> FEATURE:
<223> OTHER INFORMATION: Illumina indexing primer

<400> SEQUENCE: 5
cctaggagca agtacgaaca acgggccctc cc                           32

<210> SEQ ID NO 6
<211> LENGTH: 300
<212> TYPE: DNA
<213> ORGANISM: Artificial Sequence
<220> FEATURE:
<223> OTHER INFORMATION: precursor-miR-124

<400> SEQUENCE: 6
aggtgggagt actgctcaga gctacaactc taggagtagg gactccaagc ctagagctcc    60
aagagagggt gaagggcagg gagaaaatta tagtaatagt tgcaatgagt cacttgcttc   120
tagatcaaga tcagagactc tgctctccgt gttcacagcg gaccttgatt taatgtcata   180
caattaaggc acgcggtgaa tgccaagagc ggagcctaca gctgcacttg aaggacatcc   240
gagagaagtt aggaagggtg gggagaaaca attctagaat gaacccatcc tgtgcgacac   300

<210> SEQ ID NO 7
<211> LENGTH: 435
<212> TYPE: DNA
<213> ORGANISM: Artificial Sequence
<220> FEATURE:
<223> OTHER INFORMATION: precursor-miR-128

<400> SEQUENCE: 7
atactgtgaa gtacactgca tataaggagt gtggtatagt ataaagaaac tttctgcagg    60
tagtaattat agtgaagatt ttaggtttac aaagccctag ctgttttctg tgtagctttt   120
attattctta tgactcttga caagtttgta gcttcaccat atacatttaa tattttgcaa   180
taattggcct tgttcctgag ctgttggatt cggggccgta gcactgtctg agaggtttac   240
atttctcaca gtgaaccggt ctcttttttca gctgcttcct ggcttctttt tactcaggtt   300
tccactgctt ttttgctttt tttaatgctg tatgaaggtg ttaacatttg tttatatttt   360
tcattaattg taataccttt aaatcatgca tcatactcag aaatagggat tagaatttaa   420
gtgacatctt tggcc                                                   435
```

```
<210> SEQ ID NO 8
<211> LENGTH: 225
<212> TYPE: DNA
<213> ORGANISM: Artificial Sequence
<220> FEATURE:
<223> OTHER INFORMATION: precursor-miR-132

<400> SEQUENCE: 8
ctagccccgc agacactagc gccaccccg ccgcccgcgg tgctgacgtc agcctgcaag      60
ccccgccccc gcgtctccag ggcaaccgtg gctttcgatt gttactgtgg gaacggagg     120 taacagtcta cagccatggt cgccccgcag cacgcccacg ctccccacca ctcccgagtt    180
ctgccagcct gggtttgggc agatacagag caagaggagg cgggg                    225

<210> SEQ ID NO 9
<211> LENGTH: 126
<212> TYPE: DNA
<213> ORGANISM: Artificial Sequence
<220> FEATURE:
<223> OTHER INFORMATION: miR-124 sensor

<400> SEQUENCE: 9
ggcacagata taacctgca aaaggcatt caccgcgtgc cttaggcatt caccgcgtgc       60
cttaggcatt caccgcgtgc cttaggcatt caccgcgtgc cttaaatgca ggcgggccag    120
atatac                                                               126

<210> SEQ ID NO 10
<211> LENGTH: 127
<212> TYPE: DNA
<213> ORGANISM: Artificial Sequence
<220> FEATURE:
<223> OTHER INFORMATION: miR-128 sensor

<400> SEQUENCE: 10
ggcacagata taacctgca aaagagacc ggttcactgt gaaagagac cggttcactg        60 tgaaaagaga ccggttcact gtgaaaagag accggttcac tgtgaaatgc aggcgggcca   120
gatatac                                                              127

<210> SEQ ID NO 11
<211> LENGTH: 134
<212> TYPE: DNA
<213> ORGANISM: Artificial Sequence
<220> FEATURE:
<223> OTHER INFORMATION: miR-132 sensor

<400> SEQUENCE: 11
ggcacagata taacctgca aaacgacca tggctgtaga ctgttacgac catggctgta       60
gactgttacg accatggctg tagactgtta cgaccatggc tgtagactgt taaatgcagg    120
cgggccagat atac                                                      134

<210> SEQ ID NO 12
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 12
gtagacctta cttgaccaga tacagttgca atcacatagc aactcttgat agaccttact     60
tgaccagata cagttgcaat cacattatgc gtcttgatag accttacttg accagataca   120
```

```
gttctagagt c                                                          131

<210> SEQ ID NO 13
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 13
gtagacctta cttgaccaga tacagttgca atcacattat gcgtcttgat agaccttact     60
tgaccagata cagttgcaat cacatagcaa ctcttgatag accttacttg accagataca    120
gttctagagt c                                                          131

<210> SEQ ID NO 14
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 14
gtagacctta cttgaccaga tacagttgca atcacattat gcgtcttgat agaccttact     60
tgaccagata cagttgcaat cacattatgc gtcttgatag accttacttg accagataca    120
gttctagagt c                                                          131

<210> SEQ ID NO 15
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 15
gtagacctta cttgaccaga tacagttgca atcacatagc aactcttgat agaccttact     60
tgaccagata cagttgcaat cacatagcaa ctcttgatag accttacttg accagataca    120
gttctagagt c                                                          131

<210> SEQ ID NO 16
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 16
aaggatccaa aaaagatct aaagaattc aaaaaaaaaa aaaaaaaaca attgaa          56

<210> SEQ ID NO 17
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 17
ggatccattt taagatctaa aagaattctt tttttttttt tttttttttc aattg          55

<210> SEQ ID NO 18
<211> LENGTH: 95
<212> TYPE: DNA
<213> ORGANISM: Artificial Sequence
```

```
<220> FEATURE:
<223> OTHER INFORMATION: Synthetic Polynucleotide

<400> SEQUENCE: 18
aaaggatcca aaaaaagatc cattttaaga tctaaaagaa ttcttttttt tttttttttt      60
ttttcaattc aaaaaaaaaa aaaaaaaaca attga                                 95

<210> SEQ ID NO 19
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 19
cactagtaat gcgcctagtc gtagtcctag ga                                    32

<210> SEQ ID NO 20
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 20
cactagtcgt agtcctagtc gacagcctag taatgcgcct aggag                      45

<210> SEQ ID NO 21
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 21
cactagtcgt agtcctagtc gacagcctag gag                                   33

<210> SEQ ID NO 22
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 22
cactagtaag taccctagtc gtagtcctag tcgacagcct agga                       44

<210> SEQ ID NO 23
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 23
cactagtaat gcgcctagta atgcgcctag taagtaccct agtaatgcgc ctagga          56

<210> SEQ ID NO 24
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 24
```

```
cactagtcgt agtcctagtc gacagcctag tcgacagcct agtcgtagtc ctagga          56

<210> SEQ ID NO 25
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 25
aaaaaaattt tttgccatat aggcggggggg gggggggggg gaaa                     44

<210> SEQ ID NO 26
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 26
cagtatctgc cccccgccat ataggcgggg gggggggggg gggggggggg gggcagtatc     60
tg                                                                    62

<210> SEQ ID NO 27
<211> LENGTH: 111
<212> TYPE: DNA
<213> ORGANISM: Artificial Sequence
<220> FEATURE:
<223> OTHER INFORMATION: Synthetic Polynucleotide

<400> SEQUENCE: 27
aaaaattttt tgccatatct gccccccgcc ataggcgg gggggggggg gggggggggg       60
gggggcagta taggcggggg gggggggggg gggggggggg ggggaaaaa a              111
```